US012773429B2

(12) United States Patent
Lathuilière et al.

(10) Patent No.: US 12,773,429 B2
(45) Date of Patent: Oct. 27, 2026

(54) IMMORTALIZED MYOBLAST CELL LINES AND USES THEREOF

(71) Applicants: RELEASE THERAPEUTICS SA, Geneva (CH); LES HOPITAUX UNIVERSITAIRES DE GENÈVE, Geneva (CH); UNIVERSITE DE GENEVE, Geneva (CH)

(72) Inventors: Aurélien Lathuilière, Geneva (CH); Nicolas Mach, Collonge-Bellerive (CH); Patrick Salmon, Le Grand-Saconnex (CH)

(73) Assignees: RELEASE THERAPEUTICS SA, Geneva (CH); LES HOPITAUX UNIVERSITAIRES DE GENEVE, Geneva (CH); UNIVERSITE DE GENEVE, Geneva (CH)

( * ) Notice: Subject to any disclaimer, the term of this patent is extended or adjusted under 35 U.S.C. 154(b) by 1124 days.

(21) Appl. No.: 17/634,563

(22) PCT Filed: Aug. 12, 2020

(86) PCT No.: PCT/EP2020/072669

§ 371 (c)(1),
(2) Date: Feb. 11, 2022

(87) PCT Pub. No.: WO2021/028500

PCT Pub. Date: Feb. 18, 2021

(65) Prior Publication Data

US 2022/0265727 A1 Aug. 25, 2022

(30) Foreign Application Priority Data

Aug. 14, 2019 (EP) .................................... 19191867

(51) Int. Cl.
*A61K 35/34* (2015.01)
*C12N 5/077* (2010.01)
*C12N 9/12* (2006.01)

(52) U.S. Cl.
CPC ............ *A61K 35/34* (2013.01); *C12N 5/0658* (2013.01); *C12N 9/1276* (2013.01); *C12N 2501/727* (2013.01); *C12N 2510/00* (2013.01); *C12Y 207/07049* (2013.01); *C12Y 207/11002* (2013.01)

(58) Field of Classification Search
None
See application file for complete search history.

(56) References Cited

U.S. PATENT DOCUMENTS

| | | | | |
|---|---|---|---|---|
| 2010/0172917 | A1 | 7/2010 | Ter Meulen et al. | |
| 2012/0015841 | A1* | 1/2012 | Shekdar .................... | A61P 3/10 435/6.12 |
| 2022/0287959 | A1 | 9/2022 | Lathuilière et al. | |

FOREIGN PATENT DOCUMENTS

| | | | |
|---|---|---|---|
| EP | 1 960 428 | 7/2011 | |
| RU | 2 359 999 | 6/2009 | |
| WO | WO 01/14424 | 3/2001 | |
| WO | WO 2011/134989 | 11/2011 | |
| WO | WO 2014/173441 | 10/2014 | |
| WO | WO 2015/187825 | 12/2015 | |
| WO | WO 2017/064571 | 4/2017 | |
| WO | WO 2019/152820 | 8/2019 | |
| WO | WO-2019152820 A1 * | 8/2019 | ......... A61K 31/7088 |
| WO | WO 2021/028502 | 2/2021 | |

OTHER PUBLICATIONS

Shiomi et al (Gene Therapy (2011) 18, 857-866; doi:10.1038/gt.2011.44; published online Apr. 14, 2011) (Year: 2011).*
Lima et al (Vaccine 23 (2005) 1273-1283, doi:10.1016/j.vaccine.2004.08.043, Oct. 7, 2004) (Year: 2005).*
Laumonier et al (Scientific Reports | 7: 3462 | DOI:10.1038/s41598-017-03703-y, Jun. 14, 2017 ). (Year: 2017).*
CSII-CMV-RfA ((#RDB04386) https://dnaconda.riken.jp/search/RDB_clone/RDB04/RDB04386.html) (Year: 2011).*
Laumonier, T. et al. "Human myogenic reserve cells are quiescent stem cells that contribute to muscle regeneration after intramuscular transplantation in immunodeficient mice" *Scientific Reports,* published online Jun. 14, 2017, pp. 1-12, vol. 7, No. 3462.
Acarregui, A. et al. "Hydrogel-Based Scaffolds for Enclosing Encapsulated Therapeutic Cells" *BioMacromolecules,* Dec. 11, 2012, pp. 322-330, vol. 14.
Amendola, M. et al. "Coordinate dual-gene transgenesis by lentiviral vectors carrying synthetic bidirectional promoters" *Nature Biotechnology,* Dec. 26, 2004, pp. 108-116, vol. 23, No. 1.
Barde, I. et al. "Production and Titration of Lentiviral Vectors" *Current Protocols in Neuroscience,* Oct. 2010, pp. 4.21.1-4.21.23, Suppl. 53.
Douillard-Guilloux, G. et al. "Immortalization of murine muscle cells from lysosomal α-glucosidase deficient mice: A new tool to study pathophysiology and assess therapeutic strategies for Pompe disease" *Biochemical and Biophysical Research Communications,* 2009, pp. 333-338, vol. 388.
Elliott, G. D. et al. "Cryoprotectants: A review of the actions and applications of cryoprotective solutes that modulate cell recovery from ultra-low temperatures" *Cryobiology,* 2017, pp. 74-91, vol. 76.
Firth, J. D. et al. "Oxygen-regulated control elements in the phosphoglycerate kinase 1 and lactate dehydrogenase A genes: Similarities with the erythropoietin 3' enhancer" Proc. Natl. Acad. Sci. USA, Jul. 1994, pp. 6496-6500, vol. 91.
Giry-Laterrière, M. et al. "Lentiviral Vectors" *Chapter 8 in Viral Vectors for Gene Therapy: Methods and Protocols, Methods in Molecular Biology,* Otto-Wilhelm Merten and Mohamed Al-Rubeai (eds.), 2011, pp. 183-209, vol. 737.

(Continued)

*Primary Examiner* — Peter Paras, Jr.
*Assistant Examiner* — Khoa Nhat Tran
(74) *Attorney, Agent, or Firm* — SALIWANCHIK, LLOYD & EISENSCHENK

(57) ABSTRACT

The present invention relates to immortalized human cells particularly useful for cell encapsulation therapy and methods of preparation and use thereof.

6 Claims, 13 Drawing Sheets

Specification includes a Sequence Listing.

(56) References Cited

OTHER PUBLICATIONS

Gupta, R. et al. "GM-CSF-Secreting Vaccines for Solid Tumors: Moving Forward" *Discov Med.*, Jul. 2010, pp. 1-13, vol. 10, No. 50.
Hammel, P. et al. "AI334 and AQ806 antibodies recognize the spike S protein from SARS-CoV-2 by ELISA" *Antibody Reports,* 2020, pp. 1-2, vol. 3, e186.
Kaplon, H et al. "Antibodies to watch in 2019" *MABS,* 2019, pp. 219-238, vol. 11, No. 2.
Lathuilière, A. et al. "A high-capacity cell macroencapsulation system supporting the long-term survival of genetically engineered allogeneic cells" *Biomaterials,* available online Oct. 5, 2013, pp. 779-791, vol. 35.
Lathuilière, A. et al. "Genetic engineering of cell lines using lentiviral vectors to achieve antibody secretion following encapsulated implantation" *Biomaterials,* available online Oct. 23, 2013, pp. 792-802, vol. 35.
Lathuilière, A. et al. "Encapsulated Cellular Implants for Recombinant Protein Delivery and Therapeutic Modulation of the Immune System" *Int. J. Mol. Sci.,* 2015, pp. 10578-10600, vol. 16.
Lathuilière, A et al. "Lentiviral Vectors for the Engineering of Implantable Cells Secreting Recombinant Antibodies" *Chapter 11 in Lentiviral Vectors and Exosomes as Gene and Protein Delivery Tools, Methods in Molecular Biology,* Maurizio Federico (ed.), 2016, pp. 139-155, vol. 1448.
Lathuilière, A. et al. "Une usine de médicament implantable, *La technologie d'encapsulation cellulaire* version 2.0" 2021, p. 1.
Lathuilière, A. et al. "Immortalised Human Myoblast Cell Lines for the Delivery of Therapeutic Proteins Using Encapsulated Cell Technology" *JCR,* 2022, pp. 1-50.
Laumonier, T. et al. "Isolation of Human Myoblasts, Assessment of Myogenic Differentiation, and Store-operated Calcium Entry Measurement" *Journal of Visualized Experiments,* Jul. 26, 2017, pp. 1-9, vol. 125, e55918.
Li, R. H. et al. "Dose Control with Cell Lines Used for Encapsulated Cell Therapy" *Tissue Engineering,* 1999, pp. 453-465, vol. 5, No. 5.
Li, R. H. et al. "Encapsulation Matrices for Neurotrophic Factor-Secreting Myoblast Cells" *Tissue Engineering,* 2000, pp. 151-163, vol. 6, No. 2.
Mach, N. et al. "Cell-based immunotherapy combining encapsulation cell technology and irradiated autologous tumor cells: A novel technology platform that is both safe and feasible. Results from first in man trial" *Annals of Oncology,* 2015, p. 1, vol. 26, Supplement 8.
Mach, N. "Cell Encapsulation for Cancer Immunotherapy; MVX2 a human cell line for in-vivo sustained production of immunostimulatory Cytokines and therapeutic antibodies" *Festival of Biologics,* Nov. 10, 2021, pp. 1-30.
Marchetti, A. et al. "AI334, AQ806 and RB596 antibodies recognize the spike S protein from SARS-CoV-2 by immunofluorescence" *Antibody Reports,* 2020, pp. 1-3, vol. 3, e219.
Min-Wen, J. C. et al. "Assessment of different strategies for scalable production and proliferation of human myoblasts" *Cell Proliferation,* 2019, pp. 1-14, vol. 52, e12602.
Orive, G. et al. "3D cell-laden polymers to release bioactive products in the eye" *Progress in Retinal and Eye Research,* available online Oct. 18, 2018, pp. 67-82, vol. 68.
Reiser, J. et al. "Development of Multigene and Regulated Lentivirus Vectors" *Journal of Virology,* Nov. 2000, pp. 10589-10599, vol. 74, No. 22.
Salmon, P. "Generation of Human Cell Lines Using Lentiviral-Mediated Genetic Engineering" *Epithelial Cell Culture Protocols: Second Edition, Methods in Molecular Biology,* Scott H. Randell and M. Leslie Fulcher (eds.), 2012, pp. 417-448, vol. 945.
Schwenter, F. et al. "Cell encapsulation technology as a novel strategy for human anti-tumor immunotherapy" *Cancer Gene Therapy,* published online May 13, 2011, pp. 553-562, vol. 18.
Shinkai, Y. et al. "RAG-2-Deficient Mice Lack Mature Lymphocytes Owing to Inability to Initiate V(D)J Rearrangement" *Cell,* Mar. 6, 1992, pp. 855-867, vol. 68.
Stadler, G. et al. "Establishment of clonal myogenic cell lines from severely affected dystrophic muscles—CDK4 maintains the myogenic population" *Skeletal Muscle,* 2011, pp. 1-10, vol. 1, No. 12.
Uludag, H. et al. "Technology of mammalian cell encapsulation" *Advanced Drug Delivery Reviews,* 2000, pp. 29-64, vol. 42.
Wrapp, D. et al. "Structural Basis for Potent Neutralization of Betacoronaviruses by Single-Domain Camelid Antibodies" *Cell,* May 28, 2020, pp. 1004-1015, e1-e8, supplemental figures pp. 1-7, vol. 181.
Yuan, M. et al. "A highly conserved cryptic epitope in the receptor binding domains of SARS-CoV-2 and SARS-CoV" *Science,* published online Apr. 3, 2020, pp. 1-4, vol. 368.
Zhu, C.-H. et al. "Cellular senescence in human myoblasts is overcome by human telomerase reverse transcriptase and cyclin-dependent kinase 4: consequences in aging muscle and therapeutic strategies for muscular dystrophies" *Aging Cell,* 2007, pp. 515-523, vol. 6.
Written Opinion in International Application No. PCT/EP2020/072669, Dec. 7, 2020, pp. 1-10.
ABCD antibody SARS VHH-72 (ABCD_AQ806) in the AntiBodies Chemically Defined Database, p. 1, accessed Feb. 9, 2022 from https://web.expasy.org/abcd/ABCD_AQ806.
ABCD antibody anti-SARSCOV-CR3022 (ABCD_AI334) in the AntiBodies Chemically Defined Database, p. 1, accessed Feb. 9, 2022 from https://web.expasy.org/abcd/ABCD_AI334.
Grogg, J. et al. "Engineering a versatile and retrievable cell microencapsulation device for the delivery of therapeutic proteins" *iScience,* Aug. 18, 2023, pp. 1-22, vol. 26, No. 107372.
Kaura, V. et al. "Towards the immortalization of primary human myoblasts derived from patients susceptible to malignant hyperthermia and their non-susceptible relatives" *British Journal of Anaesthesia,* p. e23, May 2018, vol. 120, Issue 5.
Lathuiliere, A. "Immortalized human myoblast cell lines for the delivery of therapeutic proteins using encapsulated cell technology" *Molecular Therapy: Methods & Clinical Development,* Sep. 2022, pp. 441-458, vol. 26.
Grogg, J. et al. "Sustained delivery of low-dose anti-CTLA-4 by genetically engineered encapsulated cells drives tumor response and prolongs survival in a colorectal cancer model" *Hôpitaux Universitaires Genève, MaxiVax,* poster, 2023, p. 1.
Vernet, R. et al. "Local Sustained GM-CSF Delivery by Genetically Engineered Encapsulated Cells Enhanced Both Cellular and Humoral SARS-CoV-2 Spike-Specific Immune Response in an Experimental Murine Spike DNA Vaccination Model" *Vaccines,* May 10, 2021, pp. 1-14, vol. 9, No. vol. 484.
Audouard, E. et al. "Cell-based device provides effective therapeutic strategy to treat metachromatic leukodystrophy" *Molecular Genetics and Metabolism,* 2024, pp. 7-8, abstract 20, vol. 141.
Grogg, J. et al. "Abstract 2721: Sustained delivery of low-dose anti-CTLA-4 by genetically engineered encapsulated cells to the tumor microenvironment drives tumor response and prolongs survival in a colorectal cancer model" *Cancer Research* (*Poster Presentations—Proffered Abstracts*), Apr. 24, 2023, pp. 1-2.
Ramirez, R. D. et al. "Bypass of telomere-dependent replicative senescence (M1) upon overexpression of Cdk4 in normal human epithelial cells" Oncogene, 2003, pp. 433-444, vol. 22.
Chua, M.-W. J. et al. "Assessment of different strategies for scalable production and proliferation of human myoblasts" *Cell Proliferation,* 2019, pp. 1-14, vol. 52, e12602.

* cited by examiner

A

B

A

B

D

E 1
2
3
4
5
6
7
8
8a
9
10
10a
10b
12a
12b
13
14
15
15a
16
18a
18b
20
22
24
D
L
II
detail IV
detail V

IMMORTALIZED MYOBLAST CELL LINES AND USES THEREOF

CROSS-REFERENCE TO RELATED APPLICATION

This application is the U.S. national stage application of International Patent Application No. PCT/EP2020/072669, filed Aug. 12, 2020.

REFERENCE TO SEQUENCE LISTING

The Sequence Listing for this application is labeled "Seq-List.txt" which was created on Jan. 26, 2022 and is 66 KB. The entire content of the sequence listing is incorporated herein by reference in its entirety.

FIELD OF THE INVENTION

The present invention relates generally to the field of encapsulation and in particular the development of immortalized cell lines and methods for producing the same for use as encapsulated cellular implants for the release of therapeutic proteins or adjuvants.

BACKGROUND OF THE INVENTION

Cell encapsulation technology allows for chronic and/or localized administration of macromolecules in multiple domains. It is based on the implantation in a subject of one or several biocompatible capsules containing genetically modified cells to produce a therapeutic protein of interest. This type of capsule is generally made up of a semi-permeable membrane that provides a mechanical protection and isolates the modified cells, thus avoiding the contact between the transplanted cells and the immune cells of host and resulting in prolonged survival of the encapsulated cells. In addition, the semipermeable membrane allows the influx of nutrients and oxygen to the transplanted cells and the efflux of the protein of interest to the host, thus allowing a continuous and prolonged production.

Ex vivo gene therapy using retrievable encapsulated cellular implants has been developed as an effective strategy for the local and/or chronic delivery of therapeutic proteins. In particular, modulating the activity of the immune system of a patient has been considered as an innovative approach for the treatment of various disorders and in particular, therapeutic schemes using genetically engineered encapsulated cells have been developed such as chronic administration of monoclonal antibodies for passive immunization against neurodegenerative diseases and the local delivery of a cytokine as an adjuvant for anti-cancer vaccines (Lathuilière et al., 2015, *Int. J. Mol. Sci.,* 16, 10578-10600).

It has been recently developed a technique for anti-cancer active immunization using encapsulated cells secreting granulocyte-macrophage colony stimulating-factor (GM-CSF) allowing the standardized release of GM-CSF by the genetically modified allogeneic cells (MVX-1 cells) which has immune-protective and boosting activities useful for tumor regression. Patient immunizations is performed in healthy skin, distant from tumor deposits by combining irradiated autologous tumor cells and 2 capsules containing MVX-1 cells, producing >20 ng/24 h of huGM-CSF. This permits the production of GM-CSF and exposes the immune system to the tumor-associated antigens (TAA) expressed by the autologous tumor cells at the injection site. Local expression of GM-CSF recruits and activates antigen-presenting cells (APC), which induces both antibody-dependent cell-mediated cytotoxicity (ADCC) and cytotoxic T-lymphocyte responses at the site of the injection and systemically (WO 2017/064571) as presented in Mach et al., 2015, *Annals of Oncology,* 26 (suppl_8): 1-4. 10.1093/annonc/mdv513.

If human primary myoblast cells lines have been immortalized by retrovirus transduction of CD4 and hTERT according to Stadler et al., 2011, *Skelet Muscle,* 1:12, 94, in view of treating fascioscapulohumeral muscular dystrophy (WO 2019/152820), the resulting immortalized cells are selected with antibiotics which present a major inconvenient for use in therapy as a potential source of immunogenicity.

Other attempts of immortalization of primary human myoblasts with overexpression hTERT, CDK4R24C mutant and cyclin d1 did not generate myoblasts with myogenic potential or were not scalable in view of clinical uses (Min-wen Jason et al., 2019, *Cell proliferation,* 52(3)). In order to optimize the human application of encapsulation technologies, a critical point is the generation of an implantable, safe and usable human cell lines as a platform for the in vivo secretion of recombinant proteins of interest. Therefore, there is a need for the development of newly developed efficient cell lines particularly suitable encapsulation technology in terms of safety and long-lasting effects.

SUMMARY OF THE INVENTION

The present invention is based on the unexpected findings of a method for the preparation and selection of immortalized human myoblasts allowing achieving immortalized human myoblasts with exceptional survival characteristics in cell encapsulation devices, in particular able to differentiate under difficult metabolic conditions, while maintaining high secretion level of recombinant protein.

In particular, the method of immortalization of human myoblasts according to the invention comprises the transduction of human myoblasts isolated from a muscle tissue from a donor (e.g. healthy or autologous) with at least one lentiviral vector (such as pCLX type or pRRLSIN or other suitable lentiviral vectors such as those as described in Giry-Laterrière, 2011, *Methods Mol Biol.,* 737:183-209) encoding for CDK4 protein and at least one lentiviral vector (such as pCLX type or pRRLSIN or other suitable lentiviral vectors such as those as described in Giry-Laterrière, 2011, supra) encoding for hTERT protein and the selection of at least one immortalized individual clone (without the use of selection antibiotics) for its improved in vitro proliferation and stability properties such as improved survival when encapsulated compared to parent cell line using single cell cloning techniques. In particular, a selected immortalized human myoblast cell line obtained by a method of the invention such as for example the cell line deposited with the Culture Collection of Switzerland (CCOS) under number CCOS 1902 advantageously presents long term survival and proliferation ability in a biocompatible capsule and long-term keeping myoblast features such as for example high levels of MHC.

Further, another aspect of the invention is based on the unexpected finding that immortalized human myoblast cell lines of the invention can be easily genetically engineered to express proteins of interest, particularly useful in the field of encapsulation therapy technologies and it is provided a method for the preparation of genetically modified immortalized human myoblasts, wherein said method comprises the transduction of immortalized human myoblasts according to the invention with at least one lentiviral vector (e.g. pCLX or pRRLSIN type) encoding for the protein of interest under the control of a promoter which is overactivated in hypoxia condition, in particular PGK (phosphoglycerate kinase) promoter, in particular human PGK promoter. Under the control of this promoter, protein secretion by the genetically modified immortalized human myoblasts according to the invention is advantageously increased by a factor of 2 to 3 under hypoxia conditions which makes these cells even more interesting for use in cell encapsulation technology which subjects cells to hypoxia. In particular, a genetically modified immortalized human myoblast cell line secreting GM-CSF obtained by a method of the invention such as for example the cell line deposited under number CCOS 1901 advantageously presents long term survival and proliferation ability in an implantable device and long term keeping myoblast features with high levels of secretion of GM-CSF which are highly useful for cancer cell therapy.

An object of this invention is to provide an immortalized human cell line useful for cell encapsulation technology.

It is useful to provide an immortalized human cell line which is not tumorigenic and present a prolonged survival even in hypoxic conditions.

It is useful to provide an immortalized human cell line for autogenic transplantation which can be used without a restriction to immunoprivilaged sites.

It is useful to provide an immortalized human cell line with optimized properties without having recourse to a cell line selection by antibiotics.

It is useful to provide an immortalized human cell line which is able to be genetically engineered to secrete high levels of protein interest.

It is useful to provide genetically engineered immortalized human cells which are able to maintain high levels of expression of a gene of a protein interest without silencing overtime.

It is useful to provide genetically engineered immortalized human cells which are able to maintain high levels of secretion of a protein interest in an encapsulation device.

It is useful to provide genetically engineered immortalized human cells which are able to be frozen and thawed after being loaded in an encapsulation device and maintain high levels of secretion of a proteins interest.

Objects of this invention have been achieved by providing an immortalized human myoblast cell line as disclosed herein, a method for obtaining an immortalized human myoblast cell line and uses thereof.

Objects of this invention have also been achieved by providing genetically engineered immortalized human myoblast cells as disclosed herein, a method for obtaining genetically engineered immortalized human myoblast cells as disclosed herein and uses thereof.

Disclosed herein, according to a first aspect of the invention, is a method of establishing an immortalized human myoblast cell line, said method comprising the steps of:

a) Providing at least one primary human myoblast cell which expresses the surface marker CD56 and optionally at least one further surface marker selected from CD82 and CD146;
b) Transducing said at least one primary human myoblast cell with a lentiviral vector encoding for the cyclin-dependent kinase 4 (CDK4) gene and a lentiviral vector encoding for the catalytic subunit of the human telomerase (hTERT) gene to obtain immortalization of the said primary human myoblast cell;
c) Growing cells from at least one immortalized primary human myoblast cell obtained under step b) in a myoblast cell growth medium and isolating from the growth medium each obtained cell presenting at least one myoblast phenotypic marker in a separate culture medium;
d) Growing separately in individual culture and amplification media each isolated cell obtained under step c);
e) Selecting among all the individual culture and amplification media of step d) at least one cell line with improved stability or expression properties from the parental cell by single cell cloning;
f) Controlling the myogenic potential of the selected at least one cell line;
g) selecting individual clones based on their ability to survive in an encapsulation device;
h) optionally repeating steps d) to g) sequentially to further improve the selected line.

According to another aspect of the invention, is provided an immortalized human myoblast cell line or a composition comprising immortalized human myoblast cells or a progeny thereof derived from primary human myoblast cells, wherein said cells express CDK4 and hTERT and retain myoblast features and wherein said cells do not express an antibiotic resistance gene.

According to another aspect of the invention, is provided an immortalized human myoblast cell line deposited with CCOS under accession number 1902 (deposited on 20, Jun. 2019) or a composition or a progeny thereof.

According to another aspect of the invention, is provided an immortalized human myoblast cell line or a composition comprising immortalized human myoblast cells or a progeny thereof derived from primary human myoblast cells obtainable from a method according to the invention.

According to another aspect of the invention, is provided a method for the preparation of genetically engineered immortalized human myoblast cells expressing a therapeutic protein under hypoxic conditions.

According to another aspect of the invention, is provided a genetically engineered immortalized human myoblast cell line according to the invention or a composition or a progeny thereof.

According to another aspect of the invention, is provided a genetically immortalized human myoblast cell line secreting GM-CSF deposited with CCOS under accession number 1901 (deposited on 20, Jun. 2019) or a composition or a progeny thereof.

According to another aspect of the invention, is provided a genetically engineered immortalized human myoblast cell line or a composition or a progeny thereof obtainable from a method according to the invention.

According to another aspect of the invention, is provided genetically engineered immortalized human myoblast cells of the invention for use in encapsulated cell therapy.

According to another aspect of the invention, is provided a pharmaceutical composition comprising at least one genetically engineered immortalized human myoblast cell according to the invention and a pharmaceutically acceptable carrier, diluent or excipient thereof.

According to another aspect, the invention provides genetically engineered immortalized human myoblast cells of the invention for use in the prevention and/or treatment of a disorder or a disease, in particular a cancer, an inflammatory disorder, an infectious disease, in particular a viral infection or a neurodegenerative disorder.

According to another, the invention provides a use of genetically engineered immortalized human myoblast cells of the invention for the preparation of a pharmaceutical composition or of an implantable encapsulated cell device for the prevention and/or treatment of a disorder or a disease, in particular a cancer, an inflammatory disorder, an infectious disease, in particular a viral infection or a neurodegenerative disorder.

According to another, the invention provides an implantable biocompatible device or a kit comprising at least one immortalized human myoblast cell according to the invention in a cell culture medium.

According to another aspect, the invention provides a method of preventing or treating a disorder or a disease associated in a subject, in particular a cancer, an inflammatory disorder, an infectious disease, especially a viral infection or a neurodegenerative disorder, said method comprising administering in a subject in need thereof a therapeutically effective amount of genetically engineered immortalized human myoblast cells of the invention.

DETAILED DESCRIPTION

Figure 1:
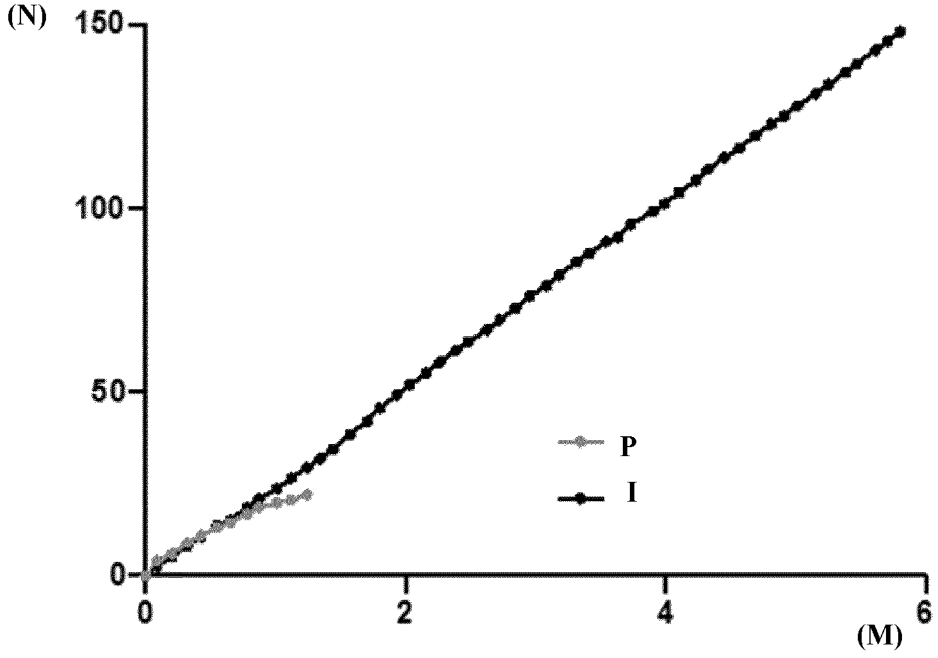
FIG. 1 represents the proliferation ability expressed as the number of cell population double (N) versus the number of months (M) after transduction of immortalized human myoblast of the invention (I), i.e. before step d) of a process of the invention compared to primary myoblast cells (P), as measured by cell counting at each passage as described in Example 1.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it such as a preventive early asymptomatic intervention; (b) inhibiting the disease, i.e., arresting its development; or relieving the disease, i.e., causing regression of the disease and/or its symptoms or conditions such as improvement or remediation of damage. In particular, the methods, uses, formulations and compositions according to the invention are useful for encapsulated cell therapy.

The term "subject" as used herein refers to mammals. For examples, mammals contemplated by the present invention include human, primates, domesticated animals such as cattle, sheep, pigs, horses, laboratory rodents, other pets and the like.

The term "effective amount" as used herein refers to an amount of at least one compound of the invention or a pharmaceutical formulation thereof according to the invention that elicits the biological or medicinal response in a tissue, system, animal or human that is being sought. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of compound of the invention sufficient to reduce the progression of the disease, notably to reduce or inhibit the progression of a disorder and thereby elicit the response being sought (i.e. an "effective amount").

The term "efficacy" of a treatment according to the invention can be measured based on changes in the course of disease in response to a use or a method according to the invention. For example, the efficacy of a treatment of cancer can be measured by a reduction of the tumor size or by an increase of the overall survival (OS), or of the progression free survival (PFS), or by obtaining disease stabilization (SD), or a decrease in serum tumor markers such as Prostate specific antigen (PSA), Cancer antigen 125 (CA125), Carcinoembryonic Antigen (CEA), or a reduced metabolic activity, reduced genetic abnormalities such as circulating tumor Desoxyribonucleic acid (ctDNA).

The term "myogenic potential" refers to the ability of the cells to form myotubes. This ability can be tested by standard techniques such as described herein or by flow cytometry, western blotting.

The term "human myoblast phenotypic marker" refers to a phenotypic feature for human myoblasts such as CD56+, CD146+, CD82+. Those can be assessed by Fluorescence-activated cell sorting (FACS) or by immunohistochemistry or western blot. According to a particular aspect, the said at least one myoblast phenotypic marker is selected from CD56+, CD146+ and CD82+.

The term "cell growth medium" refers to a medium suitable for growing myoblasts such as a culture medium supplemented with at least one growth factor such as epidermal growth factor, creatin, uridin, dexamethasone, fetal bovine serum, fetuin, bovine serum albumin, insulin or pyruvate. According to a particular embodiment, amplification medium may refer to a cell growth medium as defined above.

The term "pharmaceutical formulation" refers to preparations which are in such a form as to permit biological activity of the active ingredient(s) to be unequivocally effective and which contain no additional component which would be toxic to subjects to which the said formulation would be administered.

Method of Preparation of Immortalized Human Myoblast Cells According to the Invention According to one aspect, the invention provides a method of establishing an immortalized human myoblast cell line, said method comprising the steps of:

a) Providing at least one primary human myoblast cell which expresses the surface marker CD56 and optionally at least one further surface marker selected from CD82 and CD146;
b) Transducing said at least one primary human myoblast cell with a lentiviral vector for encoding the cyclin-dependent kinase 4 (CDK4) gene and a lentiviral vector encoding for the catalytic subunit of the human telomerase (hTERT) gene to obtain immortalization of the said primary human myoblast cell;
Growing cells from at least one immortalized primary human myoblast cell obtained under step b) in a myoblast cell growth medium and isolating from the growth medium each obtained cell presenting at least one myoblast phenotypic marker in a separate culture medium;
d) Growing separately in individual culture and amplification media each isolated cell obtained under step c);
e) Selecting among all the individual culture and amplification media of step d) at least one cell line with improved stability or expression properties from the parental cell by single cell cloning;
f) Controlling the myogenic potential of the selected at least one cell line.
g) Selecting individual clones based on their ability to survive in an encapsulation device;
h) Optionally repeating steps d) to g) sequentially to further improve the selected line.

According to a particular aspect, step a) of a method of the invention can be carried out using two separate lentiviral vectors or one single bicistronic vector such as described in Reiser et al, 2000, *J Virol.* 2000, 74(22): 10589-10599; Amendola et al, 2005, *Nat Biotech,* 23, 108-116. According to a particular aspect, the lentiviral vectors used under step b) are vectors of pCLX type such as described in Salmon, 2013, *Methods Mol Biol,* 945, 417-448.

According to a particular aspect, the said at least one primary human myoblast cell provided for transduction under step b) can be isolated from human muscle tissue by standard methods such as enzyme digestion as described in Laumonier et al., 2017, *J Vis Exp.,* 26 (125).

According to a further particular aspect, the growth of the cells under step c) until non-immortalized cells have died.

According to a further particular aspect, the growth of the cells under step c) is carried out for at least 1.5 month, i.e. the time necessary for non-immortalized cells to die.

According to a particular embodiment, selection of a primary human myoblast cell which expressed the surface marker CD56 and optionally the further surface markers CD82 and/or CD146 can be achieved by flow cytometry.

According to a particular aspect, the myoblast selected under step c) of a method of the invention present myoblast phenotypic markers CD56+, CD146+ and CD82+. This is further particularly unexpected that a method of the invention allows the selection of a cell subpopulation with this triple positivity since it has been found that not all CD56 positive cells would be CD82 positive cells. According to a further particular aspect, a method according to the invention advantageously comprises a selection/enrichment step based on the surface markers described herein.

According to a particular aspect, step d) is carried out until the cells show stable proliferation and viability when maintained in culture over 4 weeks.

According to another aspect of the invention, is provided a method for the preparation of genetically engineered immortalized human myoblast cells expressing a therapeutic protein under hypoxic conditions, wherein said method comprises the steps of:

i) Providing at least one immortalized primary human myoblast cell;
ii) Transducing said at least one immortalized primary human myoblast cell with a lentiviral vector for the expression of a target protein under the control of a phosphoglycerate kinase (PGK) promoter (e.g. human PGK);
iii) Growing separately in individual culture and amplification media each isolated cell obtained under step ii);
iv) Selecting among all the individual culture and amplification media of step iii) at least one cell line with the highest secretion level for the target protein such as by ELISA or western blotting;
v) Controlling the myogenic potential of the selected at least one cell line.

According to a particular aspect, the at least one cell line selected under step iv) is a cell line presenting a secretion level of at least 1 pg/cell/day of the target protein.

According to a particular aspect, the target protein is a human glycoprotein.

According to a particular aspect, the target protein is human GM-CSF.

According to a particular aspect, the target protein is a human monoclonal antibody.

According to a particular aspect, the target protein is selected from rituximab, ipilimumab, and gantenerumab.

According to a particular aspect, the target protein is an antigen.

According to a particular aspect, the target protein is a viral antigen.

According to a particular aspect, the target protein is a COVID-19 spike protein or an antigenic fragment thereof.

According to a particular aspect, a method according to the invention uses under the growing step at least one growth factor selected from fetuin, epidermal growth factor or insulin.

According to a particular aspect, a method according to the invention allows growing the cells without the need to coat culture plates.

According to another aspect, the invention provides a method for the treatment by immunotherapy of a subject, said method comprising administering at least one genetically engineered immortalized human myoblast cell according to the invention in said subject in need thereof.

According to another aspect, the invention provides a method for the treatment of a cancer in a subject, said method comprising administering at least one genetically engineered immortalized human myoblast cell according to the invention in said subject.

According to another aspect, the invention provides a method of vaccination against a viral infection in a subject, said method comprising administering in a subject in need thereof a therapeutically effective amount of genetically engineered immortalized human myoblast cells of the invention wherein said cells express a viral antigen.

Cells According to the Invention

According to a particular aspect of the invention, is provided an immortalized human myoblast cell line or a composition comprising immortalized human myoblast cells or a progeny thereof derived from primary human myoblast cells, wherein said cells express CDK4 and hTERT and retain myoblast features such as ability of differentiation into myotube, in absence of expression of antibiotic resistance gene.

According to another aspect of the invention, the immortalized human myoblast cell line according to the invention present a proliferation rate corresponding to a doubling time of about 24 to about 72 hours for at least 6 months.

According to another aspect of the invention, the immortalized human myoblast cell line according to the invention present a survival term of at least about 48 hours under hypoxic conditions in standard myoblast culture medium.

According to a particular aspect of the invention, is provided immortalized human myoblast cells according to the invention are able to continue growing stably for up to at least six months in myoblast culture medium.

The immortalized human myoblast cells according to the invention have demonstrated a prolonged survival in an encapsulation device while maintaining a secretion of high levels of proteins interest and therefore offer a unique and very advantageous platform for further developing new cell lines genetically engineered to secrete proteins of interest in various domains of application.

For example, the genetically engineered immortalized human myoblast cells are typically able to secrete a protein at a rate of about 1 for about 15 pg/cell/day under standard myoblast culture conditions.

According to another aspect of the invention, is provided a genetically engineered immortalized human myoblast cell line or a composition comprising genetically engineered immortalized human myoblast cells or a progeny thereof, wherein said cells express CDK4, hTERT and expresses at least one therapeutic protein or antigen, retain myoblast features and are able to secrete said therapeutic protein or antigen.

For example, genetically engineered immortalized human myoblast cells according to the invention express GM-CSF and are able to secrete a GM-CSF. Typically, according to a particular aspect, genetically engineered immortalized human myoblast cells according are able to secrete GM-CSF at a rate of about 1 to about 5 pg/cell/day for about 6 months under standard myoblast culture conditions.

According to another aspect of the invention, is provided a genetically engineered immortalized human myoblast cell line expressing human, humanized or chimeric monoclonal antibodies (e.g. the anti-CD20 monoclonal antibody rituximab, ipilimumab, gantenerumab) or recombinant proteins (e.g. mouse or human hormones or growth factors) or antigens (e.g. viral antigens such as COVID-19 pike protein antigen).

Compositions According to the Invention

The invention provides cells and pharmaceutical compositions thereof and methods for treating a subject, preferably a mammalian subject, and most preferably a human patient who is suffering from a medical disorder.

In another embodiment, the invention provides a pharmaceutical composition containing at least one cells of the invention and a pharmaceutically acceptable carrier, diluent or excipient thereof.

Immortalized cells of the invention or formulations thereof may be administered as a pharmaceutical formulation, which can contain one or more agents according to the invention in any form described herein. For use as encapsulated cells, the cells may be prepared as various types of suspension or other fluid formulation in a cell growth medium, preferably an animal-free medium.

In one embodiment, the cells may be suspended in a suitable fluid medium, such as a growth or differentiation medium. The fluid medium may comprise a physiologically acceptable aqueous solution for the growth or maintenance of the living cells. For example, the fluid medium may comprise glucose, salts, minerals, buffers, amino acids, hormones and growth factors that the cells need and use in vitro and/or in vivo. Suitable fluid media for encapsulated cells are described, for example, in PBS, HBSS, MyoCult or cell growth medium as described herein.

In one embodiment, the cells are encapsulated in hydrogels such as polyethylene glycol (PEG), alginate or chitosan hydrogels. PEG-based encapsulation is described in more detail in Lathuillère et al., 2014, *Biomaterials* 35 780-790. Cells can grow on supporting matrices such as polyvinyl alcohol (PVA), PEG, polyethylene, polyester such as described in Li, 2000, *Tissue Eng.,* 6(2):151-63; Li, 1999, *Tissue Eng.,* 5(5):453-66; Uludag, 2000, *Adv Drug Deliv Rev.,* 42(1-2):29-64.

In one embodiment, the cell encapsulated in a device that needs to be cryopreserved may be prepared in a formulation containing cryoprotectant such as described in Elliott et al., 2017, *Cryobiology;* 76:74-91.

Implantable Devices or Kits Comprising Cells of the Invention

Immortalized myoblast cells of the invention can be used for ECT and therefore can be encapsulated in cellular implants such as in flat sheets as described in Lathuillère et al., 2014, supra or WO 2014/173441 or in hollow fiber devices such as described in Lathuillère et al., 2015, supra, depending on the secreted protein and the site of implantation of the device. Alternative devices such as described in Orive et al., 2019, *Prog Retin Eye Res,* 68:67-82 may also be used.

According to a particular aspect, is provided an implantable device containing an effective amount of immortalized human myoblast cells of the invention.

According to another particular aspect, is provided a kit for cell based therapy in a mammal, comprising an effective amount of immortalized human myoblast cells of the invention and instructions for the use thereof to prepare a cell encapsulation implant.

According to another particular aspect, is provided a kit for cell based therapy in a mammal comprising an implantable device containing an effective amount of said immortalized human myoblast cells and instructions for the use thereof.

According to a further embodiment, a kit of the invention may further comprise antigenic material (e.g. one or more antigen(s)) useful for anti-cancer or anti-infection vaccination.

According to a particular embodiment, the cell chamber of an implantable device contains between $1.0\times10^4$ cells and $8\times10^5$ immortalized human myoblast cells according to the invention (e.g., $1.0\times10^4$, $5.0\times10^4$, $1.0\times10^5$, $3.0\times10^5$, $5.0\times10^5$ or $8\times10^5$ or $10^6$ cells), depending on the application and the secreted protein. Those skilled in the art will recognize that the exact cell number in each chamber can depend both upon the growth rate of the cell/cell line encapsulated and/or the volume of the individual chambers used to construct the device According to a particular embodiment, immortalized human myoblast cells secreting GM-CSF can be conditioned in an implantable capsule as described in WO 2017/064571 in view of a use in a personalized anti-tumor cell immunotherapy as described therein.

According to a particular embodiment, an implantable device containing at least one immortalized human myoblast cell according to the invention can be cryopreserved and cryopreserved devices can be transported under vapor phase liquid nitrogen (e.g., −190° C.) conditions and/or under dry ice (e.g., −70° C.) conditions using any method(s) known in the art. Before implantation, cryopreserved devices can be thawed using any method(s) known in the art, typically in a 37° C. water bath or dry bath before implantation.

According to a particular aspect, the viability and/or functionality of the cells prior to encapsulation and/or prior implantation after thawing can be carried out to confirm their suitability for use, e.g., in transplantation. This can be accomplished using a variety of methods known in the art. For example, the cells can be stained using vital stains, such as, e.g., trypan blue or ethidium bromide or acridine orange or The Live/Dead assay kit (Molecular Probes; Thermo Fisher Scientific, Waltham, MA). In preferred embodiments, a population of cells suitable for transplantation is at least about 50%, at least about 75%, at least about 95%, or at least about 99%, viable. In other embodiments, the morphometric characteristics of the cells can be determined as a measure of the suitability of cells for use in implantation.

Mode of Administration

Cells and formulations thereof according to this invention may be administered by implantation of a biocompatible implantable device containing an effective amount of immortalized human myoblast cells of the invention which allows slow release of the protein secreted by the living cells inside the implant.

According to another aspect, cells and formulations thereof according to this invention may be administered in microcapsules or microspheres such as described in Acarregui et al., 2013 *Biomacromolecules,* 14(2), 322-330 or in hydrophobic matrices or hydrophilic matrices, biodegradable matrices or mineral matrices.

According to another aspect, cells and formulations thereof according to this invention can be directly injected as cell suspensions.

According to a particular aspect, an implantable device suitable for the cells of the invention can be as follows:

Disclosed herein is an implantable capsule comprising a cell receiving portion comprising a porous membrane surrounding a cell receiving chamber for receiving immortalized cells in a liquid media therein for the secretion of therapeutic agents, characterized in that the capsule further comprises a cell support matrix inserted within the cell receiving chamber configured for the arrangement of the immortalized cells within the cell receiving chamber.

In an embodiment, the cell support matrix comprises at least one yarn.

In an advantageous embodiment, said at least one yarn consists of or comprises a polyester material.

In an advantageous embodiment, the cell support matrix comprises a plurality of said yarns.

In an advantageous embodiment, the plurality of yarns is in a range of 5 to 20 yarns, preferably a range of 5 to 15 yarns, for instance around 10 yarns.

In an advantageous embodiment, the yarns extend within the cell receiving chamber over substantially the whole length of the chamber or at least 80 percent of the length of the cell receiving chamber.

In an advantageous embodiment, the cell receiving chamber comprises polyester yarns.

In an advantageous embodiment, the cell receiving portion further comprises a membrane support mounted in the cell receiving chamber configured for providing structural support to the porous membrane, the membrane support consisting of or comprising a coil made of a biocompatible material, for instance of stainless steel coil.

In an advantageous embodiment, the capsule further comprises an extractor portion coupled to an extractor end of the cell receiving portion configured for allowing a surgical tool to pull the implantable capsule out of an implantation site, the extractor portion comprising a retrieval thread.

In an advantageous embodiment, the retrieval thread is made of a thread of polypropylene.

In an advantageous embodiment, the extractor portion comprises an anchor tube (8) having a cavity therein within which an anchor portion (15) of a retrieval thread (9) is inserted and bonded.

In an advantageous embodiment, the anchor tube consists of or comprises a polyurethane material.

In an advantageous embodiment, the extractor portion is coupled to the cell receiving portion via a coupling comprising a connector, a connector comprising a portion inserted into an extractor end of the porous membrane and second portion inserted in a coupling end of the anchor tube.

In an advantageous embodiment, the connector is bonded to the anchor tube and the cell receiving portion by an adhesive, in particular a light curable adhesive, for instance of the type photocurable urethane methacrylate.

In an advantageous embodiment, an outer diameter of the capsule is in a range of 0.5 to 3 millimeters preferably in a range of 0.8 to 1.5 millimeters and has a length in a range of 5 to 25 millimeters preferably in a range of 8 to 20 millimeters.

In an advantageous embodiment, a length to diameter ratio of the capsule is in a range of 5 to 20.

Figures 9A, 9B, 9C, 9D, 9E:
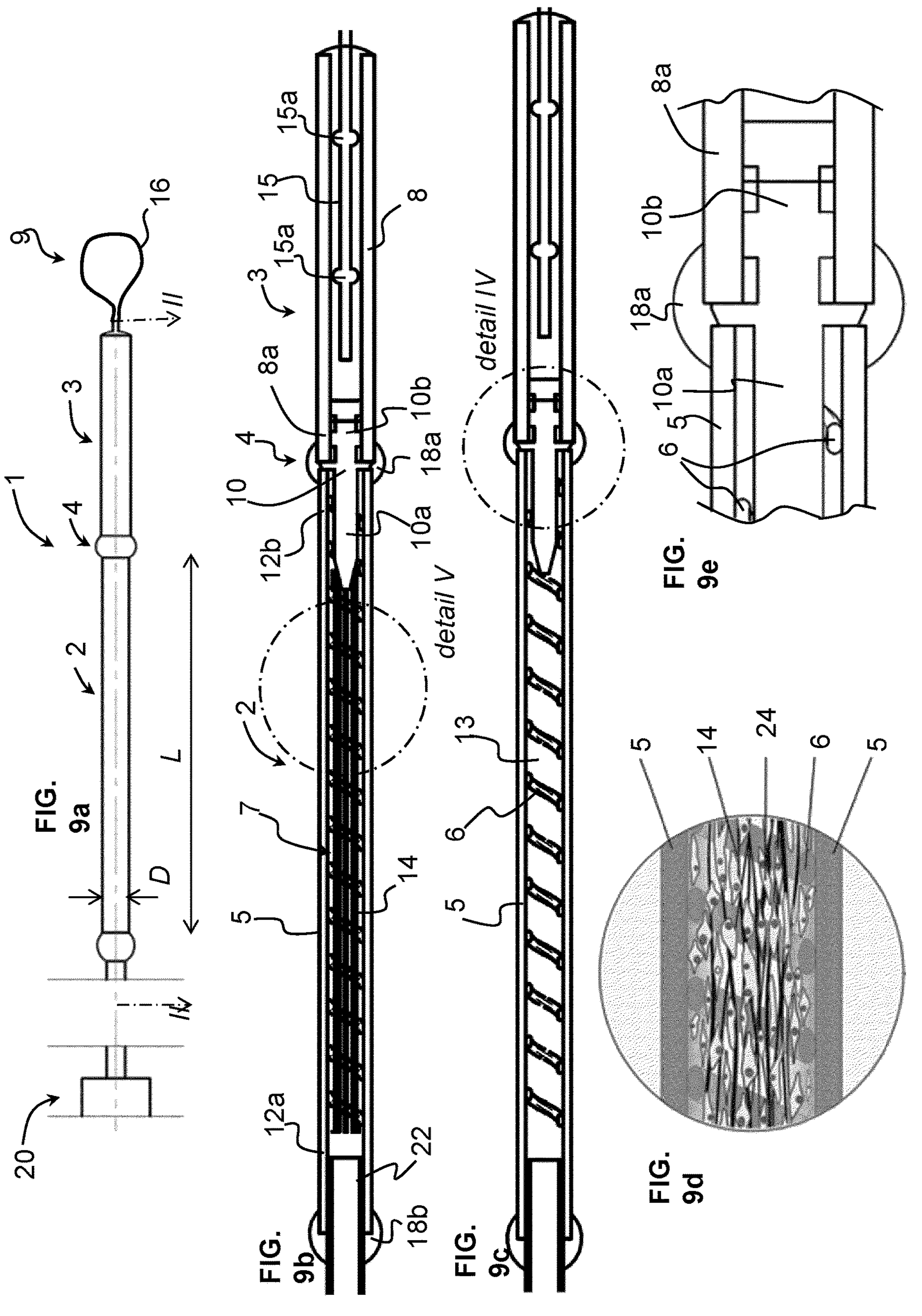
FIG. 9 is a representation of an implantable encapsulation device used in the experiments with encapsulated cells of the invention. a: is a schematic illustration of an implantable capsule according to an embodiment of this invention. b: is a cross-sectional view through line II-II of FIG. 9*a*; c: is a cross-sectional view similar to FIG. 9*b* with an internal matrix of the capsule removed; d: is a detailed view of circle IV of FIG. 9*c* of the cell receiving portion 2 inside of the implantable encapsulation device containing the immortalized myoblasts 24 according to the invention. e: is a detailed view of circle V of FIG. 9*b*.

Referring to FIG. 9, an implantable capsule 1 according to an embodiment of invention comprises a cell receiving portion 2 and an extractor portion 3 connected together by a coupling 4. The cell receiving portion 2 comprises a substantially cylindrical outer shape with a diameter that may typically be in the range of 0.5 to 3 millimeters and a length that may be typically in the range of 5 to 20 millimeters for instance around 10 millimeters. The ratio L/D of the length L to the diameter D is preferably in a range from 5 to 20 preferably in a range from 5 to 15. The capsule may be implanted in a patient's tissue by means of implantation devices that are per se well-known in the field of implants and need not be further described herein.

The cell receiving portion 2 comprises a porous membrane 5 that is configured for allowing therapeutic agents produced by the cells 24 contained in the capsule through the membrane to the surrounding tissue and to allow fluids and electrolytes and nutrients for the cells 24 to pass into the capsule through the membrane from the surrounding tissue. The porosity and the type of membrane may thus depend on the specific application and type of cells that are contained within the capsule. In an example, the membrane is for instance in a form of a polyether-sulfone (PES) membrane having a porosity around 0.65 μm configured to allow the target molecules to pass though the membrane. An example of a membrane may be used in the present invention is detailed hereafter:

An exemplary embodiment of a membrane comprises polyethersulfone based on its biocompatible chemical composition, the structure properties as well as the inherent membrane performance, such as the superior flow rates, the downstream cleanliness and the low protein binding affinity. It can be extruded in different shapes and in small diameter tubing.

The cell receiving portion 2 can have the form of a flat sheet as described in Lathuillère et al., 2014, *Biomaterials,* 35 780-790 or WO 2014/173441 or hollow fiber such as described in Lathuillère et al., 2015, supra, depending on the secreted protein and the site of implantation of the device.

The cell receiving portion 2 may contain an effective amount of cells such as for example between about $1.0\times10^4$ cells and $8\times10^5$ cells according to interest (e.g., $1.0\times10^4$, $5.0\times10^4$, $1.0\times10^5$, $3.0\times10^5$, $5.0\times10^5$ or $8\times10^5$ or $10^6$ cells), depending on the application and the secreted protein. Those skilled in the art will recognize that the exact cell number in the cell receiving portion can depend both upon the growth rate of the cell/cell line encapsulated and/or the volume of the cell receiving portion.

The porous membrane 5 surrounds a cell receiving chamber 13 and a membrane support 6 within the cell receiving chamber 13. The membrane support serves to mechanically support the porous membrane to maintain the stability of the volume in the cell receiving chamber 13 and to prevent rupture of the membrane. In the illustrated embodiment, the membrane support is in a form of a coil, in particular a stainless steel coil that is per se known for instance as described in WO 2017/0645701. The membrane support 6 also serves to anchor the extractor portion 3 via the coupling 4.

In the illustrated embodiment, the coupling 4 comprises a connector 10 having a portion 10*a* that is inserted into the membrane support 6, in particular within the cylinder surrounded by the stainless steel coil in the present example. The diameter of the connector insert portion 10*a* may be configured to engage in a tight fit in an extractor end of the coil for a stable connection therebetween. The coupling 4 further comprises a fixing portion 10*b* engaging an anchor 8 of the extractor portion 3, whereby in the presently illustrated embodiment the anchor 8 is in the form of a tube, preferably a polyurethane (PU) tube fitted over the second end 10*b* of the connector 10. An adhesive 18*a* may be deposited on the connector prior to insertion of the exactor end 12*b* of the cell receiving portion, respectively coupling end 8*a* of the anchor to 8 on the connector 10. The adhesive may advantageously be in the form of a light curable adhesive for instance of the type photocurable urethane methacrylate (such as dymax 1187 M SV).

The extractor portion 3 serves to provide a means to pull out the implant from the patient's tissue at the end of its use. In the illustrated embodiment, the extractor portion further comprises a retrieval thread 9 comprising an anchor portion 15 fixed to the anchor tube 8 and a thread portion 16 extending beyond the anchor tube configured for allowing a surgical device to catch the thread to pull out the implantable capsule. In the illustrated embodiment, the retrieval thread 9 is made of a biocompatible yarn or thread, for instance of the type Polypropylene (such as the Prolene™ suture). In an embodiment, a length of the thread extends within the hollow anchor tube 8 and comprises knots 15*a*, the anchor portion 15 being held within the tube by an adhesive, for instance a light curable adhesive as described above, the knots increasing the strength of the attachment of the retrieval thread to the anchor tube. The retrieval thread is thus supple and very fine to reduce discomfort of the patient and allow easy removal of the implant.

It may be noted that the extractor portion 3 may have different shapes and configurations, the purpose being to allow a surgical device to grip on to the implant and to pull it out of the patient's tissue.

In a variant, the retrieval thread may be directly fixed to the connector 10, or be integrally formed with the connector 10, without the presence of the anchor tube. In such a variant the connector may for instance comprise an orifice allowing a thread to feed through the orifice and allow for pulling the implanted capsule out of the patient's tissue. The polyurethane tube, or any other material with the adequate mechanical and biological properties, advantageously provides a structure which supports the coupling of the retrieval thread. It may also be used as the support for the tweezers during manipulations, whether it is during the assembly or the implantation.

The cell receiving portion 2 further comprises a cell support matrix 7 inserted within the cell receiving chamber. In a preferred embodiment, the cell support matrix 7 comprises one or more yarns 14 of a biocompatible material, preferably a plurality of yarns extending longitudinally within the cell receiving chamber 13. The yarns extend, in a preferred embodiment, from a position at or proximate the extractor end 12*b* to a position at or proximate a cell loading end 12*a* of the membrane 5. The yarns preferably extend over the entire length or a large portion of the length of the cell receiving chamber 13. In a preferred embodiment, the yarns may advantageously be made of polyester (PE) of clinical grade that is per se well-known and already approved for surgical implantation uses. Such polyester yarns are typically used for sutures of tissue within a patient's body. An example of polyester yarns that may be used in advantageous embodiments of the invention is for instance 44/27-PET-5540-FTT-SS (Textile Development Associates, Inc). The material is 40 denier 27 filaments yarn made of textured polyester.

It has been found that the cell support matrix 7 significantly improves the performance of the immortalized cells contained in the cell receiving chamber increasing both activity in a release of therapeutic agents and durability over time, in particular for adherent cells. Such adherent cells are for instance genetically engineered cells useful in cell therapy such as for example genetically engineered immortalized human myoblasts, mouse myoblasts, human retinal pigment epithelial cells, stem cells, stem cell derived cell lines. whereby it is being found that these cells 24 tend to align with the fibers of the yarn 14 thus improving the density and spacing of the cells optimized for release of therapeutic agents and ingestion of nutriments. The yarns also advantageously provide a large overall surface area for adherents of cells thereto.

In an exemplary embodiment, immortalized human myoblast cells secreting GM-CSF are loaded in the cell receiving portion 2 of a capsule of the invention. Those capsules are useful in a personalized anti-tumor cell immunotherapy.

The cells are loaded in the cell receiving portion in a cell growth medium suitable for the type of cells such as Ham's F12 or DMEM supplemented with growth factors or fetal bovine serum. Further, for cells that will be frozen, a freezing medium/cryopreservant is also added to the cell growth medium, such as for glycerol.

In an exemplary embodiment, a cell receiving cavity 13 may receive therein for instance five to twenty yarns 14 arranged in parallel within the cavity extending substantially the whole length of the cavity. The yarns may be inserted within the cell receiving cavity 13 by pulling one end thereof through the cavity, the coupling 4 being mounted on the extractor end 12*b* of the cell receiving portion 2 once the membrane support 6 and cell support matrix 14 have been mounted in the porous membrane 5.

It may be noted that the cell support matrix 7 may be preassembled to the membrane support 6, for instance by inserting them through the inside of the coil prior to the insertion of the preassembled coil and cell support matrix into the tubular porous membrane 5.

The cell support matrix 7, in particular in the form of yarns 14, thus has a very beneficial effect of optimizing the distribution of cells in an orderly manner within the cell receiving chamber, improving the secretion yield and rate for a given volume. Moreover, this configuration allows the length of the cell receiving portion to be easily modified by simply changing the cut length of the yarns to the corresponding length of the porous membrane tube and coil of the membrane support 6. Moreover, the use of well characterized biocompatible implantable polyester does not adversely impact the safety of the device.

It has also been observed that the presence of the cell support matrix 7 allows the freezing and defreezing of cells contained without affecting the viability of the cells. The presence of the matrix 7 improves the freezing and defreezing properties of the capsule which is particularly advantageous since it allows the capsules to be stored for extended periods of time in a frozen state, ready for use in the treatment of a patient when needed. In particular, it would appear that the improved distribution of cells, in particular adherent cells, along the yarns contribute to maintain a high rate of viability during the freezing and thawing process.

The cells in a liquid media may be inserted into the cell receiving chamber 13 by means of a cell loading device 20 (only partially and schematically represented in the illustrations) comprising an outlet nozzle 22 that is inserted in a cell loading end 12*a* of the porous membrane 5.

The implantable capsule 1 may be supplied in a preassembled arrangement with the cell loading device. In this embodiment, the nozzle 22 of the cell loading device may be attached to the cell loading end 12*a* of the membrane, for instance by means of an adhesive 18*c*, for instance a light curable adhesive as already described hereinabove. The cell loading device may comprise a catheter tube to allow the cells in a liquid media to be injected through the catheter tube into the cell receiving chamber of the capsule, air contained within the cell receiving capsule being pushed out through the porous membrane 5.

As noted above however, the capsule may be filled with the immortalized cells and the media in a ready to use state the cell receiving end 12 being hermetically sealed by a plug (not shown) and then frozen until needed for treatment of a patient.

An implantable device of the invention can be implanted into a living subject in various sites, including under the skin (e.g. subcutaneously). Alternatively, the device may be implanted at an intrathecal, intracerebral, intraosseous, intratumoral, intrapleural, intraocular or intraperitoneal site.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

Combination

According to the invention, cells and pharmaceutical formulations thereof can be administered alone or in combination with a co-agent useful for prevention and/or treating a cancer, in particular cancer cell antigens and/or immune check-point inhibitors such as PD-1, PD-L1 or CTLA4 inhibitors or a co-agent useful for prevention and/or treating autoimmune disorders. The invention encompasses the administration of cells of the invention or a formulation thereof wherein it is administered to a subject prior to, simultaneously or sequentially with other therapeutic regimens or co-agents.

Cells of the invention or a formulation thereof according to the invention that is administered simultaneously with said co-agents can be administered in the same or different composition(s) and by the same or different route(s) of administration.

According to one embodiment, is provided a pharmaceutical formulation comprising at least one cell of the invention combined with at least one co-agent useful for prevention and/or treating a cancer and at least one pharmaceutically acceptable carrier.

Subjects

According to another aspect, the cells, devices, kits and methods of the invention are useful for the treatment of a subject in need of a treatment by a therapeutic protein.

According to a particular aspect, provides cells, devices, kits and methods of the invention are useful for the treatment of a cancer.

According to a particular aspect, a cancer is selected from Non-Hodgkin's lymphoma, head & neck cancer, melanoma, lung, bladder, renal cell carcinoma, triple negative breast cancer, colorectal, gastric, pancreas, ovarian, prostate, sarcoma and chordoma.

According to another particular aspect, provides cells, devices, kits and methods of the invention are useful for a treatment by immunotherapy.

According to another particular aspect, provides cells, devices, kits and methods of the invention are useful for a treatment of an inflammatory disorder.

According to another particular aspect, provides cells, devices, kits and methods of the invention are useful for a treatment of a neurodegenerative disorder.

According to a particular aspect, a neurodegenerative disorder is selected from Alzheimer's disease and Parkinson's disease.

According to another particular aspect, provides cells, devices, kits and methods of the invention are useful for the prevention and/or treatment of infectious diseases, in particular viral infections.

According to a particular aspect, a viral infection is COVID-19 viral infection.

According to another particular aspect, immortalized cells and methods according to the invention may be used for vaccination with tumor antigens (e.g. tumor or viral antigens) or to increase the ability of the patient's own immune system to increase the efficacy of the immune response against neoplastic cells or viral particles.

For example, cells secreting the GM-CSF immunostimulatory cytokine can be usefully used as part of personalized anti-tumor cell immunotherapy as described in Gupta & al., 2010, *Moving Forward Discov Med.,* 50:52-60.

According to a particular aspect, immortalized cells and methods according to the invention may be used for the production of other proteins (e.g. antibody or antibody fragment) modulating the intensity of the immune response and in particular the blocking of CTLA-4 protein (immune check point inhibitor) for the treatment of a cancer, in particular melanoma. For applications in the field of oncology, the following proteins may be useful to be secreted by encapsulated cells in the context of the invention: Trastuzumab (Herceptin®), Pertuzumab (Perjeta®) for breast cancers (HER2+), Rituximab (Rituxan®) for lymphomas and CML (chronic myelogenous leukemia), Blinatumomab (Biincyto®) for Acute lymphocytic leukemia (ALL), Obinutuzumab (Gazyva®), Ofatumumab (Arzerra®) for chronic lymphocytic leukemia (CLL), Cetuximab, (Erbitux®) for colon cancer and head and neck cancers, Panitumumab (Vectibix®) for colon cancer, Necitumumab (Portrazza®) for lung cancer, Bevacizumab (Avastin®) for colon cancer or relapsing brain tumours, Ramucirumab (Cyramza®) for stomach cancer, Nivolumab (Opdivo®), Pembrolizumab (Keytruda®), Atezolizumab (Tecentriqu®), Durvalumab (Imfizi®), Avelumab (Bavencio®) for advanced cancers such as melanoma, lung, head and neck, bladder and kidney cancers, Ipilimumab (Yervoy®) for melanoma and kidney cancer, Daratumumab (Darzalex®) or Elotuzumab (Empliciti®) for multiple myeloma, Dinutuximab (Unitixin®) for neuroblastoma, Olaratumab (Lartuvo®) for soft-tissue sarcomas and Catumaxomab (Removab®) for refractory ovarian cancer.

For applications in the field of inflammatory disorders, the following proteins may be useful to be secreted by encapsulated cells in the context of the invention:

Adalimumab (Humira®), Infliximab (Remicade®), Golimumab (Simponi®) for colon inflammatory disorders, rheumatoid polyarthritis, ankylosing spondylarthrites polyarthrite rhumatoide, and psoriasis, Belimumab (Benlysta®) for systemic lupus erythematosus, Tocilizumab (Actemra®), Sarilumab (Kevzara®) for rheumatoid polyarthritis or juvenile polyarthritis, Brodalumab (Siliq®), Ixekizumab (Taltz®), Secukinumab (Cosentyx®) for psoriasis, Guselkumab (Tremfya®) for psoriasis, Ustekinumab (Stelara®) for psoriasis and Crohn's disease, Vedolizumab (Entyvio®) for ulcerative colitis and Crohn's disease, Canakinumab (Ilaris®) for cryopyrin-associated periodic syndrome, Daclizumab (Zinbryta®) or Natalizumab (Tysabri®), Ocrelizumab (Ocrevus®) for multiple sclerosis, Dupilumab (Dupixent®) atopic dermatitis, Mepolizumab (Nucala®), Reslizumab (Cinqai®) and Benralizumab (Fasenra®) for asthma, Ranibizumab (Lucentis®) for macular degeneration.

For applications in other therapeutic fields, therapeutic proteins, in particular insulin or antibodies such as described in Kaplon et al, 2019, *Mabs,* 11(2):219-238.

For applications in the field of neurodegenerative disorders, the following proteins may be useful to be secreted by encapsulated cells in the context of the invention: Gantenerumab, Aducanumab, Crenezumab, Gosuranemab, Semorinemab or Zagotenemab for Alzheimer's Disease, Progressive nupranuclear palsy or Frontotemporal dementia, PRX002/RG7935 (Prasinezumab), BIM-054 (Cinpanemab) or MEDI1341/TAK-341 (AstraZeneca, Takeda Pharmaceutical Company) for Parkinson's disease or Multisystem atrophy.

According to a particular embodiment, in the field of vaccines, the following proteins may be useful to be secreted by encapsulated cells in the context of the invention.

According to a particular embodiment, antigen(s) and vaccine adjuvant(s) can be secreted by genetically engineered immortalized human myoblast cells according to the invention, wherein said cells secreting antigen(s) and cells secreting vaccine adjuvant(s) such as GM-CSF are placed in distinct implantable biocompatible devices (to be administered in the vicinity of each other) or those different secreting cells are loaded in the same implantable biocompatible devices According to another particular embodiment, immortalized human myoblast cells according to the invention can be transduced for the expression of both at least one antigen and at least one vaccine adjuvant.

According to another particular embodiment, immortalized human myoblast cells according to the invention can be transduced for the expression of several antigens (e.g. Spike protein and E protein from COVID-19) for the same pathologic agent or genetically engineered immortalized human myoblast cells according to the invention secreting several antigens for the same pathologic agent can be used concomitantly (e.g. in the same implantable device)

Methods and Uses According to the Invention

The invention provides genetically engineered immortalized human myoblast cells according to the invention for use in the prevention and/or treatment of a disorder or a disease, in particular a cancer, an inflammatory disorder or a neurodegenerative disorder.

The invention further provides the use of genetically engineered immortalized human myoblast cells according to the invention for the preparation of a pharmaceutical preparation (e.g. encapsulated cell preparation) useful the prevention and/or treatment of a disorder or a disease, in particular a cancer, an inflammatory disorder or a neurodegenerative disorder.

The invention further provides a method of preventing or treating a disorder or a disease associated in a subject, in particular a cancer, an inflammatory disorder or a neurodegenerative disorder, said method comprising administering in a subject in need thereof a therapeutically effective amount of genetically engineered immortalized human myoblast cells of the invention.

According to one aspect, the genetically engineered immortalized human myoblast cells according to the invention are useful in the treatment of a cancer (for example). For example, the genetically engineered immortalized human myoblast cells according to the invention are secreting GM-CSF.

In particular, the genetically engineered immortalized human myoblast cells according to the invention are useful in the treatment of a cancer.

According to another aspect, the genetically engineered immortalized human myoblast cells according to the invention are useful in the treatment of an inflammatory disorder (e.g. rheumatoid arthritis). For example, the genetically engineered immortalized human myoblast cells according to the invention are secreting an anti-TNF alpha antibody.

References cited herein are hereby incorporated by reference in their entirety. The invention having been described, the following examples are presented by way of illustration, and not limitation.

EXAMPLES

The following studies are conducted to support the effectiveness of cells and methods of the invention according to the invention.

The Following Abbreviations Refer Respectively to the Definitions Below:

DAPI (4,6 Diamidino-2-phenylindole); DMEM (Dulbecco's Modified Eagle Medium); DPBS (Dulbecco's phosphate-buffered saline); EDTA (ethylenediamine tetraacetic acid); FBS (Fetal Bovine serum); HBSS (Hank's Buffered Salt Solution), MEF (myocyte enhancer factor); PFA (paraformaldehyde).

Example 1: Preparation of an Immortalized Human Myoblast Cell Line

An immortalized human myoblast cell line has been prepared according to a method according to the invention as detailed below:

The following reagents were used:

Myoblast Growth Medium (GM):
- Ham's F10 (GIBCO 41550021) supplemented with 15% FBS (GIBCO 10101145)
- Bovine serum albumin (Sigma-Aldrich A4503; 0.5 mg/ml)
- Fetuin (Desert Biological 302070; 0.5 mg/ml)
- Epidermal growth factor (R&D Systems 236-GMP-200; 10 ng/ml)
- Dexamethasone (PharmaServ 8016; 0.39 μg/ml)
- Insulin (Sigma-Aldrich 19278; 0.04 mg/ml)
- Creatine monohydrate (ParmaServ 8114; 149 μg/ml)
- Pyruvate (Gibco 11360039; 100 μg/ml)
- Uridine (U3003; 50 μg/ml)
- Gentamycin (Gibco 15710049; 5 μg/ml)

Myoblast Differentiation Medium (DM):
- DMEM (GIBCO 61965026) supplemented with
- Bovine serum albumin (Sigma-Aldrich A4503; 0.5 mg/ml)
- Epidermal growth factor (R&D Systems 236-GMP-200; 10 ng/ml)
- Insulin (Sigma-Aldrich 19278; 10 μg/ml)
- Creatine monohydrate (ParmaServ 8114; 149 μg/ml)
- Pyruvate (Gibco 11360039; 100 μg/ml)
- Uridine (U3003; 50 μg/ml)
- Gentamycin (Gibco 15710049; 10 μg/ml)

Blocking Solution:
- DPBS (Sigma D8537) with
- Goat Serum (Sigma G9023, 2%)
- Tween 20 (AppliChem A1389, 0.2%)
- HBSS (GIBCO 14175053)
- PFA 4% (Santa Cruz sc-281692)
- Triton X-100 (AppliChem A1388)
- Liquid blocker (Arcus Biologicals NAN-012)
- Ab Mouse anti MF20 (Hybridoma Bank)
- Ab Rabbit anti MEF2 (Santa Cruz sc-313)
- Ab Goat anti-Mouse Alexa 488 (Life A11029)
- Ab Goat anti-Rabbit Alexa 546 (Life A11035)
- DAPI Fluoromount-G (SouthernBiotech 0100-20).

1.1 Human Myoblast Cell Source

Human myoblast cells were obtained from human muscle tissue obtained under informed consent as small muscle debris dissected during a reconstruction surgery from a non-smoking 32-year-old female donor with no significant medical history or chronic disease suffering from a left knee traumatism with anterior cruciate ligament injury. The eligibility criteria for tissue donation were defined according to the FDA guidelines "Eligibility Determination for Donors of Human Cells, Tissues, and Cellular and Tissue-Based Products (HCT/Ps)". Criteria were the following:

- Age >18 years
- Healthy subject: no identified chronic condition, including muscle disease
- Planned orthopaedic surgery
- Negative screening tests for the following infectious disease: HIV type 1 & 2, HBV, HCV, *Treponema pallidum*, HTLV 1 & 2, West Nile virus.

and the study protocol was approved by the Ethics Committee in Geneva.

1.2 Isolation of Primary Myoblast Cells and Growing Step

Under sterile conditions in cell culture hood, the human muscle tissue was rinsed with DMEM. Fat and fibrotic tissue was removed with a pincet and scissors. The tissue was placed in a petri dish with 5 ml of Trypsin EDTA 0.05% and cut into millimeter pieces with scissors. Pieces of muscle with trypsin were transferred in a sterile dissociation bottle. Volume of Trypsin EDTA 0.05% was completed to 90 ml for a maximum of 3 g of tissue. Tissue was incubated at 37° C. for 60 min under agitation. Digestion was stopped with 10% FBS. Muscle solution was then filtered through a 70 μm cell strainer and centrifuged at 1000 rpm for 5 min at room temperature (RT) to pellet the cells. After the supernatant was discarded, the pellet was dissolved into DMEM and filtered through a 40 μm cell strainer. 200,000 cells were plated per 60 mm Petri dish in 3.5 ml of growth medium (GM). Cells were incubated at 37° C. and 5% $CO_2$. Once cells reached 75% confluency, GM was removed and cells were washed with HBSS. A minimum volume of Trypsin EDTA 0.05% was applied to cover the surface of the cells and incubated for 3 min at 37° C. Reaction was stopped with the same volume of GM. Cells were collected and centrifuged at 1000 rpm for 5 min at RT. Supernatant was discarded, cells were washed with GM and centrifuged again. For cell staining, cells were resuspended in 200 μl of GM and following antibodies were added: 3 μl of anti-CD56-AlexaFluor488, 0.5 μl of anti-CD82-PE, 3 μl of anti-CD146-PECy7. After a 30-minute-incubation at 4° C., cells were washed and sorted by flow cytometry using a MoFlo Astrios EQ (Beckman Coulter). Myoblasts were defined as CD56+ CD146+ CD82+.

1.3 Myoblast Immortalization Using Lentiviral Vectors Encoding for CDK4 and hTERT (Steps b) and c))

The immortalization of the myoblast cells obtained above was achieved by the transduction of 2 genes, the cyclin-dependent kinase 4 (CDK4) and the catalytic subunit of the human telomerase (hTERT) as earlier proposed (Zhu et al., 2007, *Aging Cell,* 6, 515-523). Transgenes were cloned into a third generation pCLX lentiviral vector backbone under the expression of the human phosphoglycerate kinase (hPGK) promoter as described in Salmon, 2013, *Methods Mol Biol.;* 945:417-48. Specific viral infectivity was titrated on HeLa target cells and expressed in transducing unit per ml (TU/ml) (Barde et al., 2010, *Curr Protoc Neurosci*, Chapter 4, Unit 4 21, 10.1002/0471142301.ns0421s53).

On day 0, primary human myoblasts were seeded at 20,000 to 30,000 cells per well in a 24 wells plate in 500 μl of GM. On day 1, cells were infected with lentivirus. To achieve immortalization, a multiplicity of infection (MOI) of 3 (number of viral copies/cell) for each vector (pCLX-PGK-hTERT & pCLX-PGK-CDK4 as described herein) was applied to the cells. On day 2, 500 μl of fresh GM was added in each well. On day 3, the cells were passaged in a new culture dish.

Cells were maintained in culture under 5% $CO_2$ at 37° C. and proliferation was quantified using an automated cell counter (Countess, ThermoFischer). The number of population doublings at each passage was defined as log N/log 2, where N is the number of cells harvested at confluence divided by the number of cells initially seeded. While primary myoblast cells stopped proliferating after 45 days, cells that were transduced with lentiviruses continue growing stably for up to six months as can be seen under FIG. 1.

This confirms that transduction of primary myoblast cells with lentiviral vectors encoding CDK4 and hTERT can efficiently immortalize cells.

1.4 Myoblast Growing and Cloning (Steps d) and e))

Figure 2:
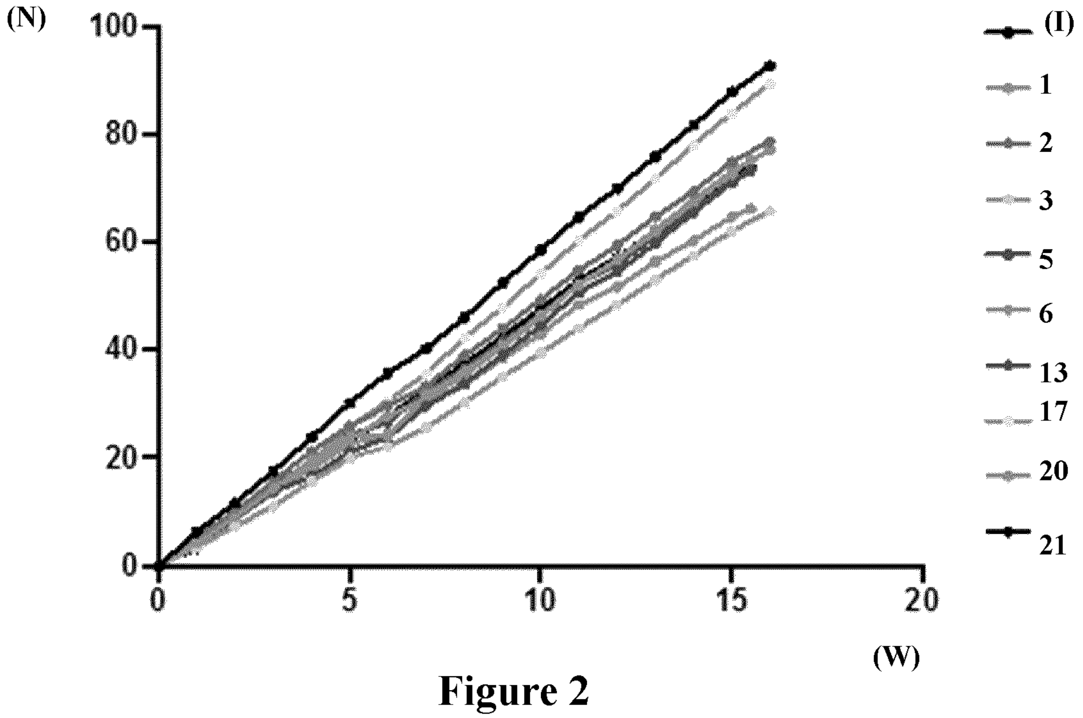
FIG. 2 represents the proliferation ability expressed as the number of cell population double (N) versus the number of weeks (W) after sorting of the clones from the immortalized human myoblast population (I) of the 9 selected clones as described in Example 1.

Once cells reached 75% confluency, cells were detached, washed and stained with anti-CD56-AlexaFluor488, anti-CD82-PE and anti-CD146-PECy7 as previously described in Laumonier et al., 2017, supra. After a 30 minutes incubation at 4° C., cells were washed and sorted by flow cytometry using a MoFlo Astrios EQ (Beckman Coulter) in a 96-well plate with one cell per well. Myoblasts were defined as CD56+ CD146+ CD82+. Individual clones were then cultured in growth medium and amplified and sorted by sorting 1 cell/well in a 96 well plate from the immortalized myoblast cell population (I) using single cell cloning. A total of 33 clones were isolated, the proliferation rate of 9 selected clones that kept qualitative morphologic features (1-3, 5-6, 13, 17 and 20-21) was quantified using automated cell counting at each passage and proved to remain stable over time as can be seen on FIG. 2.

1.5 Control of Differentiation Potential of Myoblasts into Myotubes (Step f))

To evaluate the myogenic potential of myoblast clones obtained by a method of the invention after immortalization and sorting (after step d)), the maintenance of their ability to express myogenic markers over time (triple positivity for CD56, CD82 and CD146) was quantified by flow cytometry and their preserved capacity to fuse and differentiate into myotubes was quantified as follow. Cells were plated into 35 mm culture dish in GM. When cells reached 100% confluency, GM was removed, cells were washed with HBSS, and differentiation medium was added. After 72 hours, cells were washed with DPBS twice and fixed with PFA 4% for 15 min at 4° C. After 3 washes with DPBS a circle was drawn around cells with a water repellent pen. blocking solution was applied for 30 min at RT. Primary antibodies were incubated at 4° C. overnight (mouse anti-MF20 diluted 1/1000 in blocking solution and rabbit anti-MEF diluted 1/300 in blocking solution). After 3 washes with DPBS and a 5 minutes incubation with blocking solution, secondary antibodies were incubated for 1 hour at RT (goat anti-mouse Alexa 488 diluted 1/1000 in blocking solution, goat anti-rabbit Alexa 546 diluted 1/1000 in blocking solution). After 3 washes with DPBS, coverslips were mounted with DAPI Fluoromount-G. For the quantification of differentiation percentage and fusion index, seven pictures per condition were randomly acquired at 20× on a fluorescence microscope. The number of MEF positive nuclei and DAPI nuclei was quantified.

Figure 3:
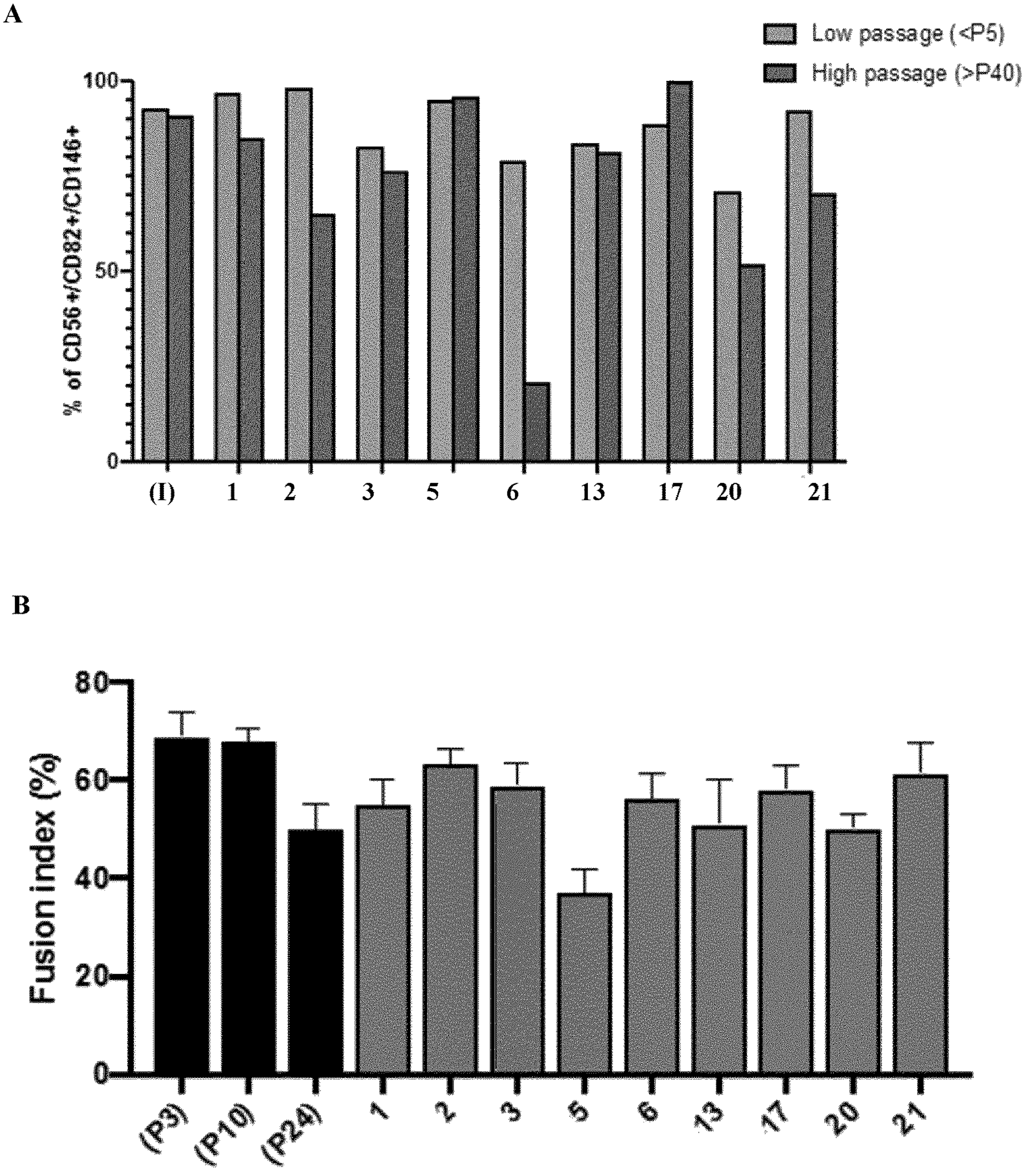
FIG. 3 shows the preserved myogenic characteristics of the clones obtained by a method of the invention after immortalization and sorting (after step d)) compared to the immortalized population as measured by the maintenance of their ability to express myogenic markers over time quantified by flow cytometry compared to immortalized cell population before sorting (I) (A) and their preserved capacity to fuse and differentiate into myotubes was quantified by immunohistochemistry (B) compared to primary cells (P3) and immortalized cell populations (P10) and (P24) after 10 and 24 passages, respectively as described in Example 1.

As can be seen on FIG. 3, the immortalized myoblast cells obtained by a method of the invention kept the myoblast phenotypic markers such as expression of myogenic markers (CD56, CD82 and CD146) and capacity to fuse and differentiate into myotubes. As can be seen, some clones demonstrated stable myogenic markers, other lost the expression suggesting lower stability and therefore, the clones presenting the best stabilities were used for further experiments. In particular, clone 61.27 deposited under number CCOS 1901 (derived from clone 2 above deposited under number CCOS 1902) was used for the encapsulation studies.

The obtained immortalized myoblast cell lines were characterized as follows in order to check their suitability for encapsulation technology:

Myoblast Encapsulation Ability

The ability of the obtained immortalized myoblast cells to be encapsulated was assayed as follows: GM was removed and 75% confluent cells were washed with HBSS. A minimum volume of TrypLE (Thermo Fisher) was added to cover the surface of the cells and incubated for 3 min at 37° C. Cells were then gently detached from the dish surface. Reaction was stopped with the same volume of HBSS. Cells were collected and counted using an automated cell counter in duplicate (Countess II device, Thermo Fisher). Cells were centrifuged at 1,000 rpm for 5 min at RT and resuspended in 25 μl GM per 800,000-1,000,000 cells. 25 μl of cell suspension was loaded in a capsule containing a hollow fiber with an inner matrix as described in FIG. 9 and Example 5 for genetically engineered immortalized myoblast cells for GM-CSF secretion. Immortalized human cells of hematopoietic origin, genetically modified to produce GM-CSF encapsulated in device as described in WO 2017/064571 (MVX-1) loaded in a capsule containing a hollow fiber as described in Lathuiliere et al., 2015, supra are used as control. The vasculon (loading tube of the capsule) was cut and the capsule was sealed using UV-sensitive adhesive (Dymax). The capsules were then placed in a 12-well plate in 2 ml of GM for 24 h before implantation.

Based on their proliferation rate and differentiation capacity, 6 clones (#1, #2, #6, #13, #17 and #21) were selected for evaluation. These clones were encapsulated and kept in culture for up to 1 month. Capsules were then fixed and processed for histological analysis. Qualitative assessment of survival was then performed and this analysis concluded to good survival properties of clones #2 and #13 based on the living cell density inside the device (presence of living cells in the middle of the device and how the cells spread inside the device) which were then selected for genetic engineering for expression of GM-CSF as detailed below.

Myoblast Cell Culture in Hypoxic Conditions

The behaviour of the obtained immortalized myoblast cells in hypoxic conditions was tested as follows: Cells were plated and cultured in standard conditions for 24 hours to allow for cell adhesion. Culture dishes were then placed in a hypoxic incubator chamber at 37° C. with 1% oxygen for 24 hours. When recombinant protein needed to be quantified in culture medium, fresh medium that was pre-incubated for 24 hours in hypoxic chamber was added to the cells for two hours before quantification.

Example 2: Alternative Method of Sorting the Immortalized Human Myoblast Cells Under Step d)

Alternatively, in a method of establishing an immortalized human myoblast cell line according to the invention, the isolation of immortalized human myoblast cell clones under steps c) and d) can be performed on encapsulated myoblast cell population according to steps c1) c4).

Immortalized myoblast cell population obtained under 1.3 were encapsulated into an implantable device with an inner matrix as described on FIG. 9.

The device were implanted in mouse subcutaneous tissue for 3 weeks. After 3 weeks, devices were retrieved and placed in culture medium. Capsules were sectioned and their content (cells and matrix) was disseminated in culture medium in a dish. Cells were kept in culture for several weeks for expansion. Cells were then detached and stained for the FACS sorting of human myoblast (defined as CD56+ CD146+ CD82+). Individual human myoblast clones were isolated from this myoblast population.

The myogenic potential (differentiation into myotubes) of 3 of these clones appeared unaffected. The proliferation rate of these clones was also monitored for several weeks and was a doubling time of about 24 to about 72 hours for at least 6 months.

Example 3: Preparation of Genetically Modified Immortalized Human Myoblast Cell Line Immortalized human myoblast cell lines obtained by a method of the invention are useful for the preparation of genetically modified cells for the production of proteins of interest, in particular for their protein secretion within a capsule.

3.1 Myoblast Transduction for the Secretion of Recombinant GM-CSF (Step ii))

For the expression of human or murine GM-CSF, human or murine GM-CSF cDNA was cloned into the pCLX lentiviral vector under the expression of the human PGK promoter as described in Salmon, 2013, supra.

The human PGK promoter contains hypoxia response element which are enhancers that upregulate the gene expression in hypoxic conditions (Firth et al., 1994, *Proc. Natl. Acad. Sci. U.S.A.,* 91, 6496-6500). To confirm this, primary myoblast cells with lentiviral vectors encoding for the GFP (MOI=5) under the expression of phosphoglycerate kinase (PGK) or ubiquitin (UBI) promoters and after 36 h in 1% oxygen, cells were fixed and fluorescence was quantified by flow cytometry and it was observed that in myoblast cells, PGK promoter drives a stronger expression as compared to UBI and that myoblast cells upregulate the expression of GFP in hypoxic condition when driven by the PGK promoter as opposed to UBI promoter.

For this reason, the PGK promoter was used in the genetic engineering of immortalized human myoblasts of the invention since the secretion of target proteins might be enhanced when myoblast cells are encapsulated. Therefore, Clones #2 and #13 obtained in Example 1 were transduced with different concentration of the above lentivirus and different MOI (3-100) were applied to the cells.

The recombinant protein secretion ability by genetically modified immortalized human myoblasts was quantified as follows:

Cells were seeded in a T75 cell culture flask. Once 75% confluency was reached, cells were washed with HBSS and 5 ml fresh growth medium was added for 2 hours at 37° C. Medium was then collected for GM-CSF quantification and cells were counted using an automated cell counter (Countess II device, Thermo Fisher). Different ELISA kits were used depending on the protein to be quantified (GM-CSF Human ELISA Kit #KHC2011, GM-CSF Mouse ELISA Kit #BMS612, IgG (Total) Human ELISA Kit #BMS2091, Thermo Fisher). Protocols were applied according to manufacturer instructions. Results were reported in pg/cell/day. As shown under FIG. 4A, expression of GM-CSF was obtained from the genetically immortalized human myoblasts of the invention.

Figure 4:
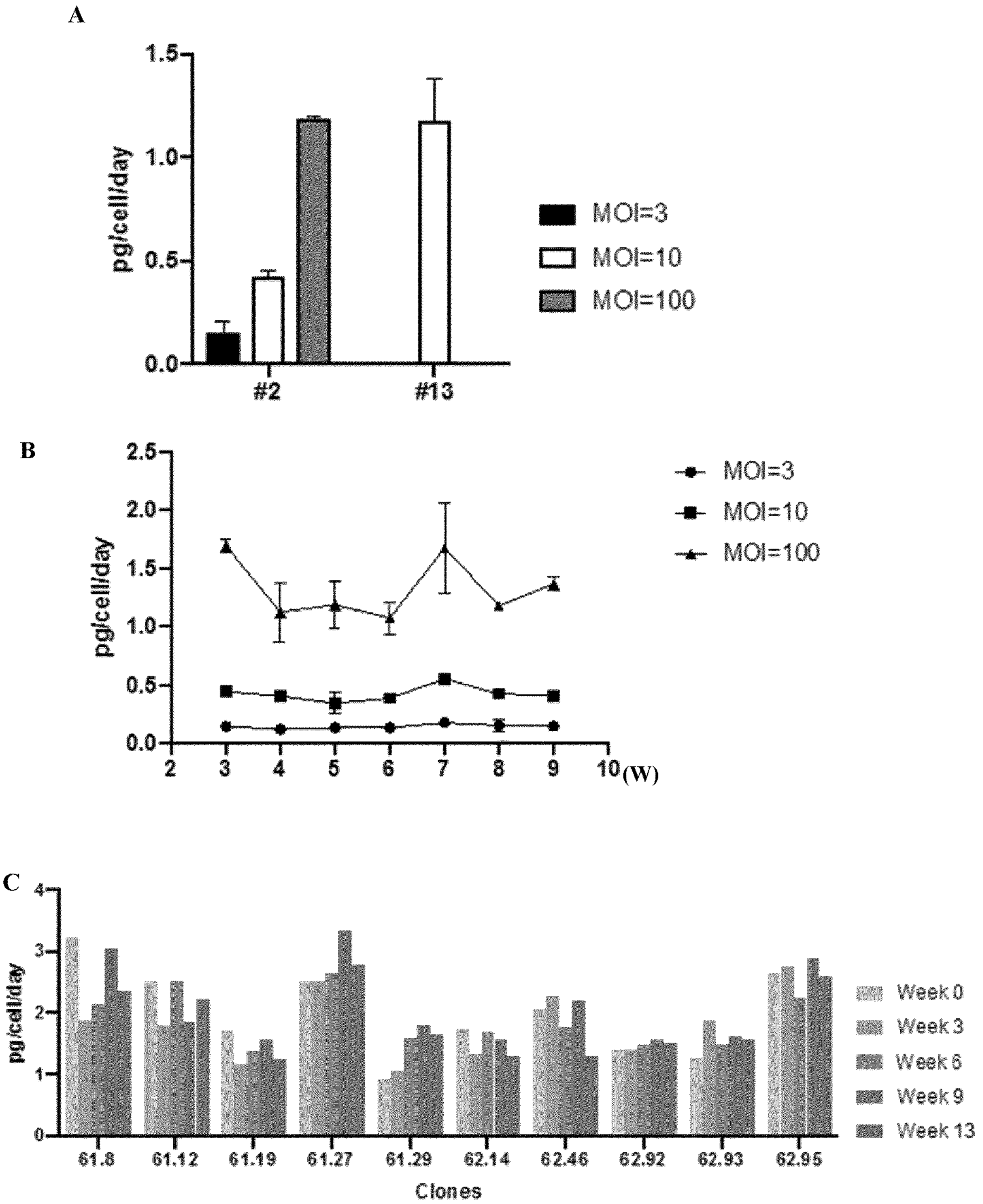
FIG. 4 shows GM-CSF secretion rate as measured by ELISA achieved by genetically modified immortalized human myoblast cells of the invention (clone 2) right after transduction (A), versus the number of weeks (W) after transduction for clone 2 (B) and for various clones after sorting step (iv) of the method for different weeks after transduction (C), as described in Example 3.

The secretion of GM-CSF from cell populations generated from transduced immortalized clone #2 was monitored weekly for nine weeks and it was confirmed that transduction with lentiviral vector is efficient to produce highly stable GM-CSF-secreting cell lines as shown under FIG. 4B.

3.2 Isolation of Human GM-CSF-Secreting Clones (Steps iii) and iv))

Figure 5:
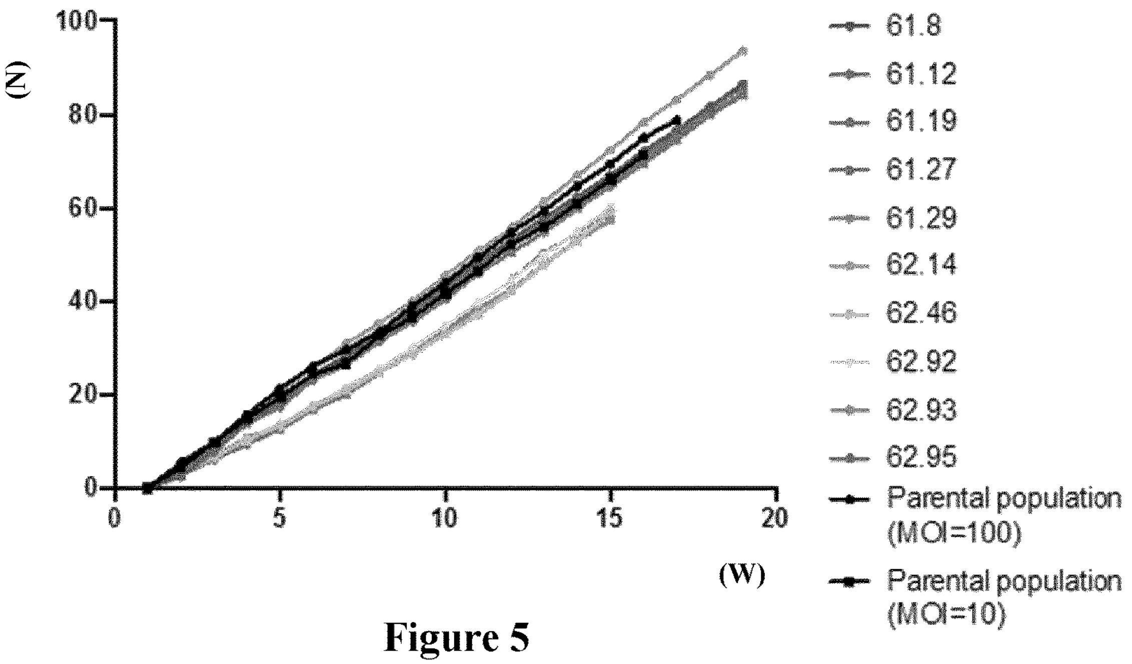
FIG. 5 shows the proliferation ability expressed as the number of cell population double (N) versus the number of weeks (W) after sorting of the clones from the genetically modified immortalized human myoblast population of the 10 selected clones as described in Example 3.

From two GM-CSF expressing populations (Clones #2.100 & #13.10, 125 individual clones were sorted and expression of GM-CSF was measured for every clone. The 10 clones that secreted the highest levels of GM-CSF in a range of about 1-4 pg/cell/day for each population were monitored for their secretion of GM-CSF for several weeks (FIG. 4C) and their proliferation (FIG. 5A). Those data support that the secretion and proliferation rates of GM-CSF secreting clones remained stable over time.

Figure 6:
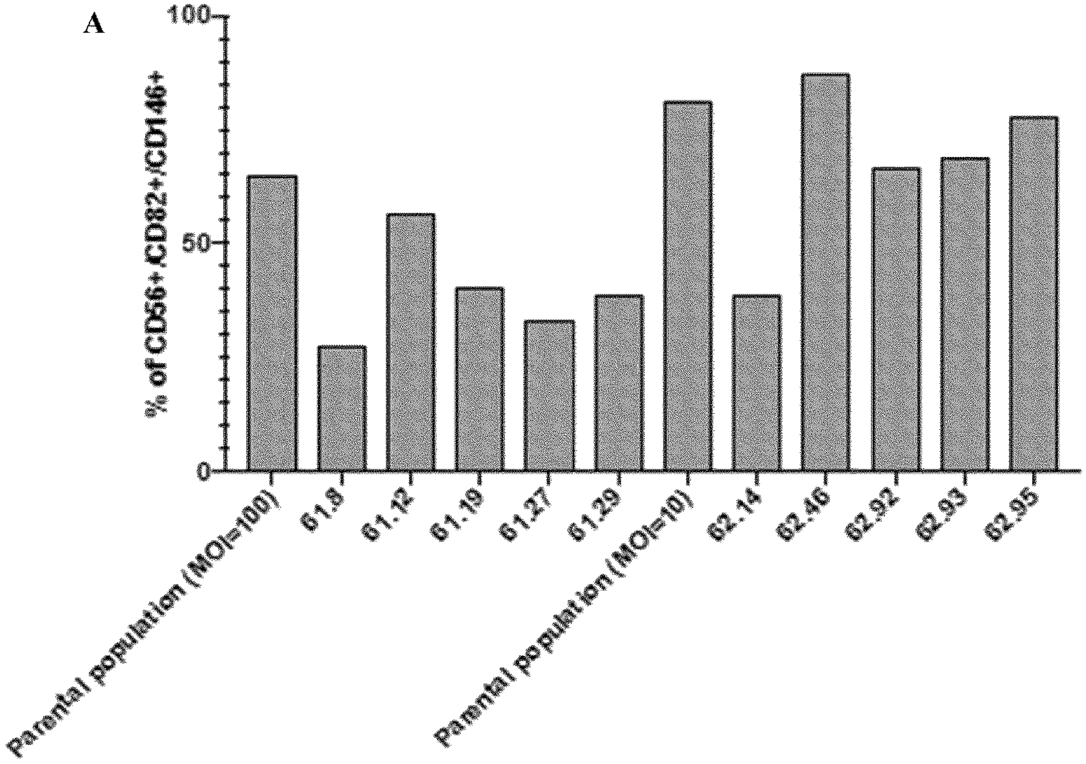
FIG. 6 shows the preserved myogenic characteristics of the clones obtained by a method of the invention after sorting (after step iv)) as measured by the maintenance of their ability to express myogenic markers over time quantified by flow cytometry (A) and their preserved capacity to fuse and differentiate into myotubes was quantified by immunohistochemistry (B) compared to the parental populations (MOI=10 and 100) as described in Example 2.
Figure 6:
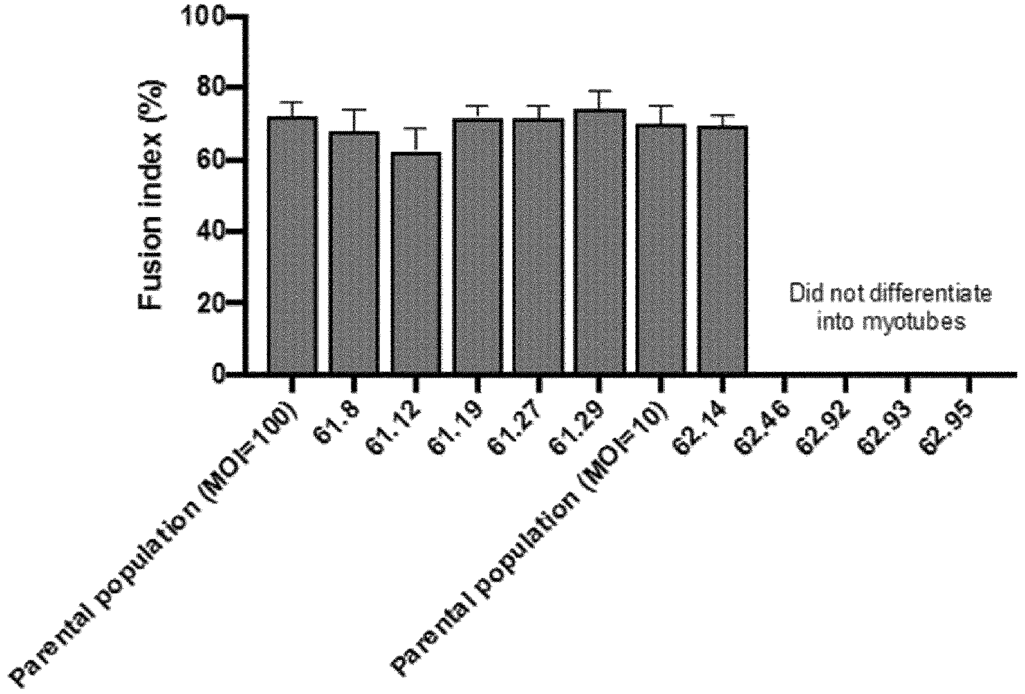

The stability of the expression of myogenic markers over time (triple positivity for CD56, CD82 and CD146) for the isolated GM-CSF-secreting myoblast cell clones and their capacity to fuse and differentiate into myotubes was assessed as detailed above and confirmed as shown under FIG. 6.

The obtained genetically modified immortalized myoblasts were characterized as follows in order to check their suitability for encapsulation technology:

Myoblast Encapsulation Ability

The ability of the obtained immortalized myoblast cells to be encapsulated was assayed as described above for six clones selected based on their GM-CSF secretion level, growth rate and myogenic characteristics, i.e. the myogenic marker expression and the ability to differentiate into myotubes were encapsulated and then tested in vivo (mouse subcutaneous tissue).

Implantation of Hollow Fiber Encapsulation Device in Mice

All experiments on mice were done according to the Swiss regulation for the care and use of laboratory animals. Animals were bred and maintained in a specific pathogen free environment and had access to water and food ad libitum. Adult Rag2/Il2rg double knockout mice (Shinkai, 1992, *Cell*, 6; 68(5):855-67) were anesthetized with isoflurane and capsules were implanted in the subcutaneous tissue using a trocar. Wound was closed with surgical staples and animals recovered in their home cage. Analgesia was provided by the subcutaneous injection of buprenorphine 0.1 mg/kg, 20 minutes before anaesthesia and acetaminophen 2 mg/ml in drinking water for three days. At the end of experiment, mice were sacrificed with a lethal injection of sodium pentobarbital. Devices were dissected and either fixed directly to perform histological analysis or placed back in culture medium for further quantification of recombinant protein expression. Histological processing was performed as previously described (Schwenter et al., 2011, *Cancer Gene Ther.*, 18, 553-562).

The GM-CSF secretion level was measured from capsules before implantation and after explantation (at one and 3 weeks). GM-CSF was also measured in the mouse serum. Histological analysis was also performed on capsules after explantation to qualitatively measure cell survival. This experiment was performed using an encapsulation device with an inner matrix as described in Example 5 and FIG. 9. The secretion levels were compared with those obtained with immortalized human cells of hematopoietic origin, genetically modified to produce GM-CSF encapsulated in device as described in WO 2017/064571 (MVX-1) and currently used in the current clinical trial no NCT02193503 (phase I) NCT02999646 (phase II in HNSCC).

Figure 7:
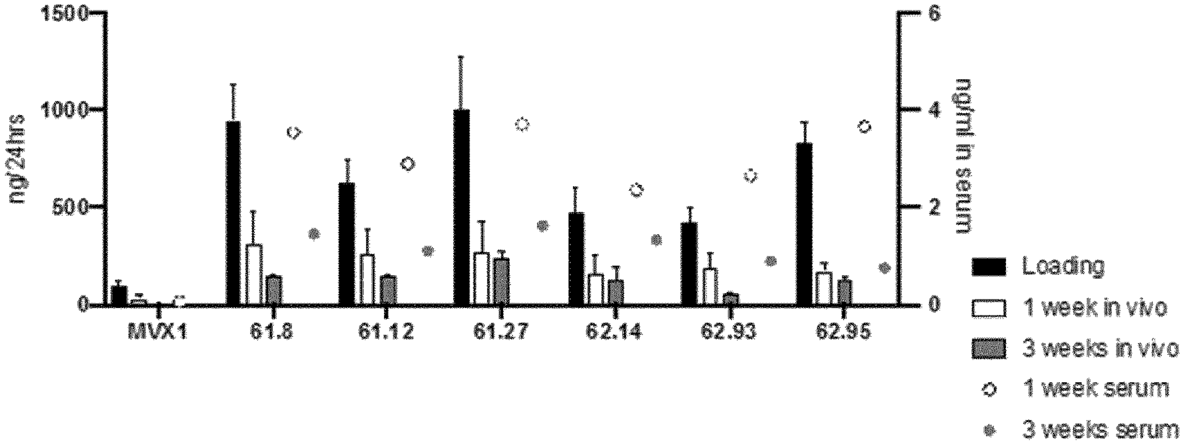
FIG. 7 shows the GM-CSF secretion rate as measured by ELISA achieved by various encapsulated selected clones for different weeks after in vivo transplantation as compared to control encapsulated cells (MVX-1), as described in Example 3.

As it can be seen on FIG. 7, all encapsulated clones presented much higher secretion levels than the MVX-1 cells, therefore confirming the advantageous effects of the immortalized cells of the invention, in particular for use in encapsulation therapy.

Figure 8:
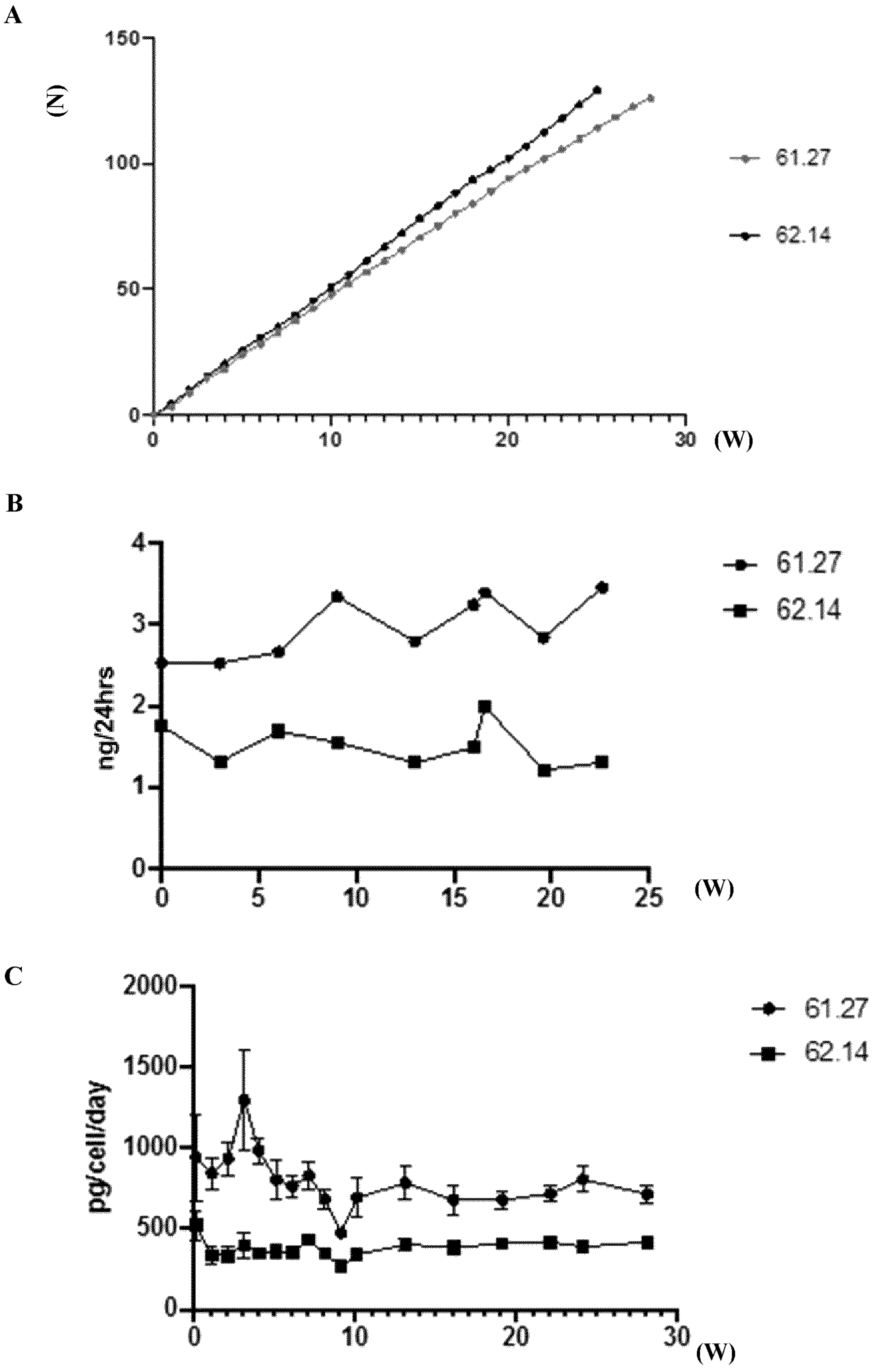
FIG. 8 shows the stability over time of two selected clones 61.27 and 62.14 in terms of in vitro proliferation rate as non-encapsulated cells (A) expressed as the number of cell population double (N) versus the number of weeks (W) after sorting of the clones from the genetically modified immortalized human myoblast population, in vitro secretion rate as non-encapsulated cells versus weeks (W) after sorting (B) and in vitro secretion rate as encapsulated cells versus weeks (W) after encapsulation (C) and in vivo secretion rate in mice as encapsulated cells measured by quantification of GM-CSF in serum compared before implantation (D) and in tissue surrounding the capsule (E), compared to control encapsulated cells (MVX-1), as described in Example 3.
Figure 8:
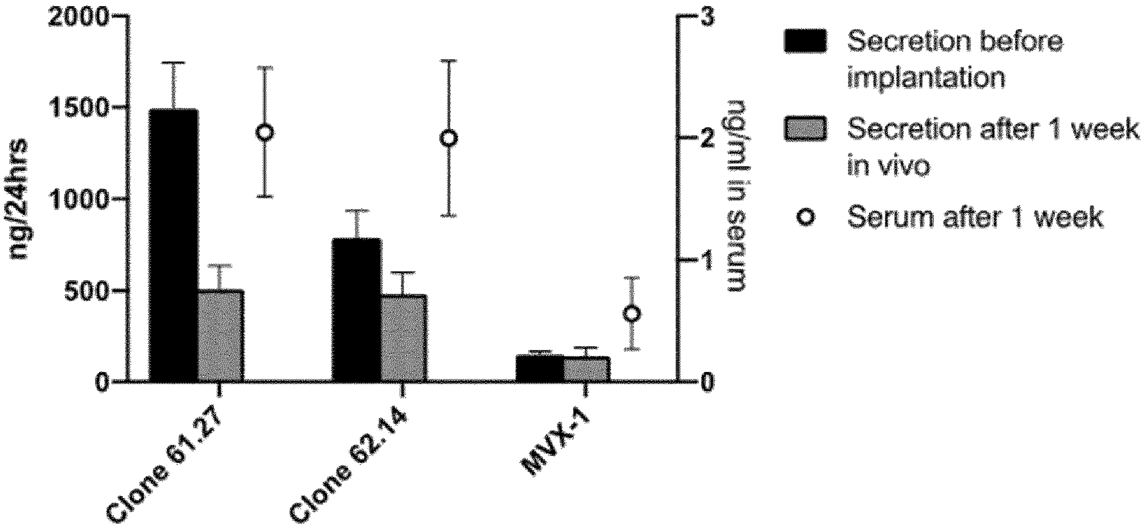
Figure 8:
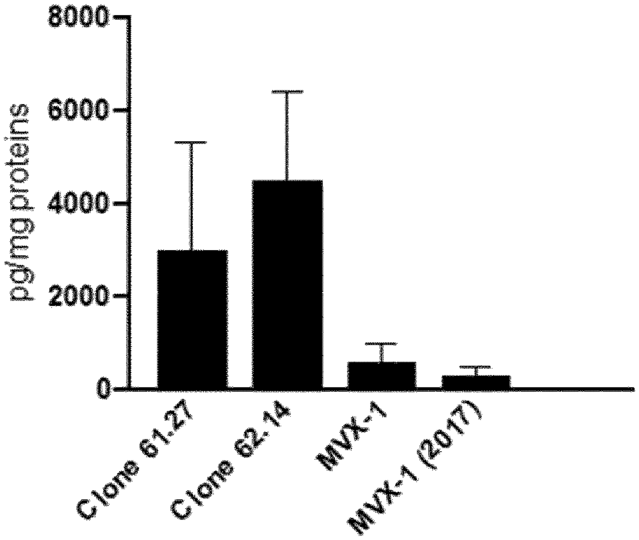

Then, Clone #61.27 deposited under number CCOS1901 (derived from clone 2 above deposited under number 1902) was selected based on his high secretion rate (about 3 pg/cell/day) and highest serum level of GM-CSF (suggesting high delivery of GMC-SF by 61.27 clone) and clone #62.14 was selected because GM-CSF delivery remained stable over time, suggesting high cell survival rate. The proliferation rate of these two clones was monitored in vitro for 6 months and the GM-CSF secretion rate was also monitored in vitro for several months as non-encapsulated and encapsulated cells as described in FIG. 8. FIG. 8 shows the stability over time of clones 61.27 and 62.14 in terms of in vitro proliferation rate as non-encapsulated cells (A) expressed as the number of cell population double (N) versus the number of weeks (W) after sorting of the clones from the genetically modified immortalized human myoblast population, in vitro secretion rate as non-encapsulated cells versus weeks (W) after sorting (B) and in vitro secretion rate as encapsulated cells versus weeks (W) after encapsulation (C) and in vivo secretion rate in mice as encapsulated cells measured by quantification of GM-CSF in serum compared before implantation (D) and in tissue surrounding the capsule (E), compared to control encapsulated cells (MVX-1), as described in Example 3.

Encapsulation device as described in Example 5 and shown in FIG. 9 were loaded with those clones and secretion of GM-CSF was monitored for several months in vitro as described above compared to encapsulated cells (MVX-1) as defined above.

Freezing and Thawing of Encapsulation Devices Pre-Loaded with Human Myoblasts

The impact of different freezing conditions on the GM-CSF expression level after thawing was tested. Capsules were loaded with genetically modified GM-CSF secretion immortalized myoblast cells described (clones 61.27 and 62.14 in freezing medium that contained different concentration of glycerol (used as a cryopreservant). Before freezing, loaded capsules were suspended and incubated for variable periods of time in freezing medium. For freezing, capsules were placed in silicone tubes that were prefilled with freezing medium and transferred into cryotubes. Cryotubes were quickly transferred into CoolCell freezing container (Biocision) and placed at −80° C. overnight before being transferred into liquid nitrogen for long term storage. For thawing, the frozen capsule in silicone tube was transferred into pre-warmed GM in a 10-cm petri dish. After gentle agitation, the capsule was removed from the silicone tube and placed in 12-well culture plate containing GM.

Figure 10:
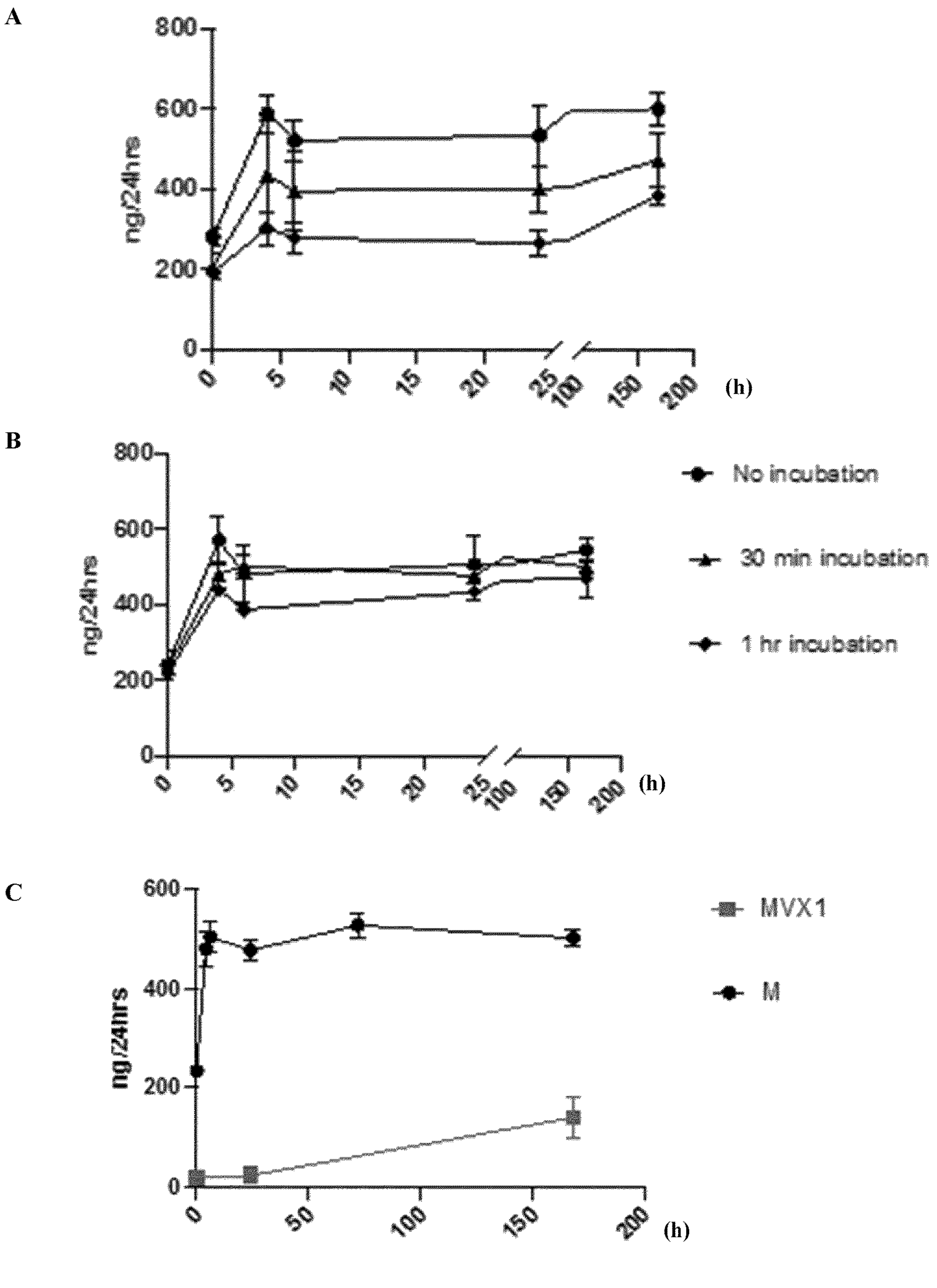
FIG. 10 shows GM-CSF secretion rate as measured by ELISA achieved by frozen encapsulated genetically modified immortalized human myoblast cells (M) of the invention versus time after thawing (in hours) formulated in 5% (A) and 10% (B and C) glycerol as freezing medium with different time of incubation with the freezing medium and compared to control encapsulated cells (MVX-1), as described in Example 3.

As can be seen on FIG. 10, GM-CSF secreting myoblast cells of the invention performed much better than control cell line (MVX1) after freezing glycerol (FIG. 10C). The use of 10% glycerol (FIGS. 10B and C) as a freezing medium and an incubation time of 0 to 30 minute of the cells with the freezing medium before freezing was well tolerated.

Example 4: Diversity of Possible Genetically Modified Immortalized Human Myoblast Cell Line to Produce Therapeutic Proteins The ability of immortalized myoblast cells according to the invention to be genetically engineered for the expression of complex molecules of therapeutic interest such as antibodies.

Therapeutic Macromolecules

Myoblast Transduction for the Secretion of Recombinant Anti-Human CD20 IgG (Step ii))

For the expression of an anti-human CD20 IgG, the variable region of the rituximab heavy chain was inserted in a human IgG1 heavy chain backbone and the variable region of the rituximab light chain was inserted in a human kappa light chain backbone. The two sequences were synthetized and cloned and into a 3rd generation pLV-hPGK-WPRE lentiviral vectors (Vectorbuilder) as described in SEQ ID NO: 6 and 7. Cells were infected with the heavy and light chain vectors using same MOI for both transgenes as described in Lathuilière, 2016, *Methods Mol Biol.,* 1448: 139-155.

Figure 11:
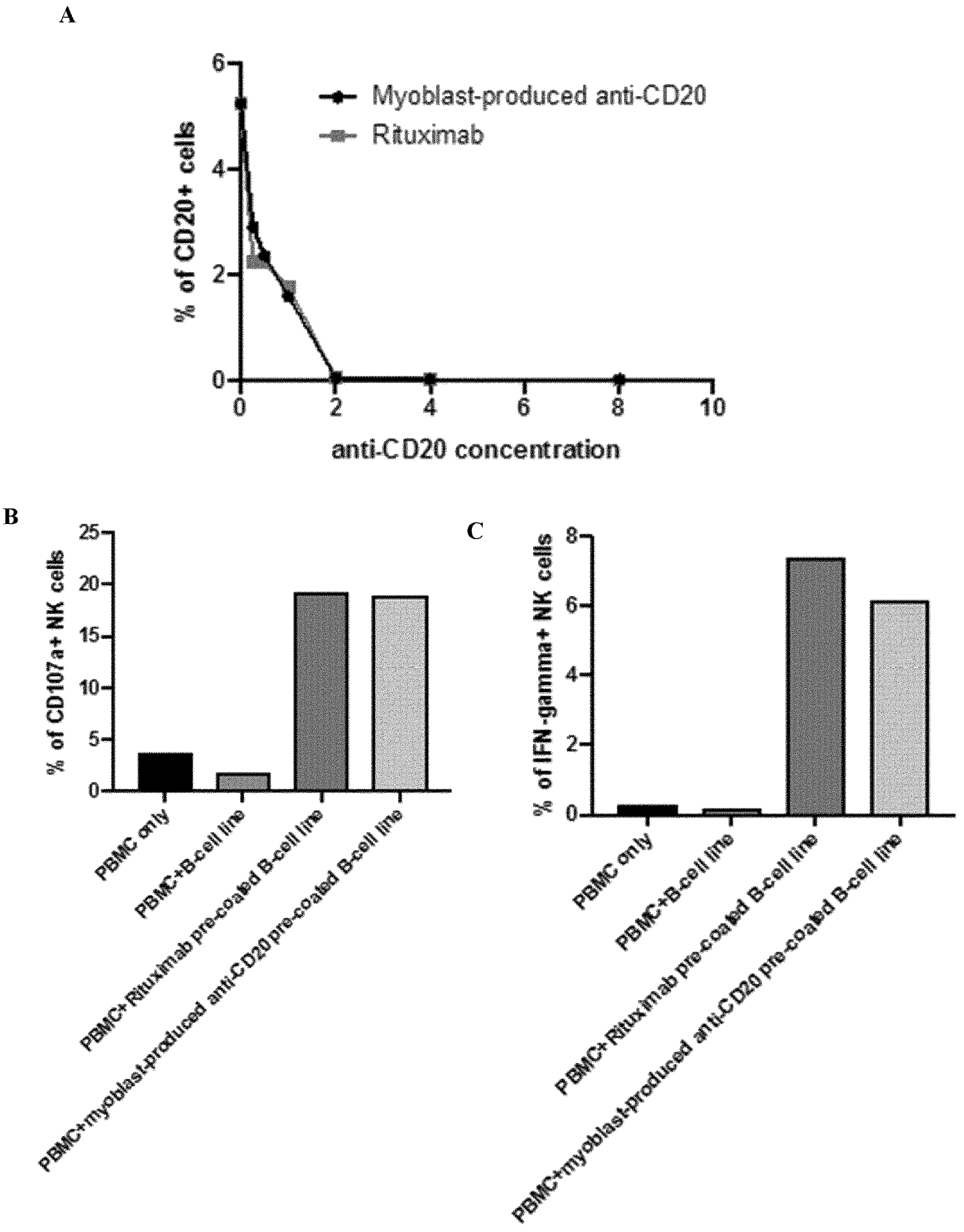
FIG. 11 supports the ability of immortalized myoblast cells obtained under Example 1 from clone 2 transduced with lentiviral vectors encoding for the heavy and light chain of rituximab to produce biologically active monoclonal antibody as described in Example 4. A: IgG secreted by genetically modified cells of the invention and commercial Rituximab behave identically when incubated with a fluorescent tagged anti-CD20 antibody; B & C: myoblast-produced IgG was as efficient in a degranulation assay that tested the induction of a cytotoxic response (overexpression of IFN-gamma (B) or CD107a(C)) after a B-cell line was exposed to either Rituximab or myoblast-produced anti-CD20.

Immortalized myoblast cells obtained under Example 1 from clone 2 were transduced with lentiviral vectors encoding for the heavy and light chain of rituximab, a commercialized therapeutic anti-CD20 monoclonal antibody using methods already described (Lathuiliere et al., 2016, supra) with different dose of lentivirus (MOI) as described in Example 2. The secretion of IgG was then quantified in culture medium and the functionality of the secreted anti-CD20 IgG was demonstrated by flow cytometry. In a competition assay, human PBMC (peripheral blood mononuclear cell) were pre incubated with different concentration of either the myoblast-produced anti-CD20 IgG or commercial Rituximab and then incubated with a fluorescent tagged anti-CD20 antibody. Those experiments supported that the produced IgG behaved exactly like Rituximab in this assay as shown on FIG. 11A. Moreover, the myoblast-produced IgG was as efficient in a degranulation assay that tested the induction of a cytotoxic response (overexpression of IFN-gamma or CD107a) after a B-cell line was exposed to either Rituximab or myoblast-produced anti-CD20 as shown on FIGS. 11B and 11C.

The obtained Anti-CD20 IgG secreting myoblasts were then loaded into an implantable device as described in Example 5 and under FIG. 9 (two cell populations tested CD20.30 & CD20.100, $10^6$ cells/device) and implanted in the mouse subcutaneous tissue. Before implantation, secretion of IgG from capsules is quantified in culture medium. Anti-CD20 IgG plasma level from living animals is then quantified every two weeks.

Myoblast Transduction for the Secretion of Anti-CTLA4 IgG

For the expression of an anti-human CTLA4 IgG, the variable region of the ipilimumab heavy chain (WO 200/1014424) was inserted in a human IgG1 heavy chain backbone and the variable region of the ipilimumab light chain (WO 2001/014424) was inserted in a human kappa light chain backbone. The two sequences were synthetized and cloned and into a 3rd generation pLV-hPGK-WPRE lentiviral vectors (Vectorbuilder) as described in SEQ ID NO: 2 and 3. Cells were infected with the heavy and light chain vectors using same MOI for both transgenes as described in Lathuilière, 2016, *Methods Mol Biol.,* 1448:139-155.

Figure 13:
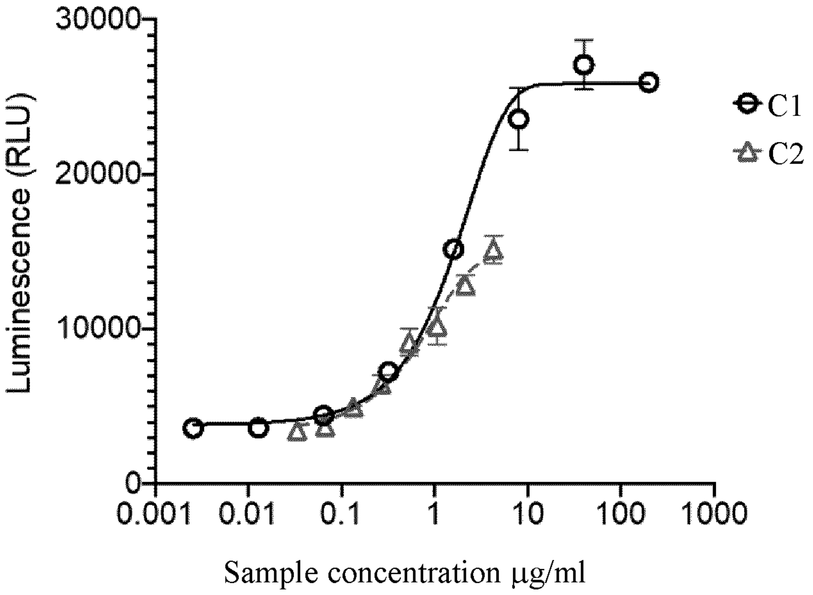
FIG. 13 represents the bioactivity of a monoclonal antibody produced by immortalized myoblast cells according to the invention (Myoblast cells were transduced for the expression of a monoclonal human IgG directed against human CTLA4: C2) in a CTLA-4 Blockade Reporter Gene Assay and compared to ipilimumab (Yervoy™, Bristol-Myers Squibb SA) biosimilar as a positive control (C1), as described in Example 3.

Immortalized myoblast cells obtained under Example 1 from clone 2 were transduced with lentiviral vectors encoding for the heavy and light chain of ipilimumab, a commercialized therapeutic anti-CTLA4 monoclonal antibody using methods already described (Lathuiliere et al., 2016, supra) with different dose of lentivirus (MOI) as described in Example 2. The secretion of IgG was then quantified in culture medium by ELISA and the bioactivity of the secreted anti-CTLA4 IgG was demonstrated in a CTLA-4 Blockade Bioassay as shown on FIG. 13: aAPC/Raji Cells and CTLA-4 Effector Cells were antigen presenting cells and effector cells respectively in this study. CTLA-4 effector cells were Jurkat T cells expressing human CTLA-4 and luciferase reporter gene whose expression was regulated by NFAT-RE upstream. aAPC/Raji cells were Raji cells expressing endogenous CD80/CD86 and a cell surface protein capable of activating TCR.

When positive control or secreted anti-CTLA4 were added, they could block the interaction between CTLA-4 and CD80/CD86 and the immunosuppression was lifted, thereby activating T cells and activating NFAT-induced luciferase expression. The blockade activity of the anti-CTLA-4 antibody was evaluated in term of luciferase activity. As shown on FIG. 13, the myoblast-produced antibody expressed by genetically engineered immortalized human myoblasts according to the invention was compared to ipilimumab biosimilar as a positive control. The assay demonstrated that myoblast-produced anti-CTLA4 showed significant blockade activity against the interaction between CTLA-4 and CD80/CD86. $EC_{50}$ was equivalent to positive control (Yervoy™, Bristol-Myers Squibb SA), namely 1.519 compared to 1.573 for the control.

Myoblast Transduction for the Secretion of Anti-Amyloid Beta (Gantenerumab)

For the expression of an anti-human amyloid beta IgG, the variable region of the gantenerumab heavy chain (EP 1960428) was inserted in a human IgG1 heavy chain backbone and the variable region of the gantenerumab light chain (EP 1960428) was inserted in a human kappa light chain backbone. The two sequences were synthetized and cloned and into a 3rd generation pLV-hPGK-WPRE lentiviral vectors (Vectorbuilder) as described in SEQ ID NO: 3 and 4. Cells were infected with the heavy and light chain vectors using same MOI for both transgenes as described in Lathuilière, 2016, supra.

Figure 14:
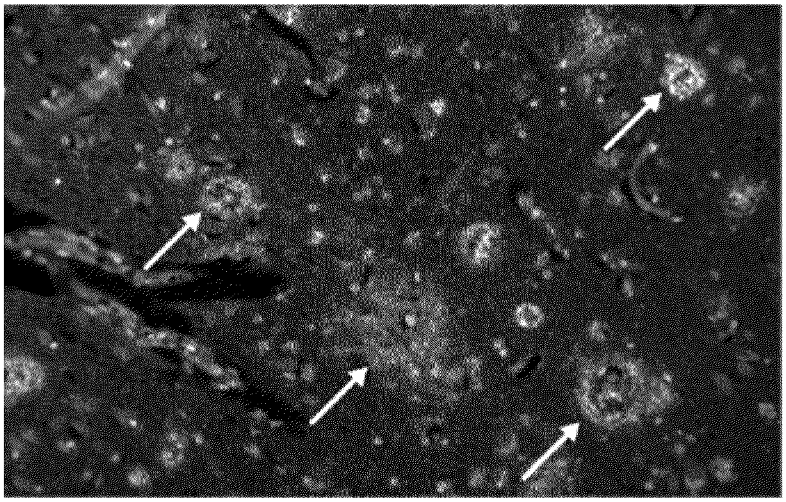
FIG. 14 represents an immunohistochemistry on an Alzheimer's disease brain section with an anti-amyloid beta monoclonal antibody produced by immortalized myoblasts, as described in Example 4.

Immortalized myoblast cells obtained under Example 1 from clone 2 were then transduced with lentiviral vectors encoding for the heavy and light chain of gantenerumab prepared as described above, a phase III investigational therapeutic anti-amyloid beta monoclonal antibody using methods already described (Lathuiliere et al., 2016, supra) with different doses of lentivirus (MOI) as described in Example 2. The secretion of IgG was then quantified in culture medium by ELISA. The functionality of the antibody was tested by performing an immunohistochemistry on brain sections coming for a human Alzheimer's disease case. Briefly, sections were deparaffinized, antigen retrieval was performed in citrate buffer, sections were incubated with the supernatant of transduced human myoblasts overnight at 4° C. After washes in PBS, secondary antibody was incubated for 2 hours at room temperature. Sections were washed and images were acquired microscope. Positive staining was observed on sections, suggesting that secreted antibody was functional (arrows, FIG. 14).

Xenogenic Proteins

In order to test the ability of the immortalized human myoblast cells of the invention to be genetically engineered to produce proteins from a different species, an immortalized myoblast clone obtained under Example 1 was transduced with different doses (MOI) of lentiviral vector encoding for the murine GM-CSF (mu-GM-CSF) protein. Individual mu-GM-CSF-secreting clones were then isolated from the transduced populations and one clone was selected and encapsulated into an implantable as described in Example 5 and under FIG. 9 ($10^6$ cells/device). Delivery of muGM-CSF was quantified for several weeks in vitro.

The biological activity of the secreted muGM-CSF was confirmed by in vivo experiments in which a massive cellular immune response was detected around subcutaneously implanted encapsulation devices. The muGM-CSF secretion level was measured before implantation and after explantation at different timepoints (after 1, 3, 5 and 7 days). Some capsules were kept in vitro during the experiment as a comparator. A decrease in secretion level was observed, which is consistent with previous findings and the massive immune infiltrate produced by GM-CSF biological activity affects encapsulated cell survival. The influx of inflammatory cells may decrease oxygen and nutrient diffusion toward encapsulated cells.

All those data support that immortalized human myoblast cells of the invention present exceptional long term survival, while keeping myoblast features >100 days, even in encapsulated environment. Those immortalized human myoblast cells can be genetically engineered to produce high level of protein of interest (such as antibodies, antibody fragments, growth factors, cytokines etc.) in an encapsulated environment where they can proliferate. Finally those cells, once encapsulated, can be straightforwardly frozen after loading and thawed later on which is an important feature that will be very convenient for future clinical applications.

Example 5: Comparing Behavior of Immortalized Cells on the Invention in Different Devices In the following experiments, two types of implantable capsules are compared: a capsule as described in FIG. 9 for Groups A and B, vs a capsule as described in WO 2017/064571 (conventional capsule) for comparative Group C.

Group A: capsules are loaded with cells of the invention (immortalized human myoblast cell line expressing human GM-CSF (cell line deposited under number CCOS1901)

Group B: capsules are loaded with a control cell line: K562 human erythroleukemia cells expressing human GM-CSF Group C: capsules are loaded with the same control cell line: K562 human erythroleukemia cells expressing human GM-CSF.

The conventional capsule does not enclose any supporting matrix, therefore it is not suited to be loaded with adherent cells such as human myoblast. To compare the efficacy of the two distinct capsules to produce huGM-CSF over time, the K562 human erythroleukemia cell line expressing human GM-CSF was used as an alternative cell line for producing the protein of interest. Group B and C provide a direct comparison of the performance of the two capsules as two distinct capsules contain the same genetically engineered cell line expressing the same therapeutic protein of interest according to the invention.

Figure 12:
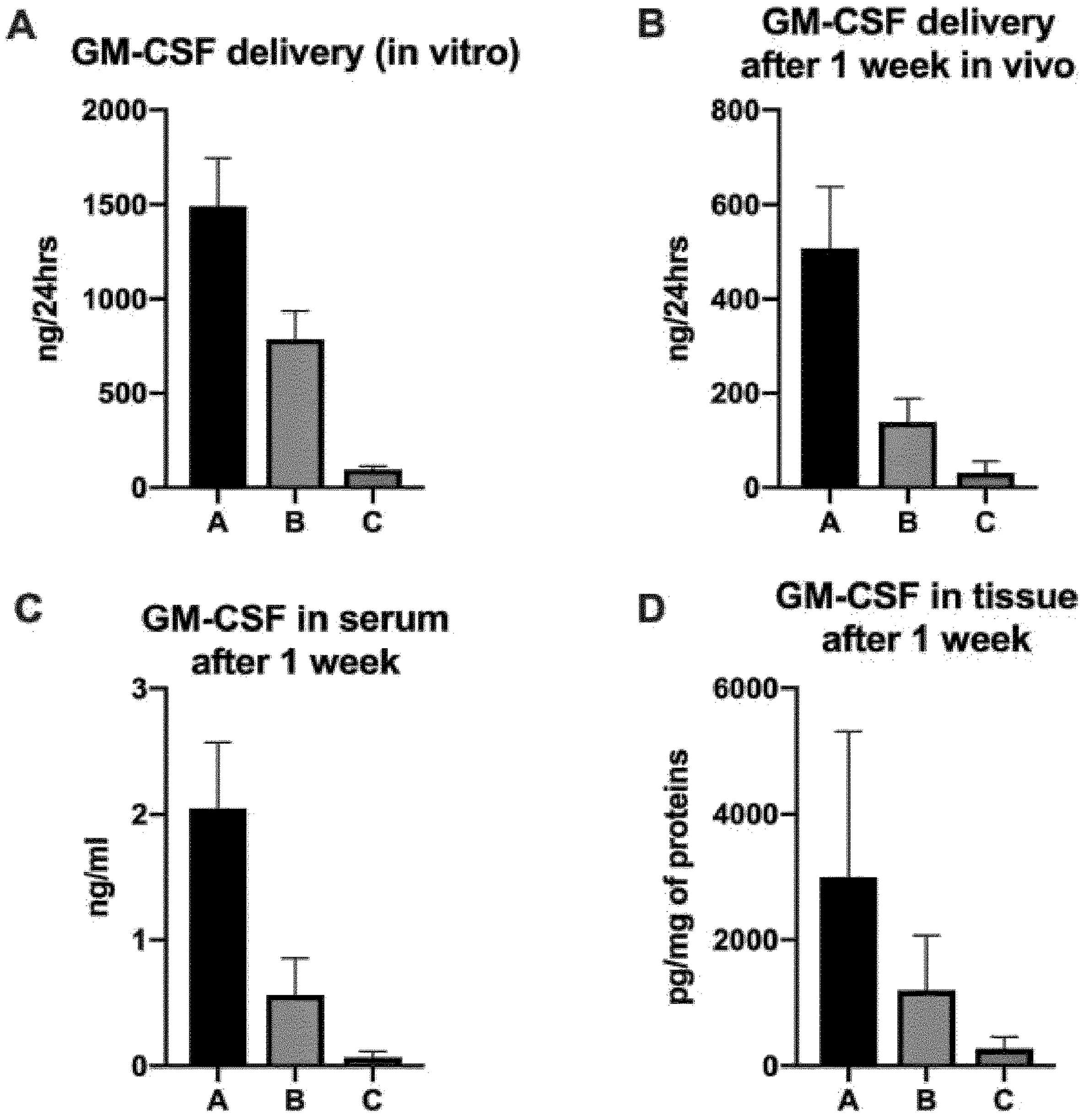
FIG. 12 compares the release of huGM-CSF from two distinct capsules and two types of cells as described in Example 5. A: GM-CSF release in vitro in the capsule supernatant for Group A: a capsule according to an embodiment of the invention (illustrated in FIG. 9) containing genetically modified immortalized human myoblast cells secreting the same therapeutic protein GM-CSF, Group B: a control cell line being K562 human erythroleukemia cells expressing human GM-CSF loaded in the same capsule according to an embodiment of the invention (illustrated in FIG. 9) and Group C: a conventional capsule containing the same control cell line being K562 human erythroleukemia cells expressing human GM-CSF; B: GM-CSF release from explanted capsules that were subcutaneously implanted in mice for one week (same groups as in Figure A); C: GM-CSF level in serum of mice implanted with capsules for one week (same groups as in Figure A); D: Quantity of GM-CSF detected in the subcutaneous tissue around the implanted capsule after one week (same groups as in Figure A).

Under sterile culture condition, approximately 800,000 cells were loaded into the capsules. Capsules were maintained in culture medium at 37° C. and 5% $CO_2$. The delivery of human GM-CSF was quantified in culture medium using an ELISA (Kit #KHC2011, Thermo Fischer) and reported in ng/24 hrs (FIG. 12A).

Capsules were then implanted in the mouse subcutaneous tissue for 1 week. After sacrifice, the capsules were retrieved from animals and placed in culture medium for the quantification of human GM-CSF delivery (FIG. 12B). In addition, GM-CSF was quantified in the mouse serum (FIG. 12C) as well as in the subcutaneous tissue surrounding the capsules (FIG. 12D).

Those data support that the culture of known genetically engineered K562 human erythroleukemia cell line expressing human GM-CSF in a matrix containing macrocapsule as per an embodiment of the present invention represents already an improvement as compared to a capsule as described in WO 2017/064571. However, combination of the novel genetically engineered immortalized myoblast according to the invention in a matrix containing macrocapsule as per an embodiment of the present invention is by far the most efficient for achieving sustained, stable GM-CSF production both in-vitro and in-vivo.

Example 6: Diversity of Possible Genetically Modified Immortalized Human Myoblast Cell Line to Produce Antigens of Interest The ability of immortalized myoblast cells according to the invention to be genetically engineered for the expression and secretion of an antigen of interest such as for vaccination purposes has been assayed as follows.

Figure 15:
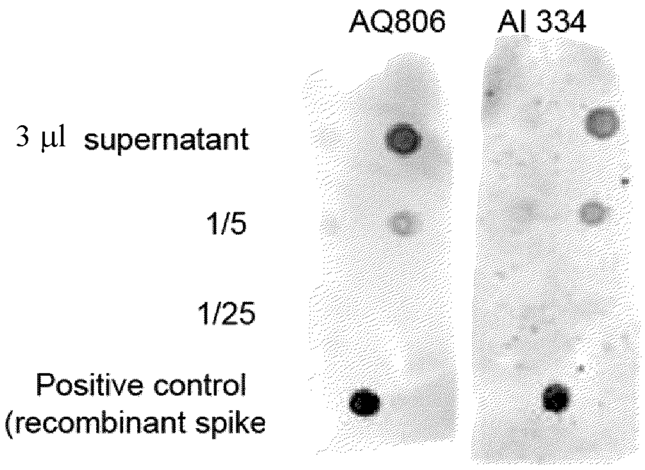
FIG. 15 represents a dot blot detecting COVID-19 spike protein in the pure or diluted (1:5, 1:25) culture supernatant of transduced immortalized myoblasts, using two different primary antibodies AQ806 and AI334, as described in Example 6.

For the expression of COVID-19 spike protein trimer [NC_045512.2 (21563 . . . 25384)], the DNA sequence encoding for the 1-1,208 residues of the COVID-19 S protein (UNIPROT P0DTC2 SPIKE_SARS2) was modified with proline substitution at positions 986 and 987, GSAS substitution at furine cleavage site 682-685, addition of a T4 fibritin trimerization domain and codon optimization for expression in human cells (SEQ ID NO: 1). This modified sequence was then synthesized and cloned into a 3$^{rd}$ generation pLV-hPGK-WPRE lentiviral vectors (Vectorbuilder). Myoblast cells were infected with various MOI. The secretion of spike protein in the culture medium was assessed by dot blot. Briefly, 3 ml of culture pure or diluted supernatant were loaded on nitrocellulose membrane, membrane was blocked in PBS with 3% powdered milk, washed 3 times in PBS and probed with 1 mg/ml AI 334 (US 2010/0172917; Yuan et al., 2020, *Science,* 8; 368(6491): 630-633) or AQ 806 (oap.unige.ch/journals/abrep/article/view/186; oap.unige.ch/journals/abrep/article/view/219; Wrap et al., 2020, *Cell,* 28; 181(5):1004-1015) antibodies overnight (available from the Geneva Antibody Facility, See World Wide Web: unige.ch/medicine/antibodies/cov-resources/). Membrane was revealed following incubation with HRP labeled secondary antibodies. The analysis demonstrated that spike protein was secreted in the supernatant of transduced immortalized myoblasts (FIG. 15).

Those data support that immortalized myoblast cells according to the invention can be successfully modified to express a large variety of proteins of therapeutic interest. In the case of viral antigens immortalized myoblast cells according to the invention genetically engineered to express those can be advantageously used in vaccination strategies, notably in combination with agents that increase the immune response.

The invention claimed is:

1. An immortalized human myoblast cell line deposited with Culture Collection of Switzerland (CCOS) under accession number 1902 or a composition thereof.

2. A pharmaceutical composition comprising the immortalized human myoblast cell line according to claim 1 and a pharmaceutically acceptable carrier, diluent or excipient thereof.

3. The implantable biocompatible device or a kit comprising the immortalized human myoblast cell line according to claim 1.

4. A genetically engineered immortalized human myoblast cell line secreting granulocyte-macrophage colony stimulating-factor (GM-CSF) deposited with Culture Collection of Switzerland (CCOS) under accession number 1901 or a composition thereof.

5. A pharmaceutical composition comprising the genetically engineered immortalized human myoblast cell line according to claim 4 and a pharmaceutically acceptable carrier, diluent or excipient thereof.

6. An implantable biocompatible device or a kit comprising the genetically engineered immortalized human myoblast cell line according to claim 4.

* * * * *

SEQUENCE LISTING

```
<160> NUMBER OF SEQ ID NOS: 7

<210> SEQ ID NO 1
<211> LENGTH: 3714
```

<212> TYPE: DNA
<213> ORGANISM: Artificial sequence
<220> FEATURE:
<223> OTHER INFORMATION: DNA Sequence for the expression of Spike
      protein by immortalized myoblasts

<400> SEQUENCE: 1

```
atgttcgttt tccttgttct gttgcctctc gttagtagcc aatgtgtcaa ccttactact     60

agaacccagc tccctccagc atataccaac agcttcaccc ggggcgtata ttatccggac    120

aaagtgtttc gctcaagtgt gctgcattct acgcaggacc tttttttgcc ctttttttagt    180

aatgttactt ggtttcatgc tatccatgtg tctggaacta acggaaccaa acggtttgac    240

aaccccgtcc tccctttcaa cgatggcgtg tatttcgcct ccacggaaaa gtcgaacatc    300

attcgcggct ggatctttgg tacaacactc gactcaaaga cgcagagcct gctaatcgtc    360

aataacgcta caaatgttgt gatcaaggtg tgtgaatttc agttctgcaa tgatcccttc    420

ctgggggtgt actaccataa aaataacaag agctggatgg agtccgaatt tagggtttac    480

agttccgcta acaactgcac attcgagtac gtaagccagc catttcttat ggatcttgag    540

ggcaagcaag gaaacttcaa gaatttaagg gagttcgtgt tcaaaaatat cgatggctat    600

tttaaaatat atagcaagca cactccaata aacttagtgc gagacctgcc ccagggattt    660

tcggctctag agcccctggt ggatctgcca attggaataa acataacccg ctttcaaaca    720

ctgctagccc tgcatagaag ttacctcacc cctggtgata gtagttccgg atggacagca    780

ggggccgccg catactatgt cggctacctg cagcctagga ccttcttact gaagtataac    840

gagaacggta caataaccga cgctgtggac tgcgctctgg accctctgtc cgagacgaag    900

tgtaccctaa agagctttac cgttgaaaaa ggcatttatc aaaccagcaa tttccgggtc    960

cagccaaccg agagcatcgt cagatttccc aacattacaa atctgtgtcc cttcggcgag   1020

gtgtttaacg ccacacgttt cgcctcagtg tacgcatgga accgtaaacg aatatctaac   1080

tgtgtcgcgg attattctgt cctctacaac tccgcctctt tctccacctt caagtgctac   1140

ggggtgtcac cgactaagct gaacgatctc tgctttacca acgtctacgc ggactccttc   1200

gtgatcagag gggatgaggt gagacaaatc gccccaggtc agactgggaa aatcgcagat   1260

tacaactaca aattgcctga tgatttcact gggtgcgtca tcgcgtggaa ctctaataac   1320

ctcgattcta aggtcggggg gaactacaat tatctgtacc gcctatttag gaagtcaaac   1380

ctgaaacctt tcgagcggga tatttcaacc gaaatctatc aagcggggtc aacaccttgt   1440

aatggtgtgg aaggatttaa ctgctacttc cccctgcagt cttacggatt tcagccaacc   1500

aatggcgtgg gttaccaacc ttatcgggtg gtggttctaa gtttcgaact gttgcacgct   1560

cccgccacgg tatgcgggcc aaaaaagagc actaacttgg tgaagaataa gtgcgtgaat   1620

ttcaatttca atggcctcac tggaaccgga gtactgaccg aatccaataa gaagttcttg   1680

ccctttcagc agttcggaag agacattgcc gacacaaccg acgcggtgcg ggatcctcag   1740

actctggaga tattagacat tacaccatgt agctttggcg gggtgtctgt cattactccg   1800

ggcacgaata ctagcaatca ggtagccgtg ctgtaccaag acgtgaattg cacagaggtt   1860

cccgtcgcaa ttcacgctga ccagctgacc cccacgtgga gggtttacag cactggcagt   1920

aatgtcttcc agacgagagc cggttgtttg atcggagcgg aacatgtgaa taactcctac   1980

gagtgcgaca tccccatcgg agccggtata tgcgcctctt atcagacaca aactaattca   2040

cccggctccg cctccagtgt agcttctcaa agcattatag catatacaat gtctcttggg   2100

gccgaaaatt ccgtggccta ttcgaacaat tcaatcgcca tcccaaccaa ctttacaatc   2160
```

agcgtgacga ccgaaattct gcctgtgagc atgacgaaaa ccagcgtaga ctgcactatg 2220
tatatctgtg gggactccac tgagtgctcc aaccttctcc tgcagtacgg gagcttctgt 2280
acccaattaa accgtgccct tacaggcatc gctgttgagc aggataagaa tacccaggaa 2340
gtttttgccc aggttaagca gatatacaaa acaccgccaa ttaaagactt cggaggcttc 2400
aacttctctc agatactgcc tgacccttcc aagccatcaa aacggagctt cattgaggac 2460
ctcttgttca acaaagtgac tctggctgat gctggcttca ttaagcagta cggagattgc 2520
ctgggggata ttgctgccag ggatctcatc tgtgcccaga agtttaatgg cctgacagtc 2580
ttgcctccac ttctgacaga cgagatgatt gcacagtaca caagtgccct cctcgctggc 2640
accataacat ccggatggac atttggtgca ggtgctgccc tccagattcc ctttgcaatg 2700
cagatggcgt atcgctttaa cggcatcggt gtcacacaaa acgtgttgta tgagaaccaa 2760
aagctcatcg ctaaccagtt taattctgct attgggaaaa ttcaggacag cctgtcatcg 2820
accgcgtctg cccttgggaa gttgcaggac gtggtgaatc agaatgctca ggccttaaat 2880
actctggtga aacaactctc ttcaaatttc ggcgcaatca gctctgtgtt aaacgacatc 2940
ctaagtaggc ttgatccgcc ggaggctgaa gttcaaattg atagattgat tactggcagg 3000
ctccagtctt tacagaccta cgttacacag cagctgatcc gagcggctga gattagagct 3060
tccgccaatc tggccgcaac caagatgtcc gaatgtgtcc tgggtcagtc aaagcgggtc 3120
gacttttgtg gtaaaggcta ccacctcatg tcatttcccc agagtgcacc tcacggagta 3180
gtgttcctcc acgtcaccta cgttccagca caggaaaaga attttaccac tgcaccggca 3240
atctgtcacg acggcaaggc acacttcccc cgagagggcg tattcgtgtc gaatggaact 3300
cattggttcg tcacacagcg aaacttttat gagcctcaga tcattaccac cgataataca 3360
tttgtgtccg ggaactgcga cgttgtcatt ggaatcgtca acaacactgt atacgatcca 3420
cttcagccag aactggatag ctttaaggaa gaattggaca aatatttcaa aaatcacact 3480
tcacccgatg tggacctggg ggacattagt gggatcaatg catccgtggt caatatccaa 3540
aaagagattg acaggctcaa cgaggtggcc aaaaatctga acgaaagtct tatcgatctg 3600
caagaattgg gaaaatatga gcagggcagc ggctatatcc cagaggcccc ccgcgacggc 3660
caggcctacg tacgcaagga tggcgagtgg gtgctgctga gcaccttcct gtga 3714

<210> SEQ ID NO 2
<211> LENGTH: 7405
<212> TYPE: DNA
<213> ORGANISM: Artificial sequence
<220> FEATURE:
<223> OTHER INFORMATION: Lentiviral vector construct encoding for the light chain of ipilimumab (pLV-hPGK-WPRE)

<400> SEQUENCE: 2
aatgtagtct tatgcaatac tcttgtagtc ttgcaacatg gtaacgatga gttagcaaca 60
tgccttacaa ggagagaaaa agcaccgtgc atgccgattg gtggaagtaa ggtggtacga 120
tcgtgcctta ttaggaaggc aacagacggg tctgacatgg attggacgaa ccactgaatt 180
gccgcattgc agagatattg tatttaagtg cctagctcga tacataaacg ggtctctctg 240
gttagaccag atctgagcct gggagctctc tggctaacta gggaacccac tgcttaagcc 300
tcaataaagc ttgccttgag tgcttcaagt agtgtgtgcc cgtctgttgt gtgactctgg 360
taactagaga tccctcagac ccttttagtc agtgtggaaa atctctagca gtggcgcccg 420
aacagggact tgaaagcgaa agggaaacca gaggagctct ctcgacgcag gactcggctt 480

-continued

```
gctgaagcgc gcacggcaag aggcgagggg cggcgactgg tgagtacgcc aaaaattttg    540
actagcggag gctagaagga gagagatggg tgcgagagcg tcagtattaa gcgggggaga    600
attagatcgc gatgggaaaa aattcggtta aggccagggg gaaagaaaaa atataaatta    660
aaacatatag tatgggcaag cagggagcta gaacgattcg cagttaatcc tggcctgtta    720
gaaacatcag aaggctgtag acaaatactg ggacagctac aaccatccct tcagacagga    780
tcagaagaac ttagatcatt atataataca gtagcaaccc tctattgtgt gcatcaaagg    840
atagagataa aagacaccaa ggaagcttta gacaagatag aggaagagca aaacaaaagt    900
aagaccaccg cacagcaagc ggccgctgat cttcagacct ggaggaggag atatgaggga    960
caattggaga agtgaattat ataaatataa agtagtaaaa attgaaccat taggagtagc   1020
acccaccaag gcaaagagaa gagtggtgca gagagaaaaa agagcagtgg gaataggagc   1080
tttgttcctt gggttcttgg gagcagcagg aagcactatg ggcgcagcgt caatgacgct   1140
gacggtacag gccagacaat tattgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agtttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcgcta   1800
gcttttaaaa gaaaaggggg gattgggggg tacagtgcag gggaaagaat agtagacata   1860
atagcaacag acatacaaac taaagaatta caaaaacaaa ttacaaaaat tcaaaatttt   1920
actagtgatt atcggatcaa ctttgtatag aaaagttggg gttgcgcctt ttccaaggca   1980
gccctgggtt tgcgcaggga cgcggctgct ctgggcgtgg ttccgggaaa cgcagcggcg   2040
ccgaccctgg gtctcgcaca ttcttcacgt ccgttcgcag cgtcacccgg atcttcgccg   2100
ctacccttgt gggccccccg gcgacgcttc ctgctccgcc cctaagtcgg gaaggttcct   2160
tgcggttcgc ggcgtgccgg acgtgacaaa cggaagccgc acgtctcact agtaccctcg   2220
cagacggaca gcgccaggga gcaatggcag cgcgccgacc gcgatgggct gtggccaata   2280
gcggctgctc agcagggcgc gccgagagca gcggccggga aggggcggtg cgggaggcgg   2340
ggtgtggggc ggtagtgtgg gccctgttcc tgcccgcgcg gtgttccgca ttctgcaagc   2400
ctccggagcg cacgtcggca gtcggctccc tcgttgaccg aatcaccgac ctctctcccc   2460
aggcaagttt gtacaaaaaa gcaggctgcc accatgaaat acctattgcc tacggcagcc   2520
gctggattgt tattactcgc ggcccagccg gccatggccg agatcgtgct gacccagagc   2580
cccggcaccc tgagcctgag ccccggcgag agagccaccc tgagctgcag agccagccag   2640
agcgtgggca gcagctacct ggcctggtac cagcagaagc ccggccaggc ccccagactg   2700
ctgatctacg gcgccttcag cagagccacc ggcatccccg acagattcag cggcagcggc   2760
agcggcaccg acttcaccct gaccatcagc agactggagc ccgaggactt cgccgtgtac   2820
```

-continued

```
tactgccagc agtacggcag cagcccctgg accttcggcc agggcaccaa ggtggagatc   2880
aagagaaccg tggccgcccc cagcgtgttc atcttccccc ccagcgacga gcagctgaag   2940
agcggcaccg ccagcgtggt gtgcctgctg aacaacttct accccagaga ggccaaggtg   3000
cagtggaagg tggacaacgc cctgcagagc ggcaacagcc aggagagcgt gaccgagcag   3060
gacagcaagg acagcaccta cagcctgagc agcaccctga ccctgagcaa ggccgactac   3120
gagaagcaca aggtgtacgc ctgcgaggtg acccaccagg gcctgagcag ccccgtgacc   3180
aagagcttca acagaggcga gtgctgaacc cagctttctt gtacaaagtg gtgataatcg   3240
aattccgata atcaacctct ggattacaaa atttgtgaaa gattgactgg tattcttaac   3300
tatgttgctc cttttacgct atgtggatac gctgctttaa tgcctttgta tcatgctatt   3360
gcttcccgta tggctttcat tttctcctcc ttgtataaat cctggttgct gtctctttat   3420
gaggagttgt ggcccgttgt caggcaacgt ggcgtggtgt gcactgtgtt tgctgacgca   3480
acccccactg gttggggcat tgccaccacc tgtcagctcc tttccgggac tttcgctttc   3540
cccctcccta ttgccacggc ggaactcatc gccgcctgcc ttgcccgctg ctggacaggg   3600
gctcggctgt tgggcactga caattccgtg gtgttgtcgg ggaagctgac gtcctttcca   3660
tggctgctcg cctgtgttgc cacctggatt ctgcgcggga cgtccttctg ctacgtccct   3720
tcggccctca atccagcgga ccttccttcc cgcggcctgc tgccggctct gcggcctctt   3780
ccgcgtcttc gccttcgccc tcagacgagt cggatctccc tttgggccgc ctccccgcat   3840
cgggaattcc cgcggttcgc tttaagacca atgacttaca aggcagctgt agatcttagc   3900
cactttttaa aagaaaaggg gggactggaa gggctaattc actcccaacg aagacaagat   3960
ctgctttttg cttgtactgg gtctctctgg ttagaccaga tctgagcctg ggagctctct   4020
ggctaactag ggaacccact gcttaagcct caataaagct tgccttgagt gcttcaagta   4080
gtgtgtgccc gtctgttgtg tgactctggt aactagagat ccctcagacc cttttagtca   4140
gtgtggaaaa tctctagcag tagtagttca tgtcatctta ttattcagta tttataactt   4200
gcaaagaaat gaatatcaga gagtgagagg aacttgttta ttgcagctta taatggttac   4260
aaataaagca atagcatcac aaatttcaca aataaagcat ttttttcact gcattctagt   4320
tgtggtttgt ccaaactcat caatgtatct tatcatgtct ggctctagct atcccgcccc   4380
taactccgcc catcccgccc ctaactccgc ccagttccgc ccattctccg ccccatggct   4440
gactaatttt ttttatttat gcagaggccg aggccgcctc ggcctctgag ctattccaga   4500
agtagtgagg aggctttttt ggaggcctag ggacgtaccc aattcgccct atagtgagtc   4560
gtattacgcg cgctcactgg ccgtcgtttt acaacgtcgt gactgggaaa accctggcgt   4620
tacccaactt aatcgccttg cagcacatcc ccctttcgcc agctggcgta atagcgaaga   4680
ggcccgcacc gatcgccctt cccaacagtt gcgcagcctg aatggcgaat gggacgcgcc   4740
ctgtagcggc gcattaagcg cggcgggtgt ggtggttacg cgcagcgtga ccgctacact   4800
tgccagcgcc ctagcgcccg ctcctttcgc tttcttccct tcctttctcg ccacgttcgc   4860
cggctttccc cgtcaagctc taaatcgggg gctcccttta gggttccgat ttagtgcttt   4920
acggcacctc gaccccaaaa aacttgatta gggtgatggt tcacgtagtg ggccatcgcc   4980
ctgatagacg gtttttcgcc ctttgacgtt ggagtccacg ttctttaata gtggactctt   5040
gttccaaact ggaacaacac tcaaccctat ctcggtctat tcttttgatt tataagggat   5100
tttgccgatt tcggcctatt ggttaaaaaa tgagctgatt taacaaaaat ttaacgcgaa   5160
ttttaacaaa atattaacgc ttacaattta ggtggcactt ttcggggaaa tgtgcgcgga   5220
```

acccctattt gtttattttt ctaaatacat tcaaatatgt atccgctcat gagacaataa 5280
ccctgataaa tgcttcaata atattgaaaa aggaagagta tgagtattca acatttccgt 5340
gtcgccctta ttcccttttt tgcggcattt tgccttcctg tttttgctca cccagaaacg 5400
ctggtgaaag taaaagatgc tgaagatcag ttgggtgcac gagtgggtta catcgaactg 5460
gatctcaaca gcggtaagat ccttgagagt tttcgccccg aagaacgttt tccaatgatg 5520
agcactttta aagttctgct atgtggcgcg gtattatccc gtattgacgc cgggcaagag 5580
caactcggtc gccgcataca ctattctcag aatgacttgg ttgagtactc accagtcaca 5640
gaaaagcatc ttacggatgg catgacagta agagaattat gcagtgctgc cataaccatg 5700
agtgataaca ctgcggccaa cttacttctg acaacgatcg gaggaccgaa ggagctaacc 5760
gcttttttgc acaacatggg ggatcatgta actcgccttg atcgttggga accggagctg 5820
aatgaagcca taccaaacga cgagcgtgac accacgatgc ctgtagcaat ggcaacaacg 5880
ttgcgcaaac tattaactgg cgaactactt actctagctt cccggcaaca attaatagac 5940
tggatggagg cggataaagt tgcaggacca cttctgcgct cggcccttcc ggctggctgg 6000
tttattgctg ataaatctgg agccggtgag cgtgggtctc gcggtatcat tgcagcactg 6060
gggccagatg gtaagccctc ccgtatcgta gttatctaca cgacggggag tcaggcaact 6120
atggatgaac gaaatagaca gatcgctgag ataggtgcct cactgattaa gcattggtaa 6180
ctgtcagacc aagtttactc atatatactt tagattgatt taaaacttca tttttaattt 6240
aaaaggatct aggtgaagat cctttttgat aatctcatga ccaaaatccc ttaacgtgag 6300
ttttcgttcc actgagcgtc agaccccgta gaaaagatca aaggatcttc ttgagatcct 6360 tttttctgc gcgtaatctg ctgcttgcaa acaaaaaaac caccgctacc agcggtggtt 6420
tgtttgccgg atcaagagct accaactctt tttccgaagg taactggctt cagcagagcg 6480
cagataccaa atactgttct tctagtgtag ccgtagttag gccaccactt caagaactct 6540
gtagcaccgc ctacatacct cgctctgcta atcctgttac cagtggctgc tgccagtggc 6600
gataagtcgt gtcttaccgg gttggactca agacgatagt taccggataa ggcgcagcgg 6660
tcgggctgaa cggggggttc gtgcacacag cccagcttgg agcgaacgac ctacaccgaa 6720
ctgagatacc tacagcgtga gctatgagaa agcgccacgc ttcccgaaga gagaaaggcg 6780
gacaggtatc cggtaagcgg cagggtcgga acaggagagc gcacgaggga gcttccaggg 6840
ggaaacgcct ggtatcttta tagtcctgtc gggtttcgcc acctctgact tgagcgtcga 6900
tttttgtgat gctcgtcagg ggggcggagc ctatggaaaa acgccagcaa cgcggccttt 6960
ttacggttcc tggccttttg ctggcctttt gctcacatgt tctttcctgc gttatcccct 7020
gattctgtgg ataaccgtat taccgccttt gagtgagctg ataccgctcg ccgcagccga 7080
acgaccgagc gcagcgagtc agtgagcgag gaagcggaag agcgcccaat acgcaaaccg 7140
cctctccccg cgcgttggcc gattcattaa tgcagctggc acgacaggtt tcccgactgg 7200
aaagcgggca gtgagcgcaa cgcaattaat gtgagttagc tcactcatta ggcaccccag 7260
gctttacact ttatgcttcc ggctcgtatg ttgtgtggaa ttgtgagcgg ataacaattt 7320
cacacaggaa acagctatga ccatgattac gccaagcgcg caattaaccc tcactaaagg 7380
gaacaaaagc tggagctgca agctt 7405

<210> SEQ ID NO 3
<211> LENGTH: 8095
<212> TYPE: DNA

<213> ORGANISM: Artificial sequence
<220> FEATURE:
<223> OTHER INFORMATION: lentiviral vector construct encoding for the heavy chain of ipilimumab (pLV-hPGK-ipi-HC-WPRE)

<400> SEQUENCE: 3
aatgtagtct tatgcaatac tcttgtagtc ttgcaacatg gtaacgatga gttagcaaca 60
tgccttacaa ggagagaaaa agcaccgtgc atgccgattg gtggaagtaa ggtggtacga 120
tcgtgcctta ttaggaaggc aacagacggg tctgacatgg attggacgaa ccactgaatt 180
gccgcattgc agagatattg tatttaagtg cctagctcga tacataaacg ggtctctctg 240
gttagaccag atctgagcct gggagctctc tggctaacta gggaacccac tgcttaagcc 300
tcaataaagc ttgccttgag tgcttcaagt agtgtgtgcc cgtctgttgt gtgactctgg 360
taactagaga tccctcagac ccttttagtc agtgtggaaa atctctagca gtggcgcccg 420
aacagggact tgaaagcgaa agggaaacca gaggagctct ctcgacgcag gactcggctt 480
gctgaagcgc gcacggcaag aggcgagggg cggcgactgg tgagtacgcc aaaaattttg 540
actagcggag gctagaagga gagagatggg tgcgagagcg tcagtattaa gcgggggaga 600
attagatcgc gatgggaaaa aattcggtta aggccagggg gaaagaaaaa atataaatta 660
aaacatatag tatgggcaag cagggagcta gaacgattcg cagttaatcc tggcctgtta 720
gaaacatcag aaggctgtag acaaatactg ggacagctac aaccatccct tcagacagga 780
tcagaagaac ttagatcatt atataataca gtagcaaccc tctattgtgt gcatcaaagg 840
atagagataa aagacaccaa ggaagcttta gacaagatag aggaagagca aaacaaaagt 900
aagaccaccg cacagcaagc ggccgctgat cttcagacct ggaggaggag atatgaggga 960
caattggaga agtgaattat ataaatataa agtagtaaaa attgaaccat taggagtagc 1020
acccaccaag gcaaagagaa gagtggtgca gagagaaaaa agagcagtgg gaataggagc 1080
tttgttcctt gggttcttgg gagcagcagg aagcactatg ggcgcagcgt caatgacgct 1140
gacggtacag gccagacaat tattgtctgg tatagtgcag cagcagaaca atttgctgag 1200
ggctattgag gcgcaacagc atctgttgca actcacagtc tggggcatca agcagctcca 1260
ggcaagaatc ctggctgtgg aaagatacct aaaggatcaa cagctcctgg ggatttgggg 1320
ttgctctgga aaactcattt gcaccactgc tgtgccttgg aatgctagtt ggagtaataa 1380
atctctggaa cagatttgga atcacacgac ctggatggag tgggacagag aaattaacaa 1440
ttacacaagc ttaatacact ccttaattga agaatcgcaa aaccagcaag aaaagaatga 1500
acaagaatta ttggaattag ataaatgggc aagtttgtgg aattggttta acataacaaa 1560
ttggctgtgg tatataaaat tattcataat gatagtagga ggcttggtag gtttaagaat 1620
agtttttgct gtactttcta tagtgaatag agttaggcag ggatattcac cattatcgtt 1680
tcagacccac ctcccaaccc cgaggggacc cgacaggccc gaaggaatag aagaagaagg 1740
tggagagaga gacagagaca gatccattcg attagtgaac ggatctcgac ggtatcgcta 1800
gcttttaaaa gaaaaggggg gattgggggg tacagtgcag gggaaagaat agtagacata 1860
atagcaacag acatacaaac taaagaatta caaaaacaaa ttacaaaaat tcaaaatttt 1920
actagtgatt atcggatcaa ctttgtatag aaaagttggg gttgcgcctt ttccaaggca 1980
gccctgggtt tgcgcaggga cgcggctgct ctgggcgtgg ttccgggaaa cgcagcggcg 2040
ccgaccctgg gtctcgcaca ttcttcacgt ccgttcgcag cgtcacccgg atcttcgccg 2100
ctacccttgt gggccccccg gcgacgcttc ctgctccgcc cctaagtcgg gaaggttcct 2160
tgcggttcgc ggcgtgccgg acgtgacaaa cggaagccgc acgtctcact agtaccctcg 2220
cagacggaca gcgccaggga gcaatggcag cgcgccgacc gcgatgggct gtggccaata 2280
gcggctgctc agcagggcgc gccgagagca gcggccggga aggggcggtg cgggaggcgg 2340
ggtgtggggc ggtagtgtgg gccctgttcc tgcccgcgcg gtgttccgca ttctgcaagc 2400
ctccggagcg cacgtcggca gtcggctccc tcgttgaccg aatcaccgac ctctctcccc 2460
aggcaagttt gtacaaaaaa gcaggctgcc accatggagt ttgggctgag ctgggttttc 2520
ctcgttgctc tttttagagg tgtccagtgt caggtgcagc tggtggagag cggcggcggc 2580
gtggtgcagc ccggcagaag cctgagactg agctgcgccg ccagcggctt caccttcagc 2640
agctacacca tgcactgggt gagacaggcc cccggcaagg gcctggagtg ggtgaccttc 2700
atcagctacg acggcaacaa caagtactac gccgacagcg tgaagggcag attcaccatc 2760
agcagagaca acagcaagaa caccctgtac ctgcagatga acagcctgag agccgaggac 2820
accgccatct actactgcgc cagaaccggc tggctgggcc ccttcgacta ctggggccag 2880
ggcaccctgg tgaccgtgag cagcgccagc accaagggcc ccagcgtgtt cccccctggcc 2940 cccagcagca agagcaccag cggcggcacc gccgccctgg gctgcctggt gaaggactac 3000
ttccccgagc ccgtgaccgt gagctggaac agcggcgccc tgaccagcgg cgtgcacacc 3060
ttccccgccg tgctgcagag cagcggcctg tacagcctga gcagcgtggt gaccgtgccc 3120
agcagcagcc tgggcaccca gacctacatc tgcaacgtga accacaagcc cagcaacacc 3180
aaggtggaca agagagtgga gcccaagagc tgcgacaaga cccacacctg cccccccctgc 3240 cccgcccccg agctgctggg cggccccagc gtgttcctgt tccccccccaa gcccaaggac 3300 accctgatga tcagcagaac ccccgaggtg acctgcgtgg tggtggacgt gagccacgag 3360
gaccccgagg tgaagttcaa ctggtacgtg gacggcgtgg aggtgcacaa cgccaagacc 3420
aagcccagag aggagcagta caacagcacc tacagagtgg tgagcgtgct gaccgtgctg 3480
caccaggact ggctgaacgg caaggagtac aagtgcaagg tgagcaacaa ggccctgccc 3540
gcccccatcg agaagaccat cagcaaggcc aagggccagc ccagagagcc ccaggtgtac 3600
accctgcccc ccagcagaga cgagctgacc aagaaccagg tgagcctgac ctgcctggtg 3660
aagggcttct accccagcga catcgccgtg gagtgggaga gcaacggcca gcccgagaac 3720
aactacaaga ccaccccccc cgtgctggac agcgacggca gcttcttcct gtacagcaag 3780
ctgaccgtgg acaagagcag atggcagcag ggcaacgtgt tcagctgcag cgtgatgcac 3840
gaggccctgc acaaccacta cacccagaag agcctgagcc tgagccccgg caagtgaacc 3900
cagctttctt gtacaaagtg gtgataatcg aattccgata atcaacctct ggattacaaa 3960
atttgtgaaa gattgactgg tattcttaac tatgttgctc cttttacgct atgtggatac 4020
gctgctttaa tgcctttgta tcatgctatt gcttcccgta tggctttcat tttctcctcc 4080
ttgtataaat cctggttgct gtctctttat gaggagttgt ggcccgttgt caggcaacgt 4140
ggcgtggtgt gcactgtgtt tgctgacgca acccccactg gttggggcat tgccaccacc 4200
tgtcagctcc tttccgggac tttcgctttc cccctcccta ttgccacggc ggaactcatc 4260
gccgcctgcc ttgcccgctg ctggacaggg gctcggctgt tgggcactga caattccgtg 4320
gtgttgtcgg ggaagctgac gtcctttcca tggctgctcg cctgtgttgc cacctggatt 4380
ctgcgcggga cgtccttctg ctacgtccct tcggccctca atccagcgga ccttccttcc 4440
cgcggcctgc tgccggctct gcggcctctt ccgcgtcttc gccttcgccc tcagacgagt 4500
cggatctccc tttgggccgc ctccccgcat cgggaattcc cgcggttcgc tttaagacca 4560

```
atgacttaca aggcagctgt agatcttagc cactttttaa aagaaaaggg gggactggaa   4620
gggctaattc actcccaacg aagacaagat ctgctttttg cttgtactgg gtctctctgg   4680
ttagaccaga tctgagcctg ggagctctct ggctaactag ggaacccact gcttaagcct   4740
caataaagct tgccttgagt gcttcaagta gtgtgtgccc gtctgttgtg tgactctggt   4800
aactagagat ccctcagacc cttttagtca gtgtggaaaa tctctagcag tagtagttca   4860
tgtcatctta ttattcagta tttataactt gcaaagaaat gaatatcaga gagtgagagg   4920
aacttgttta ttgcagctta taatggttac aaataaagca atagcatcac aaatttcaca   4980
aataaagcat ttttttcact gcattctagt tgtggtttgt ccaaactcat caatgtatct   5040
tatcatgtct ggctctagct atcccgcccc taactccgcc catcccgccc ctaactccgc   5100
ccagttccgc ccattctccg ccccatggct gactaatttt ttttatttat gcagaggccg   5160
aggccgcctc ggcctctgag ctattccaga agtagtgagg aggctttttt ggaggcctag   5220
ggacgtaccc aattcgccct atagtgagtc gtattacgcg cgctcactgg ccgtcgtttt   5280
acaacgtcgt gactgggaaa accctggcgt tacccaactt aatcgccttg cagcacatcc   5340
ccctttcgcc agctggcgta atagcgaaga ggcccgcacc gatcgccctt cccaacagtt   5400
gcgcagcctg aatggcgaat gggacgcgcc ctgtagcggc gcattaagcg cggcgggtgt   5460
ggtggttacg cgcagcgtga ccgctacact tgccagcgcc ctagcgcccg ctcctttcgc   5520
tttcttccct tcctttctcg ccacgttcgc cggctttccc cgtcaagctc taaatcgggg   5580
gctcccttta gggttccgat ttagtgcttt acggcacctc gaccccaaaa aacttgatta   5640
gggtgatggt tcacgtagtg ggccatcgcc ctgatagacg gtttttcgcc ctttgacgtt   5700
ggagtccacg ttctttaata gtggactctt gttccaaact ggaacaacac tcaaccctat   5760
ctcggtctat tcttttgatt tataagggat tttgccgatt tcggcctatt ggttaaaaaa   5820
tgagctgatt taacaaaaat ttaacgcgaa ttttaacaaa atattaacgc ttacaattta   5880
ggtggcactt ttcggggaaa tgtgcgcgga acccctattt gtttattttt ctaaatacat   5940
tcaaatatgt atccgctcat gagacaataa ccctgataaa tgcttcaata atattgaaaa   6000
aggaagagta tgagtattca acatttccgt gtcgccctta ttcccttttt tgcggcattt   6060
tgccttcctg tttttgctca cccagaaacg ctggtgaaag taaaagatgc tgaagatcag   6120
ttgggtgcac gagtgggtta catcgaactg gatctcaaca gcggtaagat ccttgagagt   6180
tttcgccccg aagaacgttt tccaatgatg agcactttta aagttctgct atgtggcgcg   6240
gtattatccc gtattgacgc cgggcaagag caactcggtc gccgcataca ctattctcag   6300
aatgacttgg ttgagtactc accagtcaca gaaaagcatc ttacggatgg catgacagta   6360
agagaattat gcagtgctgc cataaccatg agtgataaca ctgcggccaa cttacttctg   6420
acaacgatcg gaggaccgaa ggagctaacc gcttttttgc acaacatggg ggatcatgta   6480
actcgccttg atcgttggga accggagctg aatgaagcca taccaaacga cgagcgtgac   6540
accacgatgc ctgtagcaat ggcaacaacg ttgcgcaaac tattaactgg cgaactactt   6600
actctagctt cccggcaaca attaatagac tggatggagg cggataaagt tgcaggacca   6660
cttctgcgct cggcccttcc ggctggctgg tttattgctg ataaatctgg agccggtgag   6720
cgtgggtctc gcggtatcat tgcagcactg gggccagatg gtaagccctc ccgtatcgta   6780
gttatctaca cgacggggag tcaggcaact atggatgaac gaaatagaca gatcgctgag   6840
ataggtgcct cactgattaa gcattggtaa ctgtcagacc aagtttactc atatatactt   6900
```

```
tagattgatt taaaacttca tttttaattt aaaaggatct aggtgaagat cctttttgat   6960
aatctcatga ccaaaatccc ttaacgtgag ttttcgttcc actgagcgtc agaccccgta   7020
gaaaagatca aaggatcttc ttgagatcct ttttttctgc gcgtaatctg ctgcttgcaa   7080
acaaaaaaac caccgctacc agcggtggtt tgtttgccgg atcaagagct accaactctt   7140
tttccgaagg taactggctt cagcagagcg cagataccaa atactgttct tctagtgtag   7200
ccgtagttag gccaccactt caagaactct gtagcaccgc ctacatacct cgctctgcta   7260
atcctgttac cagtggctgc tgccagtggc gataagtcgt gtcttaccgg gttggactca   7320
agacgatagt taccggataa ggcgcagcgg tcgggctgaa cggggggttc gtgcacacag   7380
cccagcttgg agcgaacgac ctacaccgaa ctgagatacc tacagcgtga gctatgagaa   7440
agcgccacgc ttcccgaaga gagaaaggcg gacaggtatc cggtaagcgg cagggtcgga   7500
acaggagagc gcacgaggga gcttccaggg ggaaacgcct ggtatcttta tagtcctgtc   7560
gggtttcgcc acctctgact tgagcgtcga tttttgtgat gctcgtcagg ggggcggagc   7620
ctatggaaaa acgccagcaa cgcggccttt ttacggttcc tggccttttg ctggcctttt   7680
gctcacatgt tctttcctgc gttatcccct gattctgtgg ataaccgtat taccgccttt   7740
gagtgagctg ataccgctcg ccgcagccga acgaccgagc gcagcgagtc agtgagcgag   7800
gaagcggaag agcgcccaat acgcaaaccg cctctccccg cgcgttggcc gattcattaa   7860
tgcagctggc acgacaggtt tcccgactgg aaagcgggca gtgagcgcaa cgcaattaat   7920
gtgagttagc tcactcatta ggcaccccag gctttacact ttatgcttcc ggctcgtatg   7980
ttgtgtggaa ttgtgagcgg ataacaattt cacacaggaa acagctatga ccatgattac   8040
gccaagcgcg caattaaccc tcactaaagg gaacaaaagc tggagctgca agctt        8095
```

<210> SEQ ID NO 4
<211> LENGTH: 8119
<212> TYPE: DNA
<213> ORGANISM: Artificial sequence
<220> FEATURE:
<223> OTHER INFORMATION: lentiviral vector construct encoding for the heavy chain of gantenerumab (pLV-hPGK-Gant HC-WPRE)

<400> SEQUENCE: 4

```
aatgtagtct tatgcaatac tcttgtagtc ttgcaacatg gtaacgatga gttagcaaca     60
tgccttacaa ggagagaaaa agcaccgtgc atgccgattg gtggaagtaa ggtggtacga    120
tcgtgcctta ttaggaaggc aacagacggg tctgacatgg attggacgaa ccactgaatt    180
gccgcattgc agagatattg tatttaagtg cctagctcga tacataaacg ggtctctctg    240
gttagaccag atctgagcct gggagctctc tggctaacta gggaacccac tgcttaagcc    300
tcaataaagc ttgccttgag tgcttcaagt agtgtgtgcc cgtctgttgt gtgactctgg    360
taactagaga tccctcagac ccttttagtc agtgtggaaa atctctagca gtggcgcccg    420
aacagggact tgaaagcgaa agggaaacca gaggagctct ctcgacgcag gactcggctt    480
gctgaagcgc gcacggcaag aggcgagggg cggcgactgg tgagtacgcc aaaaattttg    540
actagcggag gctagaagga gagagatggg tgcgagagcg tcagtattaa gcgggggaga    600
attagatcgc gatgggaaaa aattcggtta aggccagggg gaaagaaaaa atataaatta    660
aaacatatag tatgggcaag cagggagcta gaacgattcg cagttaatcc tggcctgtta    720
gaaacatcag aaggctgtag acaaatactg ggacagctac aaccatccct tcagacagga    780
tcagaagaac ttagatcatt atataataca gtagcaaccc tctattgtgt gcatcaaagg    840
```

-continued

```
atagagataa aagacaccaa ggaagcttta gacaagatag aggaagagca aaacaaaagt    900
aagaccaccg cacagcaagc ggccgctgat cttcagacct ggaggaggag atatgaggga    960
caattggaga agtgaattat ataaatataa agtagtaaaa attgaaccat taggagtagc   1020
acccaccaag gcaaagagaa gagtggtgca gagagaaaaa agagcagtgg gaataggagc   1080
tttgttcctt gggttcttgg gagcagcagg aagcactatg ggcgcagcgt caatgacgct   1140
gacggtacag gccagacaat tattgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agtttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcgcta   1800
gcttttaaaa gaaaaggggg gattgggggg tacagtgcag gggaaagaat agtagacata   1860
atagcaacag acatacaaac taaagaatta caaaaacaaa ttacaaaaat tcaaaatttt   1920
actagtgatt atcggatcaa ctttgtatag aaaagttggg gttgcgcctt ttccaaggca   1980
gccctgggtt tgcgcaggga cgcggctgct ctgggcgtgg ttccgggaaa cgcagcggcg   2040
ccgaccctgg gtctcgcaca ttcttcacgt ccgttcgcag cgtcacccgg atcttcgccg   2100
ctacccttgt gggccccccg gcgacgcttc ctgctccgcc cctaagtcgg gaaggttcct   2160
tgcggttcgc ggcgtgccgg acgtgacaaa cggaagccgc acgtctcact agtaccctcg   2220
cagacggaca gcgccaggga gcaatggcag cgcgccgacc gcgatgggct gtggccaata   2280
gcggctgctc agcagggcgc gccgagagca gcggccggga aggggcggtg cgggaggcgg   2340
ggtgtggggc ggtagtgtgg gccctgttcc tgcccgcgcg gtgttccgca ttctgcaagc   2400
ctccggagcg cacgtcggca gtcggctccc tcgttgaccg aatcaccgac ctctctcccc   2460
aggcaagttt gtacaaaaaa gcaggctgcc accatggagt ttgggctgag ctgggttttc   2520
ctcgttgctc tttttagagg tgtccagtgt caggtggagc tggtggagag cggcggcggc   2580
ctggtgcagc ccggcggcag cctgagactg agctgcgccg ccagcggctt caccttcagc   2640
agctacgcca tgagctgggt gagacaggcc cccggcaagg gcctggagtg ggtgagcgcc   2700
atcaacgcca gcggcaccag aacctactac gccgacagcg tgaagggcag attcaccatc   2760
agcagagaca acagcaagaa caccctgtac ctgcagatga acagcctgag agccgaggac   2820
accgccgtgt actactgcgc cagaggcaag ggcaacaccc acaagcccta cggctacgtg   2880
agatacttcg acgtgtgggg ccagggcacc ctggtgaccg tgagcagcgc cagcaccaag   2940
ggccccagcg tgttccccct ggcccccagc agcaagagca ccagcggcgg caccgccgcc   3000
ctgggctgcc tggtgaagga ctacttcccc gagcccgtga ccgtgagctg gaacagcggc   3060
gccctgacca gcggcgtgca caccttcccc gccgtgctgc agagcagcgg cctgtacagc   3120
ctgagcagcg tggtgaccgt gcccagcagc agcctgggca cccagaccta catctgcaac   3180
gtgaaccaca agcccagcaa caccaaggtg gacaagagag tggagcccaa gagctgcgac   3240
```

-continued aagacccaca cctgcccccc ctgccccgcc cccgagctgc tgggcggccc cagcgtgttc 3300
ctgttccccc ccaagcccaa ggacaccctg atgatcagca gaacccccga ggtgacctgc 3360
gtggtggtgg acgtgagcca cgaggacccc gaggtgaagt tcaactggta cgtggacggc 3420
gtggaggtgc acaacgccaa gaccaagccc agagaggagc agtacaacag cacctacaga 3480
gtggtgagcg tgctgaccgt gctgcaccag gactggctga acggcaagga gtacaagtgc 3540
aaggtgagca acaaggccct gcccgccccc atcgagaaga ccatcagcaa ggccaagggc 3600
cagccccagag agccccaggt gtacaccctg ccccccagca gagacgagct gaccaagaac 3660
caggtgagcc tgacctgcct ggtgaagggc ttctacccca gcgacatcgc cgtggagtgg 3720
gagagcaacg gccagcccga gaacaactac aagaccaccc cccccgtgct ggacagcgac 3780
ggcagcttct tcctgtacag caagctgacc gtggacaaga gcagatggca gcagggcaac 3840
gtgttcagct gcagcgtgat gcacgaggcc ctgcacaacc actacaccca gaagagcctg 3900
agcctgagcc ccggcaagtg aacccagctt tcttgtacaa agtggtgata atcgaattcc 3960
gataatcaac ctctggatta caaaatttgt gaaagattga ctggtattct taactatgtt 4020
gctcctttta cgctatgtgg atacgctgct ttaatgcctt tgtatcatgc tattgcttcc 4080
cgtatggctt tcattttctc ctccttgtat aaatcctggt tgctgtctct ttatgaggag 4140
ttgtggcccg ttgtcaggca acgtggcgtg gtgtgcactg tgtttgctga cgcaaccccc 4200
actggttggg gcattgccac cacctgtcag ctcctttccg ggactttcgc tttccccctc 4260
cctattgcca cggcggaact catcgccgcc tgccttgccc gctgctggac aggggctcgg 4320
ctgttgggca ctgacaattc cgtggtgttg tcggggaagc tgacgtcctt tccatggctg 4380
ctcgcctgtg ttgccacctg gattctgcgc gggacgtcct tctgctacgt cccttcggcc 4440
ctcaatccag cggaccttcc ttcccgcggc ctgctgccgg ctctgcggcc tcttccgcgt 4500
cttcgccttc gccctcagac gagtcggatc tccctttggg ccgcctcccc gcatcgggaa 4560
ttcccgcggt tcgctttaag accaatgact tacaaggcag ctgtagatct tagccacttt 4620
ttaaaagaaa aggggggact ggaagggcta attcactccc aacgaagaca agatctgctt 4680
tttgcttgta ctgggtctct ctggttagac cagatctgag cctgggagct ctctggctaa 4740
ctagggaacc cactgcttaa gcctcaataa agcttgcctt gagtgcttca agtagtgtgt 4800
gcccgtctgt tgtgtgactc tggtaactag agatccctca gaccctttta gtcagtgtgg 4860
aaaatctcta gcagtagtag ttcatgtcat cttattattc agtatttata acttgcaaag 4920
aaatgaatat cagagagtga gaggaacttg tttattgcag cttataatgg ttacaaataa 4980
agcaatagca tcacaaattt cacaaataaa gcattttttt cactgcattc tagttgtggt 5040
ttgtccaaac tcatcaatgt atcttatcat gtctggctct agctatcccg cccctaactc 5100
cgcccatccc gcccctaact ccgcccagtt ccgcccattc tccgccccat ggctgactaa 5160
ttttttttat ttatgcagag gccgaggccg cctcggcctc tgagctattc cagaagtagt 5220
gaggaggctt ttttggaggc ctagggacgt acccaattcg ccctatagtg agtcgtatta 5280
cgcgcgctca ctggccgtcg ttttacaacg tcgtgactgg gaaaaccctg gcgttaccca 5340
acttaatcgc cttgcagcac atcccccttt cgccagctgg cgtaatagcg aagaggcccg 5400
caccgatcgc ccttcccaac agttgcgcag cctgaatggc gaatgggacg cgccctgtag 5460
cggcgcatta agcgcggcgg gtgtggtggt tacgcgcagc gtgaccgcta cacttgccag 5520
cgccctagcg cccgctcctt tcgctttctt cccttccttt ctcgccacgt tcgccggctt 5580

```
tccccgtcaa gctctaaatc gggggctccc tttagggttc cgatttagtg ctttacggca   5640
cctcgacccc aaaaaacttg attagggtga tggttcacgt agtgggccat cgccctgata   5700
gacggttttt cgccctttga cgttggagtc cacgttcttt aatagtggac tcttgttcca   5760
aactggaaca acactcaacc ctatctcggt ctattctttt gatttataag ggattttgcc   5820
gatttcggcc tattggttaa aaaatgagct gatttaacaa aaatttaacg cgaattttaa   5880
caaaatatta acgcttacaa tttaggtggc acttttcggg gaaatgtgcg cggaacccct   5940
atttgtttat ttttctaaat acattcaaat atgtatccgc tcatgagaca ataaccctga   6000
taaatgcttc aataatattg aaaaaggaag agtatgagta ttcaacattt ccgtgtcgcc   6060
cttattccct tttttgcggc attttgcctt cctgtttttg ctcacccaga aacgctggtg   6120
aaagtaaaag atgctgaaga tcagttgggt gcacgagtgg gttacatcga actggatctc   6180
aacagcggta agatccttga gagttttcgc cccgaagaac gttttccaat gatgagcact   6240
tttaaagttc tgctatgtgg cgcggtatta tcccgtattg acgccgggca agagcaactc   6300
ggtcgccgca tacactattc tcagaatgac ttggttgagt actcaccagt cacagaaaag   6360
catcttacgg atggcatgac agtaagagaa ttatgcagtg ctgccataac catgagtgat   6420
aacactgcgg ccaacttact tctgacaacg atcggaggac cgaaggagct aaccgctttt   6480
ttgcacaaca tgggggatca tgtaactcgc cttgatcgtt gggaaccgga gctgaatgaa   6540
gccataccaa acgacgagcg tgacaccacg atgcctgtag caatggcaac aacgttgcgc   6600
aaactattaa ctggcgaact acttactcta gcttcccggc aacaattaat agactggatg   6660
gaggcggata aagttgcagg accacttctg cgctcggccc ttccggctgg ctggtttatt   6720
gctgataaat ctggagccgg tgagcgtggg tctcgcggta tcattgcagc actggggcca   6780
gatggtaagc cctcccgtat cgtagttatc tacacgacgg ggagtcaggc aactatggat   6840
gaacgaaata gacagatcgc tgagataggt gcctcactga ttaagcattg gtaactgtca   6900
gaccaagttt actcatatat actttagatt gatttaaaac ttcattttta atttaaaagg   6960
atctaggtga agatcctttt tgataatctc atgaccaaaa tcccttaacg tgagttttcg   7020
ttccactgag cgtcagaccc cgtagaaaag atcaaaggat cttcttgaga tccttttttt   7080
ctgcgcgtaa tctgctgctt gcaaacaaaa aaaccaccgc taccagcggt ggtttgtttg   7140
ccggatcaag agctaccaac tctttttccg aaggtaactg gcttcagcag agcgcagata   7200
ccaaatactg ttcttctagt gtagccgtag ttaggccacc acttcaagaa ctctgtagca   7260
ccgcctacat acctcgctct gctaatcctg ttaccagtgg ctgctgccag tggcgataag   7320
tcgtgtctta ccgggttgga ctcaagacga tagttaccgg ataaggcgca gcggtcgggc   7380
tgaacggggg gttcgtgcac acagcccagc ttggagcgaa cgacctacac cgaactgaga   7440
tacctacagc gtgagctatg agaaagcgcc acgcttcccg aagagagaaa ggcggacagg   7500
tatccggtaa gcggcagggt cggaacagga gagcgcacga gggagcttcc agggggaaac   7560
gcctggtatc tttatagtcc tgtcgggttt cgccacctct gacttgagcg tcgatttttg   7620
tgatgctcgt caggggggcg gagcctatgg aaaaacgcca gcaacgcggc ctttttacgg   7680
ttcctggcct tttgctggcc ttttgctcac atgttctttc ctgcgttatc ccctgattct   7740
gtggataacc gtattaccgc ctttgagtga gctgataccg ctcgccgcag ccgaacgacc   7800
gagcgcagcg agtcagtgag cgaggaagcg gaagagcgcc caatacgcaa accgcctctc   7860
cccgcgcgtt ggccgattca ttaatgcagc tggcacgaca ggtttcccga ctggaaagcg   7920
ggcagtgagc gcaacgcaat taatgtgagt tagctcactc attaggcacc ccaggcttta   7980
```

```
cactttatgc ttccggctcg tatgttgtgt ggaattgtga gcggataaca atttcacaca   8040

ggaaacagct atgaccatga ttacgccaag cgcgcaatta accctcacta aagggaacaa   8100

aagctggagc tgcaagctt                                                8119
```

<210> SEQ ID NO 5
<211> LENGTH: 7405
<212> TYPE: DNA
<213> ORGANISM: Artificial sequence
<220> FEATURE:
<223> OTHER INFORMATION: lentiviral vector construct encoding for the light chain of gantenerumab (pLV-hPGK-Gant LC-WPRE)

<400> SEQUENCE: 5

```
aatgtagtct tatgcaatac tcttgtagtc ttgcaacatg gtaacgatga gttagcaaca     60

tgccttacaa ggagagaaaa agcaccgtgc atgccgattg gtggaagtaa ggtggtacga    120

tcgtgcctta ttaggaaggc aacagacggg tctgacatgg attggacgaa ccactgaatt    180

gccgcattgc agagatattg tatttaagtg cctagctcga tacataaacg ggtctctctg    240

gttagaccag atctgagcct gggagctctc tggctaacta gggaacccac tgcttaagcc    300

tcaataaagc ttgccttgag tgcttcaagt agtgtgtgcc cgtctgttgt gtgactctgg    360

taactagaga tccctcagac ccttttagtc agtgtggaaa atctctagca gtggcgcccg    420

aacagggact tgaaagcgaa agggaaacca gaggagctct ctcgacgcag gactcggctt    480

gctgaagcgc gcacggcaag aggcgagggg cggcgactgg tgagtacgcc aaaaattttg    540

actagcggag gctagaagga gagagatggg tgcgagagcg tcagtattaa gcgggggaga    600

attagatcgc gatgggaaaa aattcggtta aggccagggg gaaagaaaaa atataaatta    660

aaacatatag tatgggcaag cagggagcta gaacgattcg cagttaatcc tggcctgtta    720

gaaacatcag aaggctgtag acaaatactg ggacagctac aaccatccct tcagacagga    780

tcagaagaac ttagatcatt atataataca gtagcaaccc tctattgtgt gcatcaaagg    840

atagagataa aagacaccaa ggaagcttta gacaagatag aggaagagca aaacaaaagt    900

aagaccaccg cacagcaagc ggccgctgat cttcagacct ggaggaggag atatgaggga    960

caattggaga agtgaattat ataaatataa agtagtaaaa attgaaccat taggagtagc   1020

acccaccaag gcaaagagaa gagtggtgca gagagaaaaa agagcagtgg gaataggagc   1080

tttgttcctt gggttcttgg gagcagcagg aagcactatg ggcgcagcgt caatgacgct   1140

gacggtacag gccagacaat tattgtctgg tatagtgcag cagcagaaca atttgctgag   1200

ggctattgag gcgcaacagc atctgttgca actcacagtc tggggcatca agcagctcca   1260

ggcaagaatc ctggctgtgg aaagatacct aaaggatcaa cagctcctgg ggatttgggg   1320

ttgctctgga aaactcattt gcaccactgc tgtgccttgg aatgctagtt ggagtaataa   1380

atctctggaa cagatttgga atcacacgac ctggatggag tgggacagag aaattaacaa   1440

ttacacaagc ttaatacact ccttaattga agaatcgcaa aaccagcaag aaaagaatga   1500

acaagaatta ttggaattag ataaatgggc aagtttgtgg aattggttta acataacaaa   1560

ttggctgtgg tatataaaat tattcataat gatagtagga ggcttggtag gtttaagaat   1620

agtttttgct gtactttcta tagtgaatag agttaggcag ggatattcac cattatcgtt   1680

tcagacccac ctcccaaccc cgaggggacc cgacaggccc gaaggaatag aagaagaagg   1740

tggagagaga gacagagaca gatccattcg attagtgaac ggatctcgac ggtatcgcta   1800

gcttttaaaa gaaaaggggg gattgggggg tacagtgcag gggaaagaat agtagacata   1860
```

```
atagcaacag acatacaaac taaagaatta caaaaacaaa ttacaaaaat tcaaaatttt   1920
actagtgatt atcggatcaa ctttgtatag aaaagttggg gttgcgcctt ttccaaggca   1980
gccctgggtt tgcgcaggga cgcggctgct ctgggcgtgg ttccgggaaa cgcagcggcg   2040
ccgaccctgg gtctcgcaca ttcttcacgt ccgttcgcag cgtcacccgg atcttcgccg   2100
ctacccttgt gggcccccg gcgacgcttc ctgctccgcc cctaagtcgg gaaggttcct   2160
tgcggttcgc ggcgtgccgg acgtgacaaa cggaagccgc acgtctcact agtaccctcg   2220
cagacggaca gcgccaggga gcaatggcag cgcgccgacc gcgatgggct gtggccaata   2280
gcggctgctc agcagggcgc gccgagagca gcggccggga aggggcggtg cgggaggcgg   2340
ggtgtggggc ggtagtgtgg gccctgttcc tgcccgcgcg gtgttccgca ttctgcaagc   2400
ctccggagcg cacgtcggca gtcggctccc tcgttgaccg aatcaccgac ctctctcccc   2460
aggcaagttt gtacaaaaaa gcaggctgcc accatgaaat acctattgcc tacggcagcc   2520
gctggattgt tattactcgc ggcccagccg gccatggccg acatcgtgct gacccagagc   2580
cccgccaccc tgagcctgag ccccggcgag agagccaccc tgagctgcag agccagccag   2640
agcgtgagca gcagctacct ggcctggtac cagcagaagc ccggccaggc ccccagactg   2700
ctgatctacg gcgccagcag cagagccacc ggcgtgcccg ccagattcag cggcagcggc   2760
agcggcaccg acttcaccct gaccatcagc agcctggagc ccgaggactt cgccacctac   2820
tactgcctgc agatctacaa catgcccatc accttcggcc agggcaccaa ggtggagatc   2880
aagagaaccg tggccgcccc cagcgtgttc atcttccccc ccagcgacga gcagctgaag   2940
agcggcaccg ccagcgtggt gtgcctgctg aacaacttct accccagaga ggccaaggtg   3000
cagtggaagg tggacaacgc cctgcagagc ggcaacagcc aggagagcgt gaccgagcag   3060
gacagcaagg acagcaccta cagcctgagc agcaccctga ccctgagcaa ggccgactac   3120
gagaagcaca aggtgtacgc ctgcgaggtg acccaccagg gcctgagcag ccccgtgacc   3180
aagagcttca acagaggcga gtgctgaacc cagctttctt gtacaaagtg gtgataatcg   3240
aattccgata atcaacctct ggattacaaa atttgtgaaa gattgactgg tattcttaac   3300
tatgttgctc cttttacgct atgtggatac gctgctttaa tgcctttgta tcatgctatt   3360
gcttcccgta tggctttcat tttctcctcc ttgtataaat cctggttgct gtctctttat   3420
gaggagttgt ggcccgttgt caggcaacgt ggcgtggtgt gcactgtgtt tgctgacgca   3480
acccccactg gttggggcat tgccaccacc tgtcagctcc tttccgggac tttcgctttc   3540
cccctcccta ttgccacggc ggaactcatc gccgcctgcc ttgcccgctg ctggacaggg   3600
gctcggctgt tgggcactga caattccgtg gtgttgtcgg ggaagctgac gtcctttcca   3660
tggctgctcg cctgtgttgc cacctggatt ctgcgcggga cgtccttctg ctacgtccct   3720
tcggccctca atccagcgga ccttccttcc cgcggcctgc tgccggctct gcggcctctt   3780
ccgcgtcttc gccttcgccc tcagacgagt cggatctccc tttgggccgc ctccccgcat   3840
cgggaattcc cgcggttcgc tttaagacca atgacttaca aggcagctgt agatcttagc   3900
cactttttaa aagaaaaggg gggactggaa gggctaattc actcccaacg aagacaagat   3960
ctgcttttttg cttgtactgg gtctctctgg ttagaccaga tctgagcctg ggagctctct   4020
ggctaactag ggaacccact gcttaagcct caataaagct tgccttgagt gcttcaagta   4080
gtgtgtgccc gtctgttgtg tgactctggt aactagagat ccctcagacc cttttagtca   4140
gtgtggaaaa tctctagcag tagtagttca tgtcatctta ttattcagta tttataactt   4200
```

```
gcaaagaaat gaatatcaga gagtgagagg aacttgttta ttgcagctta taatggttac   4260
aaataaagca atagcatcac aaatttcaca aataaagcat ttttttcact gcattctagt   4320
tgtggtttgt ccaaactcat caatgtatct tatcatgtct ggctctagct atcccgcccc   4380
taactccgcc catcccgccc ctaactccgc ccagttccgc ccattctccg ccccatggct   4440
gactaatttt ttttatttat gcagaggccg aggccgcctc ggcctctgag ctattccaga   4500
agtagtgagg aggctttttt ggaggcctag ggacgtaccc aattcgccct atagtgagtc   4560
gtattacgcg cgctcactgg ccgtcgtttt acaacgtcgt gactgggaaa accctggcgt   4620
tacccaactt aatcgccttg cagcacatcc ccctttcgcc agctggcgta atagcgaaga   4680
ggcccgcacc gatcgccctt cccaacagtt gcgcagcctg aatggcgaat gggacgcgcc   4740
ctgtagcggc gcattaagcg cggcgggtgt ggtggttacg cgcagcgtga ccgctacact   4800
tgccagcgcc ctagcgcccg ctcctttcgc tttcttccct tcctttctcg ccacgttcgc   4860
cggctttccc cgtcaagctc taaatcgggg gctcccttta gggttccgat ttagtgcttt   4920
acggcacctc gaccccaaaa aacttgatta gggtgatggt tcacgtagtg ggccatcgcc   4980
ctgatagacg gtttttcgcc ctttgacgtt ggagtccacg ttctttaata gtggactctt   5040
gttccaaact ggaacaacac tcaaccctat ctcggtctat tcttttgatt tataagggat   5100
tttgccgatt tcggcctatt ggttaaaaaa tgagctgatt taacaaaaat ttaacgcgaa   5160
ttttaacaaa atattaacgc ttacaattta ggtggcactt ttcggggaaa tgtgcgcgga   5220
acccctattt gtttattttt ctaaatacat tcaaatatgt atccgctcat gagacaataa   5280
ccctgataaa tgcttcaata atattgaaaa aggaagagta tgagtattca acatttccgt   5340
gtcgccctta ttcccttttt tgcggcattt tgccttcctg tttttgctca cccagaaacg   5400
ctggtgaaag taaaagatgc tgaagatcag ttgggtgcac gagtgggtta catcgaactg   5460
gatctcaaca gcggtaagat ccttgagagt tttcgccccg aagaacgttt tccaatgatg   5520
agcactttta aagttctgct atgtggcgcg gtattatccc gtattgacgc cgggcaagag   5580
caactcggtc gccgcataca ctattctcag aatgacttgg ttgagtactc accagtcaca   5640
gaaaagcatc ttacggatgg catgacagta agagaattat gcagtgctgc cataaccatg   5700
agtgataaca ctgcggccaa cttacttctg acaacgatcg gaggaccgaa ggagctaacc   5760
gcttttttgc acaacatggg ggatcatgta actcgccttg atcgttggga accggagctg   5820
aatgaagcca taccaaacga cgagcgtgac accacgatgc ctgtagcaat ggcaacaacg   5880
ttgcgcaaac tattaactgg cgaactactt actctagctt cccggcaaca attaatagac   5940
tggatggagg cggataaagt tgcaggacca cttctgcgct cggcccttcc ggctggctgg   6000
tttattgctg ataaatctgg agccggtgag cgtgggtctc gcggtatcat tgcagcactg   6060
gggccagatg gtaagccctc ccgtatcgta gttatctaca cgacggggag tcaggcaact   6120
atggatgaac gaaatagaca gatcgctgag ataggtgcct cactgattaa gcattggtaa   6180
ctgtcagacc aagtttactc atatatactt tagattgatt taaaacttca tttttaattt   6240
aaaaggatct aggtgaagat cctttttgat aatctcatga ccaaaatccc ttaacgtgag   6300
ttttcgttcc actgagcgtc agaccccgta gaaaagatca aaggatcttc ttgagatcct   6360
ttttttctgc gcgtaatctg ctgcttgcaa acaaaaaaac caccgctacc agcggtggtt   6420
tgtttgccgg atcaagagct accaactctt tttccgaagg taactggctt cagcagagcg   6480
cagataccaa atactgttct tctagtgtag ccgtagttag gccaccactt caagaactct   6540
gtagcaccgc ctacatacct cgctctgcta atcctgttac cagtggctgc tgccagtggc   6600
```

```
gataagtcgt gtcttaccgg gttggactca agacgatagt taccggataa ggcgcagcgg   6660

tcgggctgaa cggggggttc gtgcacacag cccagcttgg agcgaacgac ctacaccgaa   6720

ctgagatacc tacagcgtga gctatgagaa agcgccacgc ttcccgaaga gagaaaggcg   6780

gacaggtatc cggtaagcgg cagggtcgga acaggagagc gcacgaggga gcttccaggg   6840

ggaaacgcct ggtatcttta tagtcctgtc gggtttcgcc acctctgact tgagcgtcga   6900

tttttgtgat gctcgtcagg ggggcggagc ctatggaaaa acgccagcaa cgcggccttt   6960

ttacggttcc tggccttttg ctggcctttt gctcacatgt tctttcctgc gttatcccct   7020

gattctgtgg ataaccgtat taccgccttt gagtgagctg ataccgctcg ccgcagccga   7080

acgaccgagc gcagcgagtc agtgagcgag gaagcggaag agcgcccaat acgcaaaccg   7140

cctctccccg cgcgttggcc gattcattaa tgcagctggc acgacaggtt tcccgactgg   7200

aaagcgggca gtgagcgcaa cgcaattaat gtgagttagc tcactcatta ggcaccccag   7260

gctttacact ttatgcttcc ggctcgtatg ttgtgtggaa ttgtgagcgg ataacaattt   7320

cacacaggaa acagctatga ccatgattac gccaagcgcg caattaaccc tcactaaagg   7380

gaacaaaagc tggagctgca agctt                                        7405

<210> SEQ ID NO 6
<211> LENGTH: 7398
<212> TYPE: DNA
<213> ORGANISM: Artificial sequence
<220> FEATURE:
<223> OTHER INFORMATION: lentiviral vector construct encoding for the
      light chain of Rituximab (pLV-hPGK-ritux-LC-WPRE)

<400> SEQUENCE: 6

atgtagtctt atgcaatact cttgtagtct tgcaacatgg taacgatgag ttagcaacat     60

gccttacaag gagagaaaaa gcaccgtgca tgccgattgg tggaagtaag gtggtacgat    120

cgtgccttat taggaaggca acagacgggt ctgacatgga ttggacgaac cactgaattg    180

ccgcattgca gagatattgt atttaagtgc ctagctcgat acataaacgg gtctctctgg    240

ttagaccaga tctgagcctg ggagctctct ggctaactag ggaacccact gcttaagcct    300

caataaagct tgccttgagt gcttcaagta gtgtgtgccc gtctgttgtg tgactctggt    360

aactagagat ccctcagacc cttttagtca gtgtggaaaa tctctagcag tggcgcccga    420

acagggactt gaaagcgaaa gggaaaccag aggagctctc tcgacgcagg actcggcttg    480

ctgaagcgcg cacggcaaga ggcgaggggc ggcgactggt gagtacgcca aaaattttga    540

ctagcggagg ctagaaggag agagatgggt gcgagagcgt cagtattaag cgggggagaa    600

ttagatcgcg atgggaaaaa attcggttaa ggccaggggg aaagaaaaaa tataaattaa    660

aacatatagt atgggcaagc agggagctag aacgattcgc agttaatcct ggcctgttag    720

aaacatcaga aggctgtaga caaatactgg gacagctaca accatccctt cagacaggat    780

cagaagaact tagatcatta tataatacag tagcaaccct ctattgtgtg catcaaagga    840

tagagataaa agacaccaag gaagctttag acaagataga ggaagagcaa aacaaaagta    900

agaccaccgc acagcaagcg gccgctgatc ttcagacctg gaggaggaga tatgagggac    960

aattggagaa gtgaattata taaatataaa gtagtaaaaa ttgaaccatt aggagtagca   1020

cccaccaagg caaagagaag agtggtgcag agagaaaaaa gagcagtggg aataggagct   1080

ttgttccttg ggttcttggg agcagcagga agcactatgg gcgcagcgtc aatgacgctg   1140

acggtacagg ccagacaatt attgtctggt atagtgcagc agcagaacaa tttgctgagg   1200
```

```
gctattgagg cgcaacagca tctgttgcaa ctcacagtct ggggcatcaa gcagctccag   1260
gcaagaatcc tggctgtgga aagataccta aaggatcaac agctcctggg gatttggggt   1320
tgctctggaa aactcatttg caccactgct gtgccttgga atgctagttg gagtaataaa   1380
tctctggaac agatttggaa tcacacgacc tggatggagt gggacagaga aattaacaat   1440
tacacaagct taatacactc cttaattgaa gaatcgcaaa accagcaaga aaagaatgaa   1500
caagaattat tggaattaga taaatgggca agtttgtgga attggtttaa cataacaaat   1560
tggctgtggt atataaaatt attcataatg atagtaggag gcttggtagg tttaagaata   1620
gtttttgctg tactttctat agtgaataga gttaggcagg gatattcacc attatcgttt   1680
cagacccacc tcccaacccc gaggggaccc gacaggcccg aaggaataga agaagaaggt   1740
ggagagagag acagagacag atccattcga ttagtgaacg gatctcgacg gtatcgctag   1800
cttttaaaag aaaagggggg attggggggt acagtgcagg ggaaagaata gtagacataa   1860
tagcaacaga catacaaact aaagaattac aaaaacaaat tacaaaaatt caaaatttta   1920
ctagtgatta tcggatcaac tttgtataga aaagttgggg ttgcgccttt tccaaggcag   1980
ccctgggttt gcgcagggac gcggctgctc tgggcgtggt tccgggaaac gcagcggcgc   2040
cgaccctggg tctcgcacat tcttcacgtc cgttcgcagc gtcacccgga tcttcgccgc   2100
tacccttgtg ggccccccgg cgacgcttcc tgctccgccc ctaagtcggg aaggttcctt   2160
gcggttcgcg gcgtgccgga cgtgacaaac ggaagccgca cgtctcacta gtaccctcgc   2220
agacggacag cgccagggag caatggcagc gcgccgaccg cgatgggctg tggccaatag   2280
cggctgctca gcagggcgcg ccgagagcag cggccgggaa ggggcggtgc gggaggcggg   2340
gtgtggggcg gtagtgtggg ccctgttcct gcccgcgcgg tgttccgcat tctgcaagcc   2400
tccggagcgc acgtcggcag tcggctccct cgttgaccga atcaccgacc tctctcccca   2460
ggcaagtttg tacaaaaaag caggctgcca ccatgaaata cctattgcct acggcagccg   2520
ctggattgtt attactcgcg gcccagccgg ccatggccca gatcgtgctg agccagtctc   2580
ctgccatcct gagtgctagc cctggcgaga aagtgaccat gacctgtaga gccagcagca   2640
gcgtgtccta catccactgg ttccagcaga agcctggcag cagccctaag ccttggatct   2700
acgccacaag caatctggcc agcggcgtgc cagtcagatt ttctggctct ggcagcggca   2760
ccagctacag cctgacaatc tctagagtgg aagccgagga cgccgccacc tactattgtc   2820
agcagtggac cagcaatcct cctacctttg gcggaggcac caagctggaa atcaagagaa   2880
ccgtcgccgc tcctagcgtg ttcatcttcc caccttccga cgagcagctg aagtctggca   2940
cagcctctgt cgtgtgcctg ctgaacaact tctaccccag agaagccaag gtgcagtgga   3000
aggtggacaa cgccctgcag agcggcaata gccaagagag cgtgaccgag caggacagca   3060
aggactctac ctacagcctg agcagcaccc tgacactgag caaggccgac tacgagaagc   3120
acaaagtgta cgcctgcgaa gtgacccacc agggcctttc tagccctgtg accaagagct   3180
tcaaccgggg cgagtgttga acccagcttt cttgtacaaa gtggtgataa tcgaattccg   3240
ataatcaacc tctggattac aaaatttgtg aaagattgac tggtattctt aactatgttg   3300
ctccttttac gctatgtgga tacgctgctt taatgccttt gtatcatgct attgcttccc   3360
gtatggcttt cattttctcc tccttgtata aatcctggtt gctgtctctt tatgaggagt   3420
tgtggcccgt tgtcaggcaa cgtggcgtgg tgtgcactgt gtttgctgac gcaaccccca   3480
ctggttgggg cattgccacc acctgtcagc tcctttccgg gactttcgct ttccccctcc   3540
```

```
ctattgccac ggcggaactc atcgccgcct gccttgcccg ctgctggaca ggggctcggc   3600
tgttgggcac tgacaattcc gtggtgttgt cggggaagct gacgtccttt ccatggctgc   3660
tcgcctgtgt tgccacctgg attctgcgcg ggacgtcctt ctgctacgtc ccttcggccc   3720
tcaatccagc ggaccttcct tcccgcggcc tgctgccggc tctgcggcct cttccgcgtc   3780
ttcgccttcg ccctcagacg agtcggatct ccctttgggc cgcctccccg catcgggaat   3840
tcccgcggtt cgctttaaga ccaatgactt acaaggcagc tgtagatctt agccactttt   3900
taaaagaaaa ggggggactg gaagggctaa ttcactccca acgaagacaa gatctgcttt   3960
ttgcttgtac tgggtctctc tggttagacc agatctgagc ctgggagctc tctggctaac   4020
tagggaaccc actgcttaag cctcaataaa gcttgccttg agtgcttcaa gtagtgtgtg   4080
cccgtctgtt gtgtgactct ggtaactaga gatccctcag acccttttag tcagtgtgga   4140
aaatctctag cagtagtagt tcatgtcatc ttattattca gtatttataa cttgcaaaga   4200
aatgaatatc agagagtgag aggaacttgt ttattgcagc ttataatggt tacaaataaa   4260
gcaatagcat cacaaatttc acaaataaag catttttttc actgcattct agttgtggtt   4320
tgtccaaact catcaatgta tcttatcatg tctggctcta gctatcccgc ccctaactcc   4380
gcccatcccg cccctaactc cgcccagttc cgcccattct ccgccccatg gctgactaat   4440
ttttttatt tatgcagagg ccgaggccgc ctcggcctct gagctattcc agaagtagtg   4500
aggaggcttt tttggaggcc tagggacgta cccaattcgc cctatagtga gtcgtattac   4560
gcgcgctcac tggccgtcgt tttacaacgt cgtgactggg aaaaccctgg cgttacccaa   4620
cttaatcgcc ttgcagcaca tccccctttc gccagctggc gtaatagcga agaggcccgc   4680
accgatcgcc cttcccaaca gttgcgcagc ctgaatggcg aatgggacgc gccctgtagc   4740
ggcgcattaa gcgcggcggg tgtggtggtt acgcgcagcg tgaccgctac acttgccagc   4800
gccctagcgc ccgctccttt cgctttcttc ccttcctttc tcgccacgtt cgccggcttt   4860
ccccgtcaag ctctaaatcg ggggctccct ttagggttcc gatttagtgc tttacggcac   4920
ctcgacccca aaaaacttga ttagggtgat ggttcacgta gtgggccatc gccctgatag   4980
acggtttttc gccctttgac gttggagtcc acgttcttta atagtggact cttgttccaa   5040
actggaacaa cactcaaccc tatctcggtc tattcttttg atttataagg gattttgccg   5100
atttcggcct attggttaaa aaatgagctg atttaacaaa aatttaacgc gaattttaac   5160
aaaatattaa cgcttacaat ttaggtggca cttttcgggg aaatgtgcgc ggaaccccta   5220
tttgtttatt tttctaaata cattcaaata tgtatccgct catgagacaa taaccctgat   5280
aaatgcttca ataatattga aaaaggaaga gtatgagtat tcaacatttc cgtgtcgccc   5340
ttattccctt ttttgcggca ttttgccttc ctgtttttgc tcacccagaa acgctggtga   5400
aagtaaaaga tgctgaagat cagttgggtg cacgagtggg ttacatcgaa ctggatctca   5460
acagcggtaa gatccttgag agttttcgcc ccgaagaacg ttttccaatg atgagcactt   5520
ttaaagttct gctatgtggc gcggtattat cccgtattga cgccgggcaa gagcaactcg   5580
gtcgccgcat acactattct cagaatgact tggttgagta ctcaccagtc acagaaaagc   5640
atcttacgga tggcatgaca gtaagagaat tatgcagtgc tgccataacc atgagtgata   5700
acactgcggc caacttactt ctgacaacga tcggaggacc gaaggagcta accgcttttt   5760
tgcacaacat gggggatcat gtaactcgcc ttgatcgttg ggaaccggag ctgaatgaag   5820
ccataccaaa cgacgagcgt gacaccacga tgcctgtagc aatggcaaca acgttgcgca   5880
aactattaac tggcgaacta cttactctag cttcccggca acaattaata gactggatgg   5940
```

```
aggcggataa agttgcagga ccacttctgc gctcggccct tccggctggc tggtttattg   6000
ctgataaatc tggagccggt gagcgtgggt ctcgcggtat cattgcagca ctggggccag   6060
atggtaagcc ctcccgtatc gtagttatct acacgacggg gagtcaggca actatggatg   6120
aacgaaatag acagatcgct gagataggtg cctcactgat taagcattgg taactgtcag   6180
accaagttta ctcatatata ctttagattg atttaaaact tcatttttaa tttaaaagga   6240
tctaggtgaa gatccttttt gataatctca tgaccaaaat cccttaacgt gagttttcgt   6300
tccactgagc gtcagacccc gtagaaaaga tcaaaggatc ttcttgagat cctttttttc   6360
tgcgcgtaat ctgctgcttg caaacaaaaa aaccaccgct accagcggtg gtttgtttgc   6420
cggatcaaga gctaccaact ctttttccga aggtaactgg cttcagcaga gcgcagatac   6480
caaatactgt tcttctagtg tagccgtagt taggccacca cttcaagaac tctgtagcac   6540
cgcctacata cctcgctctg ctaatcctgt taccagtggc tgctgccagt ggcgataagt   6600
cgtgtcttac cgggttggac tcaagacgat agttaccgga taaggcgcag cggtcgggct   6660
gaacgggggg ttcgtgcaca cagcccagct tggagcgaac gacctacacc gaactgagat   6720
acctacagcg tgagctatga gaaagcgcca cgcttcccga agagagaaag gcggacaggt   6780
atccggtaag cggcagggtc ggaacaggag agcgcacgag ggagcttcca gggggaaacg   6840
cctggtatct ttatagtcct gtcgggtttc gccacctctg acttgagcgt cgatttttgt   6900
gatgctcgtc aggggggcgg agcctatgga aaaacgccag caacgcggcc tttttacggt   6960
tcctggcctt ttgctggcct tttgctcaca tgttctttcc tgcgttatcc cctgattctg   7020
tggataaccg tattaccgcc tttgagtgag ctgataccgc tcgccgcagc cgaacgaccg   7080
agcgcagcga gtcagtgagc gaggaagcgg aagagcgccc aatacgcaaa ccgcctctcc   7140
ccgcgcgttg gccgattcat taatgcagct ggcacgacag gtttcccgac tggaaagcgg   7200
gcagtgagcg caacgcaatt aatgtgagtt agctcactca ttaggcaccc caggctttac   7260
actttatgct tccggctcgt atgttgtgtg gaattgtgag cggataacaa tttcacacag   7320
gaaacagcta tgaccatgat tacgccaagc gcgcaattaa ccctcactaa agggaacaaa   7380
agctggagct gcaagctt                                                 7398
```

<210> SEQ ID NO 7
<211> LENGTH: 8104
<212> TYPE: DNA
<213> ORGANISM: Artificial sequence
<220> FEATURE:
<223> OTHER INFORMATION: lentiviral vector construct encoding for the heavy chain of Rituximab (pLV-hPGK-ritux-HC-WPRE)

<400> SEQUENCE: 7

```
aatgtagtct tatgcaatac tcttgtagtc ttgcaacatg gtaacgatga gttagcaaca     60
tgccttacaa ggagagaaaa agcaccgtgc atgccgattg gtggaagtaa ggtggtacga    120
tcgtgcctta ttaggaaggc aacagacggg tctgacatgg attggacgaa ccactgaatt    180
gccgcattgc agagatattg tatttaagtg cctagctcga tacataaacg ggtctctctg    240
gttagaccag atctgagcct gggagctctc tggctaacta gggaacccac tgcttaagcc    300
tcaataaagc ttgccttgag tgcttcaagt agtgtgtgcc cgtctgttgt gtgactctgg    360
taactagaga tccctcagac ccttttagtc agtgtggaaa atctctagca gtggcgcccg    420
aacagggact tgaaagcgaa agggaaacca gaggagctct ctcgacgcag gactcggctt    480
gctgaagcgc gcacggcaag aggcgagggg cggcgactgg tgagtacgcc aaaaattttg    540
```

```
actagcggag gctagaagga gagagatggg tgcgagagcg tcagtattaa gcgggggaga    600
attagatcgc gatgggaaaa aattcggtta aggccagggg gaaagaaaaa atataaatta    660
aaacatatag tatgggcaag cagggagcta gaacgattcg cagttaatcc tggcctgtta    720
gaaacatcag aaggctgtag acaaatactg ggacagctac aaccatccct tcagacagga    780
tcagaagaac ttagatcatt atataataca gtagcaaccc tctattgtgt gcatcaaagg    840
atagagataa aagacaccaa ggaagcttta gacaagatag aggaagagca aaacaaaagt    900
aagaccaccg cacagcaagc ggccgctgat cttcagacct ggaggaggag atatgaggga    960
caattggaga agtgaattat ataaatataa agtagtaaaa attgaaccat taggagtagc   1020
acccaccaag gcaaagagaa gagtggtgca gagagaaaaa agagcagtgg gaataggagc   1080
tttgttcctt gggttcttgg gagcagcagg aagcactatg ggcgcagcgt caatgacgct   1140
gacggtacag gccagacaat tattgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agtttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcgcta   1800
gcttttaaaa gaaaaggggg gattgggggg tacagtgcag gggaaagaat agtagacata   1860
atagcaacag acatacaaac taaagaatta caaaaacaaa ttacaaaaat tcaaaatttt   1920
actagtgatt atcggatcaa ctttgtatag aaaagttggg gttgcgcctt ttccaaggca   1980
gccctgggtt tgcgcaggga cgcggctgct ctgggcgtgg ttccgggaaa cgcagcggcg   2040
ccgaccctgg gtctcgcaca ttcttcacgt ccgttcgcag cgtcacccgg atcttcgccg   2100
ctacccttgt gggccccccg gcgacgcttc ctgctccgcc cctaagtcgg gaaggttcct   2160
tgcggttcgc ggcgtgccgg acgtgacaaa cggaagccgc acgtctcact agtaccctcg   2220
cagacggaca gcgccaggga gcaatggcag cgcgccgacc gcgatgggct gtggccaata   2280
gcggctgctc agcagggcgc gccgagagca gcggccggga aggggcggtg cgggaggcgg   2340
ggtgtggggc ggtagtgtgg gccctgttcc tgcccgcgcg gtgttccgca ttctgcaagc   2400
ctccggagcg cacgtcggca gtcggctccc tcgttgaccg aatcaccgac ctctctcccc   2460
aggcaagttt gtacaaaaaa gcaggctgcc accatggagt ttgggctgag ctgggttttc   2520
ctcgttgctc tttttagagg tgtccagtgt caggttcagc tgcagcagcc tggcgccgaa   2580
cttgtgaaac ctggcgcctc tgtgaagatg agctgcaagg ccagcggcta caccttcacc   2640
agctacaaca tgcactgggt caagcagacc cctggcagag gcctggaatg gatcggagcc   2700
atctatcccg gcaacggcga cacctcctac aaccagaagt tcaagggcaa agccacactg   2760
accgccgaca agagcagcag cacagcctac atgcagctgt ccagcctgac cagcgaagat   2820
agcgccgtgt actactgcgc cagaagcacc tattacggcg gcgactggta cttcaacgtg   2880
```

-continued

```
tggggagctg gcaccaccgt gacagtgtct gccgcctcta caaagggccc tagcgttttc   2940
ccactggctc ccagcagcaa gagcacatct ggtggaacag ccgctctggg ctgcctggtc   3000
aaggattact ttcccgagcc tgtgaccgtg tcctggaatt ctggcgctct gacaagcggc   3060
gtgcacacct ttccagcagt gctgcaaagc agcggcctgt actctctgag cagcgtggtc   3120
acagtgccta gctctagcct gggcacccag acctacatct gcaatgtgaa ccacaagcct   3180
agcaacacca aggtggacaa gaaggtggaa cccaagagct gcgacaagac ccacacctgt   3240
cctccatgtc ctgctccaga actgctcggc ggaccttccg tgttcctgtt tcctccaaag   3300
cctaaggaca ccctgatgat cagcagaacc cctgaagtga cctgcgtggt ggtggatgtg   3360
tcccacgagg atcccgaagt gaagttcaat tggtacgtgg acggcgtgga agtgcacaac   3420
gccaagacca agcctagaga ggaacagtac aacagcacct acagagtggt gtccgtgctg   3480
accgtgctgc accaggattg gctgaacggc aaagagtaca agtgcaaggt gtccaacaag   3540
gccctgcctg ctcctatcga gaaaaccatc agcaaggcca agggccagcc tagggaaccc   3600
caggtttaca cactgcctcc aagcagggac gagctgacca agaatcaggt gtccctgacc   3660
tgtctcgtga agggcttcta cccctccgat atcgccgtgg aatgggagag caatggccag   3720
cctgagaaca actacaagac aacccctcct gtgctggact ccgacggctc attcttcctg   3780
tacagcaagc tgacagtgga caagtccaga tggcagcagg gcaacgtgtt ctcctgcagc   3840
gtgatgcacg aggccctgca caaccactac acccagaaaa gcctgtctct gagccccggc   3900
aaatagaccc agctttcttg tacaaagtgg tgataatcga attccgataa tcaacctctg   3960
gattacaaaa tttgtgaaag attgactggt attcttaact atgttgctcc ttttacgcta   4020
tgtggatacg ctgctttaat gcctttgtat catgctattg cttcccgtat ggctttcatt   4080
ttctcctcct tgtataaatc ctggttgctg tctctttatg aggagttgtg gcccgttgtc   4140
aggcaacgtg gcgtggtgtg cactgtgttt gctgacgcaa cccccactgg ttggggcatt   4200
gccaccacct gtcagctcct ttccgggact ttcgctttcc ccctccctat tgccacggcg   4260
gaactcatcg ccgcctgcct tgcccgctgc tggacagggg ctcggctgtt gggcactgac   4320
aattccgtgg tgttgtcggg gaagctgacg tcctttccat ggctgctcgc ctgtgttgcc   4380
acctggattc tgcgcgggac gtccttctgc tacgtccctt cggccctcaa tccagcggac   4440
cttccttccc gcggcctgct gccggctctg cggcctcttc cgcgtcttcg ccttcgccct   4500
cagacgagtc ggatctccct ttgggccgcc tccccgcatc gggaattccc gcggttcgct   4560
ttaagaccaa tgacttacaa ggcagctgta gatcttagcc actttttaaa agaaaagggg   4620
ggactggaag ggctaattca ctcccaacga agacaagatc tgcttttttgc ttgtactggg   4680
tctctctggt tagaccagat ctgagcctgg gagctctctg gctaactagg gaacccactg   4740
cttaagcctc aataaagctt gccttgagtg cttcaagtag tgtgtgcccg tctgttgtgt   4800
gactctggta actagagatc cctcagaccc ttttagtcag tgtggaaaat ctctagcagt   4860
agtagttcat gtcatcttat tattcagtat ttataacttg caaagaaatg aatatcagag   4920
agtgagagga acttgtttat tgcagcttat aatggttaca aataaagcaa tagcatcaca   4980
aatttcacaa ataaagcatt tttttcactg cattctagtt gtggtttgtc caaactcatc   5040
aatgtatctt atcatgtctg gctctagcta tcccgcccct aactccgccc atcccgcccc   5100
taactccgcc cagttccgcc cattctccgc cccatggctg actaattttt tttatttatg   5160
cagaggccga ggccgcctcg gcctctgagc tattccagaa gtagtgagga ggcttttttg   5220
gaggcctagg gacgtaccca attcgcccta tagtgagtcg tattacgcgc gctcactggc   5280
```

```
cgtcgtttta caacgtcgtg actgggaaaa ccctggcgtt acccaactta atcgccttgc   5340
agcacatccc cctttcgcca gctggcgtaa tagcgaagag gcccgcaccg atcgcccttc   5400
ccaacagttg cgcagcctga atggcgaatg ggacgcgccc tgtagcggcg cattaagcgc   5460
ggcgggtgtg gtggttacgc gcagcgtgac cgctacactt gccagcgccc tagcgcccgc   5520
tcctttcgct ttcttccctt cctttctcgc cacgttcgcc ggctttcccc gtcaagctct   5580
aaatcggggg ctccctttag ggttccgatt tagtgcttta cggcacctcg accccaaaaa   5640
acttgattag ggtgatggtt cacgtagtgg gccatcgccc tgatagacgg tttttcgccc   5700
tttgacgttg gagtccacgt tctttaatag tggactcttg ttccaaactg gaacaacact   5760
caaccctatc tcggtctatt cttttgattt ataagggatt ttgccgattt cggcctattg   5820
gttaaaaaat gagctgattt aacaaaaatt taacgcgaat tttaacaaaa tattaacgct   5880
tacaatttag gtggcacttt tcggggaaat gtgcgcggaa cccctatttg tttatttttc   5940
taaatacatt caaatatgta tccgctcatg agacaataac cctgataaat gcttcaataa   6000
tattgaaaaa ggaagagtat gagtattcaa catttccgtg tcgcccttat tccctttttt   6060
gcggcatttt gccttcctgt ttttgctcac ccagaaacgc tggtgaaagt aaaagatgct   6120
gaagatcagt tgggtgcacg agtgggttac atcgaactgg atctcaacag cggtaagatc   6180
cttgagagtt ttcgccccga agaacgtttt ccaatgatga gcacttttaa agttctgcta   6240
tgtggcgcgg tattatcccg tattgacgcc gggcaagagc aactcggtcg ccgcatacac   6300
tattctcaga atgacttggt tgagtactca ccagtcacag aaaagcatct tacggatggc   6360
atgacagtaa gagaattatg cagtgctgcc ataaccatga gtgataacac tgcggccaac   6420
ttacttctga caacgatcgg aggaccgaag gagctaaccg cttttttgca caacatgggg   6480
gatcatgtaa ctcgccttga tcgttgggaa ccggagctga atgaagccat accaaacgac   6540
gagcgtgaca ccacgatgcc tgtagcaatg gcaacaacgt tgcgcaaact attaactggc   6600
gaactactta ctctagcttc ccggcaacaa ttaatagact ggatggaggc ggataaagtt   6660
gcaggaccac ttctgcgctc ggcccttccg gctggctggt ttattgctga taaatctgga   6720
gccggtgagc gtgggtctcg cggtatcatt gcagcactgg ggccagatgg taagccctcc   6780
cgtatcgtag ttatctacac gacggggagt caggcaacta tggatgaacg aaatagacag   6840
atcgctgaga taggtgcctc actgattaag cattggtaac tgtcagacca agtttactca   6900
tatatacttt agattgattt aaaacttcat ttttaattta aaaggatcta ggtgaagatc   6960
ctttttgata atctcatgac caaaatccct taacgtgagt tttcgttcca ctgagcgtca   7020
gaccccgtag aaaagatcaa aggatcttct tgagatcctt tttttctgcg cgtaatctgc   7080
tgcttgcaaa caaaaaaacc accgctacca gcggtggttt gtttgccgga tcaagagcta   7140
ccaactcttt ttccgaaggt aactggcttc agcagagcgc agataccaaa tactgttctt   7200
ctagtgtagc cgtagttagg ccaccacttc aagaactctg tagcaccgcc tacatacctc   7260
gctctgctaa tcctgttacc agtggctgct gccagtggcg ataagtcgtg tcttaccggg   7320
ttggactcaa gacgatagtt accggataag gcgcagcggt cgggctgaac ggggggttcg   7380
tgcacacagc ccagcttgga gcgaacgacc tacaccgaac tgagatacct acagcgtgag   7440
ctatgagaaa gcgccacgct tcccgaagag agaaaggcgg acaggtatcc ggtaagcggc   7500
agggtcggaa caggagagcg cacgagggag cttccagggg gaaacgcctg gtatctttat   7560
agtcctgtcg ggtttcgcca cctctgactt gagcgtcgat ttttgtgatg ctcgtcaggg   7620
```

-continued

| | |
|---|---|
| gggcggagcc tatggaaaaa cgccagcaac gcggcctttt tacggttcct ggccttttgc | 7680 |
| tggccttttg ctcacatgtt ctttcctgcg ttatcccctg attctgtgga taaccgtatt | 7740 |
| accgcctttg agtgagctga taccgctcgc cgcagccgaa cgaccgagcg cagcgagtca | 7800 |
| gtgagcgagg aagcggaaga gcgcccaata cgcaaaccgc ctctccccgc gcgttggccg | 7860 |
| attcattaat gcagctggca cgacaggttt cccgactgga aagcgggcag tgagcgcaac | 7920 |
| gcaattaatg tgagttagct cactcattag gcaccccagg ctttacactt tatgcttccg | 7980 |
| gctcgtatgt tgtgtggaat tgtgagcgga taacaatttc acacaggaaa cagctatgac | 8040 |
| catgattacg ccaagcgcgc aattaaccct cactaaaggg aacaaaagct ggagctgcaa | 8100 |
| gctt | 8104 |